US012723085B2

(12) United States Patent
Jin et al.

(10) Patent No.: US 12,723,085 B2
(45) Date of Patent: Sep. 1, 2026

(54) ANTI-TIGIT ANTIBODY AND DOUBLE ANTIBODY AND THEIR APPLICATION

(71) Applicant: NANJING SANHOME PHARMACEUTICAL CO., LTD., Nanjing (CN)

(72) Inventors: Liang Jin, Nanjing (CN); Yang Xiao, Nanjing (CN); Liwen Zhao, Nanjing (CN); Cheng Luo, Nanjing (CN); Fei Gao, Nanjing (CN)

(73) Assignee: NANJING SANHOME PHARMACEUTICAL CO., LTD., Nanjing (CN)

( * ) Notice: Subject to any disclaimer, the term of this patent is extended or adjusted under 35 U.S.C. 154(b) by 615 days.

(21) Appl. No.: 18/027,493

(22) PCT Filed: Sep. 22, 2021

(86) PCT No.: PCT/CN2021/119496
§ 371 (c)(1),
(2) Date: Mar. 21, 2023

(87) PCT Pub. No.: WO2022/063100
PCT Pub. Date: Mar. 31, 2022

(65) Prior Publication Data

US 2024/0262915 A1 Aug. 8, 2024

(30) Foreign Application Priority Data

Sep. 22, 2020 (CN) ........................ 202011000787.3

(51) Int. Cl.
*C07K 16/28* (2006.01)
*A61K 39/00* (2006.01)
*A61P 35/00* (2006.01)

(52) U.S. Cl.
CPC .......... *C07K 16/2827* (2013.01); *A61P 35/00* (2018.01); *A61K 2039/505* (2013.01); *C07K 2317/24* (2013.01); *C07K 2317/31* (2013.01); *C07K 2317/515* (2013.01); *C07K 2317/565* (2013.01)

(58) Field of Classification Search
CPC ............ C07K 16/2827; C07K 2317/24; C07K 2317/31; C07K 2317/515; C07K 2317/565; C07K 2317/55; C07K 2317/52; C07K 2317/56; C07K 2317/622; C07K 2317/73; C07K 2317/76; C07K 2317/92; C07K 16/2803; C07K 16/30; A61P 35/00; A61K 2039/505; Y02A 50/30; C12N 15/85; C12N 2800/107
See application file for complete search history.

(56) References Cited

U.S. PATENT DOCUMENTS

| | | | | |
|---|---|---|---|---|
| 10,189,902 | B2 | 1/2019 | Maurer et al. | |
| 2020/0131267 | A1 | 4/2020 | Carvalho et al. | |
| 2021/0040201 | A1 | 2/2021 | Shi et al. | |
| 2021/0380699 | A1 | 12/2021 | Campbell et al. | |
| 2023/0090014 | A1 * | 3/2023 | Xiao | C07K 16/2827 424/136.1 |

FOREIGN PATENT DOCUMENTS

| | | | | |
|---|---|---|---|---|
| CA | 3 026 474 A1 | 12/2017 | | |
| CN | 107207594 | 9/2017 | | |
| CN | 111196852 | 5/2020 | | |
| WO | WO 2018/234793 A2 | 12/2018 | | |
| WO | WO 2018/234793 A3 | 12/2018 | | |
| WO | WO 2019/165434 | 8/2019 | | |
| WO | WO 2020/020281 | 1/2020 | | |
| WO | WO 2020/096915 | 5/2020 | | |
| WO | WO-2021170082 A1 * | 9/2021 | | A61P 35/00 |

OTHER PUBLICATIONS

Chauvin JM, Zarour HM. TIGIT in cancer immunotherapy. J Immunother Cancer. Sep. 2020;8(2):e000957. (Year: 2020).*

Extended European Search Report issued in European Patent Application No. 21871470.7, dated Oct. 25, 2024.

Xiao, Y. et al., "Discovery of a novel anti PD-LI X TIGIT bispecific antibody for the treatment of solid tumors," *Cancer Treatment and Research Communications*, 29 (2021): 100467, 1-10.

Ma, L. et al., "A novel bispecific nanobody with PD-L1/TIGIT dual immune checkpoint blockade," *Biochemical and Biophysical Research Communications*, 531 (2020): 144-151.

PCT International Search Report and Written Opinion issued in International Patent Application No. PCT/CN2021/119496, dated Dec. 24, 2021.

* cited by examiner

*Primary Examiner* — Julie Wu
*Assistant Examiner* — Amber K Faust
(74) *Attorney, Agent, or Firm* — pH IP Law

(57) ABSTRACT

The present invention relates to the technical field of antibody drugs, and particularly relates to an anti-TIGIT antibody or antigen-binding fragment thereof, an anti-TIGIT/anti-PD-L1 antibody or antigen-binding fragment thereof, and pharmaceutical compositions containing an anti-TIGIT antibody or antigen-binding fragment thereof or an anti-TIGIT/anti-PD-L1 antibody or antigen-binding fragment thereof, and applications thereof. The anti-TIGIT/anti-PD-L1 antibody of the present invention has significant antitumor activity, and can be applied in the preparation of antitumor drugs.

17 Claims, 3 Drawing Sheets

Specification includes a Sequence Listing.

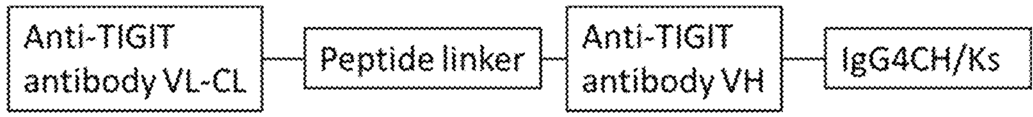
FIG. 3A
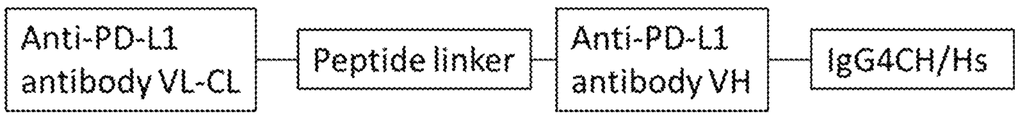
FIG. 3B
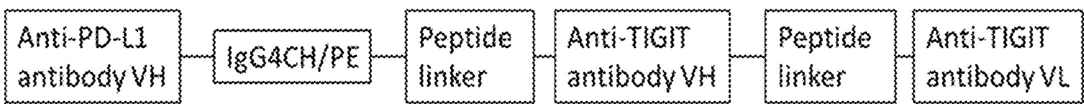
FIG. 4A
Anti-PD-L1 antibody VL-CL
FIG. 4B

ANTI-TIGIT ANTIBODY AND DOUBLE ANTIBODY AND THEIR APPLICATION

CROSS-REFERENCE TO RELATED APPLICATIONS

This application is a national phase application under 35 U.S.C. § 371 of International Patent Application No. PCT/CN2021/119496, filed Sep. 22, 2021, which claims the benefit of Chinese Patent Application No. 202011000787.3, filed Sep. 22, 2020.

INCORPORATION OF SEQUENCE LISTING

The sequence listing that is contained in the file named "OP0023-US-0045", which is 142,432 bytes (as measured in Microsoft Windows®) and was created on Jan. 13, 2026, is filed herewith by electronic submission, and is incorporated by reference herein.

FIELD

The present disclosure relates to the technical field of antibody drugs, and particularly relates to an anti-TIGIT antibody or antigen-binding fragment thereof, an anti-TIGIT/anti-PD-L1 antibody or antigen-binding fragment thereof, a pharmaceutical composition comprising the anti-TIGIT antibody or antigen-binding fragment thereof or an anti-TIGIT/anti-PD-L1 antibody or antigen-binding fragment thereof, and use thereof.

BACKGROUND

TIGIT is a member of the poliovirus receptor-binding protein family, belonging to the immunoglobulin superfamily, and consists of an extracellular immunoglobulin domain (IgV), a transmembrane domain, and an intracellular immunoreceptor tyrosine-based inhibitory motif (ITIM) and immunoglobulin tail tyrosine (ITT) motif. TIGIT is only expressed on lymphocytes, and is highly expressed on effector CD4+ T cells and regulatory T cells, CD4+ vesicular helper T cells, effector CD8+ T cells and NK cells. In the immune system, TIGIT competes with CD226 and CD96 for binding to PVR (CD155), and competes with CD226 and CD112R for binding to CD122. It coordinates the immune system and regulates immune activation and immune suppression through network signaling. Studies have shown that TIGIT plays an important role in the regulation of tumor immune suppression. Upon binding to its ligands PVR, PVR2 and PVR3 (a potential ligand), TIGIT inhibits the immune response through three different modes of action. The first mode of action is to trigger the rapid phosphorylation of PVR to transmit signals to antigen-presenting cells or tumor cells through TIGIT signaling, and TIGIT itself transmits its signals to lymphocytes through the intracellular ITIM/ITT domain. The second mode of action affecting the immune response is to inhibit the activity of T cells by inflammatory factors such as IL10 and TGF-β expressed and secreted by antigen-presenting cells after receiving the TIGIT signal. The third mode of action is to inhibit the activation of T cells by competing with CD226 to bind to PVR and interfering with the balance of CD226. Anti-TIGIT antibodies can block the signaling pathway, relieve tumor immune suppression, increase the cytotoxicity of effector T cells and NK cells, and establish long-term anti-tumor immune memory to achieve the effect of treating tumors.

Considering the important role of TIGIT in immune checkpoint regulation, there is still a need in the art to develop antagonistic antibodies specific to TIGIT for use in immunotherapy and cancer treatment alone or in combination with other agents.

PD-L1 is a 40 KD type I transmembrane protein that plays an important role in suppressing the immune system. PD-L1 forms an immune complex with PD-1 and B7-1 to negatively regulate the T cell receptor signaling pathway, thereby impeding the activation of T cells and inhibiting the anti-tumor activity of T cells. PD-1, as a receptor of PD-L1, is mainly involved in the activation of T cells, B cells, monocytes and myeloid cells. CD80 (B7-1) is a co-stimulatory molecule for T cells. The immune regulatory effect of PD-L1 mainly occurs in some chronic diseases, such as allogeneic transplantation, autoimmune diseases and cancer. PD-L1 is highly expressed on the surface of many tumor cells and tumor-infiltrating immune cells, including most solid tumors and hematological lymphomas, such as myeloma, prostate cancer, breast cancer, colon cancer, lung cancer, gastric cancer, and melanoma. Therefore, PD-L1 can be used as an important target for tumor therapy. At present, monoclonal antibodies that exert anti-tumor effects by blocking PD-L1 have been widely used clinically, and have shown strong anti-tumor activity in multiple tumors.

A disease is often controlled by various signaling pathways, cytokines, and receptor regulation mechanisms in the body. Combined blockade of multiple immune checkpoint pathways may be an ingenious and necessary anti-tumor immunotherapy strategy. Anti-TIGIT/anti-PD-L1 bispecific antibodies can block PD-1/PD-L1 pathway and TIGIT/CD155 pathway to activate immune response, and recruit tumor cells to lymphocytes to further improve anti-tumor activity. Therefore, it is particularly necessary to develop an anti-TIGIT/anti-PD-L1 bispecific antibody.

SUMMARY

One aspect of the present disclosure provides an anti-TIGIT antibody or antigen-binding fragment thereof, which comprises a heavy chain variable region and/or a light chain variable region, wherein the heavy chain variable region comprises a complementarity determining region 1 of the heavy chain variable region (H1CDR1), a complementarity determining region 2 of the heavy chain variable region (H1CDR2) and/or a complementarity determining region 3 of the heavy chain variable region (H1CDR3), and the light chain variable region comprises a complementarity determining region 1 of the light chain variable region (L1CDR1), a complementarity determining region 2 of the light chain variable region (L1CDR2) and/or a complementarity determining region 3 of the light chain variable region (L1CDR3).

In some embodiments, the present disclosure provides an anti-TIGIT antibody or antigen-binding fragment thereof comprising a heavy chain variable region and a light chain variable region, wherein:

(1) the heavy chain variable region comprises H1CDR1, H1CDR2 and H1CDR3 selected from the group consisting of:

(a1) amino acid sequences set forth in SEQ ID NOs: 25, 26 and 27;

a2) amino acid sequences set forth in SEQ ID NOs: 28, 29 and 30; and (a3) amino acid sequences having at least 85% sequence identity to the amino acid sequences set forth in (a1) or (a2); and (2) the light chain variable region comprises L1CDR1, L1CDR2 and L1CDR3 selected from the group consisting of:

(a4) amino acid sequences set forth in SEQ ID NOs: 31, 32 and 33;

(a5) amino acid sequences set forth in SEQ ID NOs: 34, 35 and 36; and (a6) amino acid sequences having at least 85% sequence identity to the amino acid sequences set forth in (a4) or (a5).

In a specific embodiment, the present disclosure provides an anti-TIGIT antibody or antigen-binding fragment thereof, comprising the heavy chain variable region comprising H1CDR1, H1CDR2 and H1CDR3 with amino acid sequences set forth in SEQ ID NOs: 25, 26 and 27 or with amino acid sequences having at least 85% sequence identity to the amino acid sequences set forth in SEQ ID NOs: 25, 26 and 27, respectively, and the light chain variable region comprising L1CDR1, L1CDR2, and L1CDR3 with amino acid sequences set forth in SEQ ID NOs: 31, 32, and 33 or with amino acid sequences having at least 85% sequence identity to the amino acid sequences set forth in SEQ ID NOs: 31, 32, and 33, respectively.

In a specific embodiment, the present disclosure provides an anti-TIGIT antibody or antigen-binding fragment thereof, comprising the heavy chain variable region comprising H1CDR1, H1CDR2 and H1CDR3 with amino acid sequences set forth in SEQ ID NOs: 28, 29 and 30 or with amino acid sequences having at least 85% sequence identity to the amino acid sequences set forth in SEQ ID NOs: 28, 29 and 30, respectively, and the light chain variable region comprising L1CDR1, L1CDR2, and L1CDR3 with amino acid sequences set forth in SEQ ID NOs: 34, 35, and 36 or with amino acid sequences having at least 85% sequence identity to the amino acid sequences set forth in SEQ ID NOs: 34, 35, and 36, respectively.

In some specific embodiments, the anti-TIGIT antibody or antigen-binding fragment thereof according to the present disclosure is a monoclonal antibody or antigen-binding fragment thereof.

In some specific embodiments, the anti-TIGIT antibody or antigen-binding fragment thereof according to the present disclosure is a murine-derived antibody or antigen-binding fragment thereof, a chimeric antibody or antigen-binding fragment thereof, or a humanized antibody or antigen-binding fragment thereof.

In some specific embodiments, the present disclosure provides an anti-TIGIT antibody or antigen-binding fragment thereof comprising a heavy chain variable region and a light chain variable region, wherein (1) the heavy chain variable region has an amino acid sequence selected from the group consisting of:

(b1) amino acid sequences set forth in SEQ ID NO: 75, SEQ ID NO: 76, SEQ ID NO: 79, SEQ ID NO: 80, SEQ ID NO: 81, SEQ ID NO: 82, SEQ ID NO: 83, SEQ ID NO: 88, SEQ ID NO: 89, SEQ ID NO: 90, SEQ ID NO: 91 and SEQ ID NO: 92;

(b2) amino acid sequences derived from the amino acid sequences set forth in (b1) by substitution, deletion or addition of one or more amino acids and functionally identical or similar to the amino acid sequences set forth in (b1); and (b3) amino acid sequences having at least 80% sequence identity to the amino acid sequences set forth in (b1); and (2) the light chain variable region has an amino acid sequence selected from the group consisting of:

(b4) amino acid sequences set forth in SEQ ID NO: 77, SEQ ID NO: 78, SEQ ID NO: 84, SEQ ID NO: 85, SEQ ID NO: 86, SEQ ID NO: 87, SEQ ID NO: 93, SEQ ID NO: 94, SEQ ID NO: 95, SEQ ID NO: 96, and SEQ ID NO: 97;

(b5) amino acid sequences derived from the amino acid sequences set forth in (b4) by substitution, deletion or addition of one or more amino acids and functionally identical or similar to the amino acid sequences set forth in (b4); and (b6) amino acid sequences having at least 80% sequence identity to the amino acid sequences set forth in (b4).

In some specific embodiments, the present disclosure provides an anti-TIGIT antibody or antigen-binding fragment thereof, wherein the heavy chain variable region has an amino acid sequence selected from the group consisting of: an amino sequence set forth in SEQ ID NO: 75, amino acid sequences derived from the amino acid sequence set forth in SEQ ID NO: 75 by substitution, deletion or addition of one or more amino acids and functionally identical to the amino acid sequence set forth in SEQ ID NO: 75, and amino acid sequences having at least 85% sequence identity to the amino acid sequence set forth in SEQ ID NO: 75, and the light chain variable region has an amino acid sequence selected from the group consisting of: an amino sequence set forth in SEQ ID NO: 77, amino acid sequences derived from the amino acid sequence set forth in SEQ ID NO: 77 by substitution, deletion or addition of one or more amino acids and functionally identical to the amino acid sequence set forth in SEQ ID NO: 77, and amino acid sequences having at least 85% sequence identity to the amino acid sequence set forth in SEQ ID NO: 77.

In some specific embodiments, the present disclosure provides an anti-TIGIT antibody or antigen-binding fragment thereof, wherein the heavy chain variable region has an amino acid sequence selected from the group consisting of: an amino sequence set forth in SEQ ID NO: 76, amino acid sequences derived from the amino acid sequence set forth in SEQ ID NO: 76 by substitution, deletion or addition of one or more amino acids and functionally identical to the amino acid sequence set forth in SEQ ID NO: 76, and amino acid sequences having at least 85% sequence identity to the amino acid sequence set forth in SEQ ID NO: 76, and the light chain variable region has an amino acid sequence selected from the group consisting of: an amino sequence set forth in SEQ ID NO: 78, amino acid sequences derived from the amino acid sequence set forth in SEQ ID NO: 78 by substitution, deletion or addition of one or more amino acids and functionally identical to the amino acid sequence set forth in SEQ ID NO: 78, and amino acid sequences having at least 85% sequence identity to the amino acid sequence set forth in SEQ ID NO: 78.

In some specific embodiments, the present disclosure provides an anti-TIGIT antibody or antigen-binding fragment thereof, wherein the heavy chain variable region has an amino acid sequence selected from the group consisting of: an amino sequence set forth in SEQ ID NO: 75, amino acid sequences derived from the amino acid sequence set forth in SEQ ID NO: 75 by substitution, deletion or addition of one or more amino acids and functionally identical to the amino acid sequence set forth in SEQ ID NO: 75, and amino acid sequences comprising H1CDR1, H1CDR2 and H1CDR3 set forth in SEQ ID NO: 25, 26 and 27 and having at least 85% sequence identity to the amino acid sequence set forth in SEQ ID NO: 75, and the light chain variable region has an amino acid sequence selected from the group consisting of: an amino sequence set forth in SEQ ID NO: 77, amino acid sequences derived from the amino acid sequence set forth in SEQ ID NO: 77 by substitution, deletion or addition of one or more amino acids and functionally identical to the amino acid sequence set forth in SEQ ID NO: 77, and amino acid sequences comprising L1CDR1, L1CDR2 and L1CDR3 set forth in SEQ ID NO: 31, 32 and 33 and having at least 85% sequence identity to the amino acid sequence set forth in SEQ ID NO: 77.

In some specific embodiments, the present disclosure provides an anti-TIGIT antibody or an antigen-binding fragment thereof, wherein the heavy chain variable region has an amino acid sequence selected from the group consisting of: an amino sequence set forth in SEQ ID NO: 76, amino acid sequences derived from the amino acid sequence set forth in SEQ ID NO: 76 by substitution, deletion or addition of one or more amino acids and functionally identical to the amino acid sequence set forth in SEQ ID NO: 76, and amino acid sequences comprising H1CDR1, H1CDR2 and H1CDR3 set forth in SEQ ID NO: 28, 29 and 30 and having at least 85% sequence identity to the amino acid sequence set forth in SEQ ID NO: 76, and the light chain variable region has an amino acid sequence selected from the group consisting of: an amino sequence set forth in SEQ ID NO: 78, amino acid sequences derived from the amino acid sequence set forth in SEQ ID NO: 78 by substitution, deletion or addition of one or more amino acids and functionally identical to the amino acid sequence set forth in SEQ ID NO: 78, and amino acid sequences comprising L1CDR1, L1CDR2 and L1CDR3 set forth in SEQ ID NO: 34, 35 and 36 and having at least 85% sequence identity to the amino acid sequence set forth in SEQ ID NO: 78.

In some specific embodiments, the anti-TIGIT antibody according to the present disclosure is a murine-derived antibody, which further comprises a heavy chain constant region of murine-derived IgG1, IgG2a, IgG2b, IgG2c, IgG3 or a variant thereof, and a light chain constant region of murine-derived κ chain or a variant thereof.

In some preferred embodiments, the murine-derived anti-TIGIT antibody according to the present disclosure further comprises a heavy chain constant region of murine-derived IgG1, IgG2a, IgG2b, IgG2c or a variant thereof, and a light chain constant region of murine-derived κ chain or a variant thereof.

In some specific embodiments, the present disclosure provides a humanized anti-TIGIT antibody or antigen-binding fragment thereof, wherein:

(1) the heavy chain variable region has an amino acid sequence selected from the group consisting of:

(c1) amino acid sequences set forth in SEQ ID NO: 98 and SEQ ID NO: 99;

(c2) amino acid sequences derived from the amino acid sequences set forth in (c1) by substitution, deletion or addition of one or more amino acids and functionally identical or similar to the amino acid sequences set forth in (c1), and (c3) amino acid sequences having at least 80% sequence identity to the amino acid sequences set forth in (c1); and (2) the light chain variable region has an amino acid sequence selected from the group consisting of:

(c4) amino acid sequences set forth in SEQ ID NO: 100 and SEQ ID NO: 101;

(c5) amino acid sequences derived from the amino acid sequences set forth in (c4) by substitution, deletion or addition of one or more amino acids and functionally identical or similar to the amino acid sequences set forth in (c4), and (c6) amino acid sequences having at least 80% sequence identity to the amino acid sequences set forth in (c4).

In some specific embodiments, the present disclosure provides a humanized anti-TIGIT antibody or antigen-binding fragment thereof, wherein the heavy chain variable region has an amino acid sequence selected from the group consisting of: an amino sequence set forth in SEQ ID NO: 98, amino acid sequences derived from the amino acid sequence set forth in SEQ ID NO: 98 by substitution, deletion or addition of one or more amino acids and functionally identical to the amino acid sequence set forth in SEQ ID NO: 98, and amino acid sequences having at least 85% sequence identity to the amino acid sequence set forth in SEQ ID NO: 98, and the light chain variable region has an amino acid sequence selected from the group consisting of: an amino sequence set forth in SEQ ID NO: 100, amino acid sequences derived from the amino acid sequence set forth in SEQ ID NO: 100 by substitution, deletion or addition of one or more amino acids and functionally identical to the amino acid sequence set forth in SEQ ID NO: 100, and amino acid sequences having at least 85% sequence identity to the amino acid sequence set forth in SEQ ID NO: 100.

In some specific embodiments, the present disclosure provides a humanized anti-TIGIT antibody or antigen-binding fragment thereof, wherein the heavy chain variable region has an amino acid sequence selected from the group consisting of: an amino sequence set forth in SEQ ID NO: 99, amino acid sequences derived from the amino acid sequence set forth in SEQ ID NO: 99 by substitution, deletion or addition of one or more amino acids and functionally identical to the amino acid sequence set forth in SEQ ID NO: 99, and amino acid sequences having at least 85% sequence identity to the amino acid sequence set forth in SEQ ID NO: 99, and the light chain variable region has an amino acid sequence selected from the group consisting of: an amino sequence set forth in SEQ ID NO: 101, amino acid sequences derived from the amino acid sequence set forth in SEQ ID NO: 101 by substitution, deletion or addition of one or more amino acids and functionally identical to the amino acid sequence set forth in SEQ ID NO: 101, and amino acid sequences having at least 85% sequence identity to the amino acid sequence set forth in SEQ ID NO: 101.

In some specific embodiments, the present disclosure provides a humanized anti-TIGIT antibody or antigen-binding fragment thereof, wherein the heavy chain variable region has an amino acid sequence selected from the group consisting of: an amino sequence set forth in SEQ ID NO: 98, amino acid sequences derived from the amino acid sequence set forth in SEQ ID NO: 98 by substitution, deletion or addition of one or more amino acids and functionally identical to the amino acid sequence set forth in SEQ ID NO: 98, and amino acid sequences comprising H1CDR1, H1CDR2 and H1CDR3 set forth in SEQ ID NOs: 25, 26 and 27 and having at least 85% sequence identity to the amino acid sequence set forth in SEQ ID NO: 98, and the light chain variable region has an amino acid sequence selected from the group consisting of: an amino sequence set forth in SEQ ID NO: 100, amino acid sequences derived from the amino acid sequence set forth in SEQ ID NO: 100 by substitution, deletion or addition of one or more amino acids and functionally identical to the amino acid sequence set forth in SEQ ID NO: 100, and amino acid sequences comprising L1CDR1, L1CDR2 and L1CDR3 set forth in SEQ ID NOs: 31, 32 and 33 and having at least 85% sequence identity to the amino acid sequence set forth in SEQ ID NO: 100.

In some specific embodiments, the present disclosure provides a humanized anti-TIGIT antibody or antigen-binding fragment thereof, wherein the heavy chain variable region has an amino acid sequence selected from the group consisting of: an amino sequence set forth in SEQ ID NO: 99, amino acid sequences derived from the amino acid sequence set forth in SEQ ID NO: 99 by substitution, deletion or addition of one or more amino acids and functionally identical to the amino acid sequence set forth in SEQ ID NO: 99, and amino acid sequences comprising H1CDR1, H1CDR2 and H1CDR3 set forth in SEQ ID NO: 28, 29 and 30 and having at least 85% sequence identity to the amino acid sequence set forth in SEQ ID NO: 99, and the light chain variable region has an amino acid sequence selected from the group consisting of: an amino sequence set forth in SEQ ID NO: 101, amino acid sequences derived from the amino acid sequence set forth in SEQ ID NO: 101 by substitution, deletion or addition of one or more amino acids and functionally identical to the amino acid sequence set forth in SEQ ID NO: 101, and amino acid sequences comprising L1CDR1, L1CDR2 and L1CDR3 set forth in SEQ ID NO: 34, 35 and 36 and having at least 85% sequence identity to the amino acid sequence set forth in SEQ ID NO: 101.

In a preferred embodiment of the present disclosure, the murine-derived anti-TIGIT antibody or antigen-binding fragment thereof may further comprise a light chain constant region of murine-derived κ, λ chain or a variant thereof, and/or further comprise a heavy chain constant region of murine-derived IgG1, IgG2a, IgG2b, IgG2c, IgG3, or a variant thereof.

In a preferred embodiment of the present disclosure, the antibody light chain of the chimeric anti-TIGIT antibody or antigen-binding fragment thereof further comprises a light chain constant region of murine-derived κ, λ chain or a mutant sequence thereof. The antibody heavy chain of the chimeric anti-TIGIT antibody or antigen-binding fragment thereof further comprises a heavy chain constant region of murine-derived IgG1, IgG2a, IgG2b, IgG2c, IgG3 or a mutant sequence thereof, preferably comprises a heavy chain constant region of human IgG1, IgG2a, IgG2b, IgG2c, or IgG4 constant region that has significantly reduced ADCC (antibody-dependent cell-mediated cytotoxicity) after amino acid mutation.

In some specific embodiments, the humanized anti-TIGIT antibody or antigen-binding fragment thereof of the present disclosure further comprises a heavy chain constant region of human IgG1, IgG2a, IgG2b, IgG2c, IgG3 or a variant thereof, and a light chain constant region of human κ, λ chain or a variant thereof. In some preferred embodiments, the humanized anti-TIGIT antibody or antigen-binding fragment thereof of the present disclosure further comprises a heavy chain constant region of human IgG1, IgG2a, IgG2b, IgG2c or a variant thereof, and a light chain constant region of human κ chain or a variant thereof.

In some embodiments, the present disclosure provides an anti-TIGIT antibody or antigen-binding fragment thereof, wherein the antigen-binding fragment is Fab, Fv, sFv or F(ab)2.

Another aspect of the present disclosure provides an isolated nucleic acid encoding the anti-TIGIT antibody or antigen-binding fragment thereof according to the present disclosure.

In some specific embodiments, the isolated nucleic acid according to the present disclosure comprises a nucleotide sequence encoding a heavy chain variable region with an amino acid sequence set forth in SEQ ID NO: 75, SEQ ID NO: 76, SEQ ID NO: 98 or SEQ ID NO: 99, and a nucleotide sequence encoding a light chain variable region with an amino acid sequence set forth in SEQ ID NO: 77, SEQ ID NO: 78, SEQ ID NO: 100 or SEQ ID NO: 101.

In a specific embodiment, the isolated nucleic acid according to the present disclosure comprises a nucleotide sequence encoding the heavy chain variable region of SEQ ID NO: 75 and a nucleotide sequence encoding the light chain variable region of SEQ ID NO: 77.

In a specific embodiment, the isolated nucleic acid according to the present disclosure comprises a nucleotide sequence encoding the heavy chain variable region of SEQ ID NO: 76 and a nucleotide sequence encoding the light chain variable region of SEQ ID NO: 78.

In a specific embodiment, the isolated nucleic acid according to the present disclosure comprises a nucleotide sequence encoding the heavy chain variable region of SEQ ID NO: 98 and a nucleotide sequence encoding the light chain variable region of SEQ ID NO: 100.

In a specific embodiment, the isolated nucleic acid according to the present disclosure comprises a nucleotide sequence encoding the heavy chain variable region of SEQ ID NO: 99 and a nucleotide sequence encoding the light chain variable region of SEQ ID NO: 101.

Another aspect of the present disclosure provides an expression vector expressing the anti-TIGIT antibody or antigen-binding fragment thereof of the present disclosure. The expression vector according to the present disclosure comprises the isolated nucleic acid molecule of the present disclosure.

Another aspect of the present disclosure provides a host cell transformed with the above expression vector.

In some embodiments, the host cell according to the present disclosure is selected from the group consisting of prokaryotic cells and eukaryotic cells. In some embodiments, the host cell is bacteria, preferably *Escherichia coli*. In another preferred embodiment, the host cell is mammalian cell.

Another aspect of the present disclosure provides a method for producing the anti-TIGIT antibody or antigen-binding fragment thereof of the present disclosure, comprising expressing the antibody in the host cell and isolating the antibody from the host cell.

Another aspect of the present disclosure provides a pharmaceutical composition comprising the humanized anti-TIGIT antibody or antigen-binding fragment thereof of the present disclosure and a pharmaceutically acceptable carrier. In some embodiments, the present disclosure provides a pharmaceutical composition comprising the humanized anti-TIGIT antibody or antigen-binding fragment thereof of the present disclosure, and additional active components, such as other antibodies, targeted drugs, and the like. In some embodiments, the pharmaceutically acceptable carrier is selected from the group consisting of antioxidants, polypeptides, proteins, hydrophilic polymers, amino acids, saccharides, chelating agents, alditols, ions, and surfactants. In a specific embodiment, the pharmaceutically acceptable carrier is a buffered aqueous solution. In another specific embodiment, the pharmaceutically acceptable carrier is in the form of liposomes.

The humanized anti-TIGIT antibody or antigen-binding fragment thereof of the present disclosure may be combined with a pharmaceutically acceptable carrier, diluent or excipient to prepare a pharmaceutical preparation suitable for oral or parenteral administration. The routes of administration include, but are not limited to oral, intradermal, intramuscular, intraperitoneal, intravenous, intracerebral, intraocular, intratracheal, subcutaneous, and intranasal routes. The preparation may be administered by any means, for example, by infusion or bolus injection, by the means of absorption through epithelium or skin mucosa (for example, oral mucosa or rectum, etc.). Administration can be systemic or local. The preparation can be prepared by methods known in the art, and contains a carrier, diluent or excipient conventionally used in the field of pharmaceutical preparations.

Another aspect of the present disclosure provides a method for inhibiting TIGIT activity comprising administering the anti-TIGIT antibody or antigen-binding fragment thereof of the present disclosure or the pharmaceutical composition of the present disclosure to a subject in need thereof.

Another aspect of the present disclosure provides a method for detecting or determining human TIGIT, comprising using the anti-TIGIT antibody or antigen-binding fragment thereof of the present disclosure.

Another aspect of the present disclosure provides a reagent for detecting or determining human TIGIT, comprising the anti-TIGIT antibody or antigen-binding fragment thereof of the present disclosure.

Another aspect of the present disclosure provides a method for treating a disease associated with TIGIT, comprising administering to a subject a pharmaceutically effective amount of the TIGIT antibody or antigen-binding fragment thereof, the above pharmaceutical composition, or the above isolated nucleic acid molecule of the present disclosure. Another aspect of the present disclosure provides use of the anti-TIGIT antibody or antigen-binding fragment thereof of the present disclosure or the pharmaceutical composition of the present disclosure in the manufacture of a medicament for a TIGIT-associated disease. In some embodiments, the medicament for a TIGIT-associated disease is used to treat a T-cell dysfunctional disorder, such as a tumor, an immune disease, or an infectious disease. In some embodiments, the tumor includes non-small cell lung cancer, small cell lung cancer, renal cell carcinoma, colorectal cancer, ovarian cancer, breast cancer, pancreatic cancer, gastric cancer, bladder cancer, esophageal cancer, mesothelioma, melanoma, head and neck cancer, thyroid cancer, sarcoma, prostate cancer, glioblastoma, cervical cancer, thymic carcinoma, leukemia, lymphoma, myeloma, mycosis fungoides, Merkel cell carcinoma, adrenocortical carcinoma, hepatocellular carcinoma, pancreatic ductal adenocarcinoma, pheochromocytoma, ganglioneuroma, endometrial carcinoma, ovarian serous cystadenocarcinoma, and the like. In some embodiments, the immune disease includes arthritis, inflammatory bowel disease and psoriasis. In some embodiments, the infectious disease is a chronic viral infection.

The present disclosure provides an anti-TIGIT/anti-PD-L1 antibody, comprising an anti-TIGIT antibody or antigen-binding fragment thereof, and an anti-PD-L1 antibody or antigen-binding fragment thereof, wherein the anti-TIGIT antibody or antigen-binding fragment thereof comprises a first heavy chain variable region and/or a first light chain variable region, wherein the first heavy chain variable region comprises a complementarity determining region 1 of the first heavy chain-variable region (H1CDR1), a complementarity determining region 2 of the first heavy chain variable region (H1CDR2) and/or a complementarity determining region 3 of the first heavy chain variable region (H1CDR3); the first light chain variable region comprises a complementarity determining region 1 of the first light chain variable region (L1CDR1), a complementarity determining region 2 of the first light chain variable region (L1CDR2) and/or a complementarity determining region 3 of the first light chain variable region (L1CDR3); and the anti-PD-L1 antibody or antigen-binding fragment thereof is an antibody or antigen-binding fragment thereof that specifically binds to PD-L1.

In some embodiments, the present disclosure provides an anti-TIGIT/anti-PD-L1 antibody comprising an anti-TIGIT antibody or antigen-binding fragment thereof and an anti-PD-L1 antibody or antigen-binding fragment thereof, wherein the anti-TIGIT antibody or antigen-binding fragment thereof comprises a first heavy chain variable region and a first light chain variable region, wherein:

(1) the first heavy chain variable region comprises H1CDR1, H1CDR2 and H1CDR3 selected from the group consisting of:

(a1) amino acid sequences set forth in SEQ ID NOs: 25, 26 and 27;

(a2) amino acid sequences set forth in SEQ ID NOs: 28, 29 and 30; and (a3) amino acid sequences having at least 85% sequence identity to the amino acid sequences set forth in (a1) or (a2); and (2) the first light chain variable region comprises L1CDR1, L1CDR2 and L1CDR3 selected from the group consisting of:

(a4) amino acid sequences set forth in SEQ ID NOs: 31, 32 and 33;

(a5) amino acid sequences set forth in SEQ ID NOs: 34, 35 and 36; and (a6) amino acid sequences having at least 85% sequence identity to the amino acid sequences set forth in (a4) or (a5).

In some embodiments, for the anti-TIGIT/anti-PD-L1 antibody according to the present disclosure, the anti-TIGIT antibody or antigen-binding fragment thereof comprises:

the first heavy chain variable region comprising H1CDR1, H1CDR2 and H1CDR3 with amino acid sequences set forth in SEQ ID NOs: 25, 26 and 27, or with amino acid sequences having at least 85% sequence identity to the amino acid sequences set forth in SEQ ID NOs: 25, 26 and 27, respectively, and the first light chain variable region comprising L1CDR1, L1CDR2 and L1CDR3 with amino acid sequences set forth in SEQ ID NOs: 31, 32 and 33, or with amino acid sequences having at least 85% sequence identity to the amino acid sequences set forth in SEQ ID NOs: 31, 32 and 33, respectively; or the first heavy chain variable region comprising H1CDR1, H1CDR2 and H1CDR3 with amino acid sequences set forth in SEQ ID NOs: 28, 29 and 30, or with amino acid sequences having at least 85% sequence identity to the amino acid sequences set forth in SEQ ID NOs: 28, 29 and 30, respectively, and the first light chain variable region comprising L1CDR1, L1CDR2 and L1CDR3 with amino acid sequences set forth in SEQ ID NOs: 34, 35 and 36, or with amino acid sequences having at least 85% sequence identity to the amino acid sequences set forth in SEQ ID NOs: 34, 35 and 36, respectively.

In some embodiments, for the anti-TIGIT/anti-PD-L1 antibody according to the present disclosure, the anti-TIGIT antibody or antigen-binding fragment thereof comprises a first heavy chain variable region and a first light chain variable region, wherein:

(1) the first heavy chain variable region has an amino acid sequence selected from the group consisting of:

(b1) amino acid sequences set forth in SEQ ID NO: 75, SEQ ID NO: 76, SEQ ID NO: 79, SEQ ID NO: 80, SEQ ID NO: 81, SEQ ID NO: 82, SEQ ID NO: 83, SEQ ID NO: 88, SEQ ID NO: 89, SEQ ID NO: 90, SEQ ID NO: 91 and SEQ ID NO: 92;

(b2) amino acid sequences derived from the amino acid sequences set forth in (b1) by substitution, deletion or addition of one or more amino acids and functionally identical or similar to the amino acid sequences set forth in (b1); and (b3) amino acid sequences having at least 80% sequence identity to the amino acid sequences set forth in (b1); and (2) the light chain variable region has an amino acid sequence selected from the group consisting of:

(b4) amino acid sequences set forth in SEQ ID NO: 77, SEQ ID NO: 78, SEQ ID NO: 84, SEQ ID NO: 85, SEQ ID NO: 86, SEQ ID NO: 87, SEQ ID NO: 93, SEQ ID NO: 94, SEQ ID NO: 95, SEQ ID NO: 96, and SEQ ID NO: 97;

(b5) amino acid sequences derived from the amino acid sequences set forth in (b4) by substitution, deletion or addition of one or more amino acids and functionally identical or similar to the amino acid sequences set forth in (b4); and (b6) amino acid sequences having at least 80% sequence identity to the amino acid sequences set forth in (b4).

In some embodiments, for the anti-TIGIT/anti-PD-L1 antibody according to the present disclosure, the anti-TIGIT antibody or antigen-binding fragment thereof comprises a first heavy chain variable region and a first light chain variable region, wherein:

the first heavy chain variable region has an amino acid sequence selected from the group consisting of: an amino sequence set forth in SEQ ID NO: 75, amino acid sequences derived from the amino acid sequence set forth in SEQ ID NO: 75 by substitution, deletion or addition of one or more amino acids and functionally identical to the amino acid sequence set forth in SEQ ID NO: 75, and amino acid sequences comprising H1CDR1, H1CDR2 and H1CDR3 set forth in SEQ ID NOs: 25, 26 and 27 and having at least 85% sequence identity to the amino acid sequence set forth in SEQ ID NO: 75, and the first light chain variable region has an amino acid sequence selected from the group consisting of: an amino sequence set forth in SEQ ID NO: 77, amino acid sequences derived from the amino acid sequence set forth in SEQ ID NO: 77 by substitution, deletion or addition of one or more amino acids and functionally identical to the amino acid sequence set forth in SEQ ID NO: 77, and amino acid sequences comprising L1CDR1, L1CDR2 and L1CDR3 set forth in SEQ ID NOs: 31, 32 and 33 and having at least 85% sequence identity to the amino acid sequence set forth in SEQ ID NO: 77; or the first heavy chain variable region has an amino acid sequence selected from the group consisting of: an amino sequence set forth in SEQ ID NO: 76, amino acid sequences derived from the amino acid sequence set forth in SEQ ID NO: 76 by substitution, deletion or addition of one or more amino acids and functionally identical to the amino acid sequence set forth in SEQ ID NO: 76, and amino acid sequences comprising H1CDR1, H1CDR2 and H1CDR3 set forth in SEQ ID NOs: 28, 29 and 30 and having at least 85% sequence identity to the amino acid sequence set forth in SEQ ID NO: 76, and the first light chain variable region has an amino acid sequence selected from the group consisting of: an amino sequence set forth in SEQ ID NO: 78, amino acid sequences derived from the amino acid sequence set forth in SEQ ID NO: 78 by substitution, deletion or addition of one or more amino acids and functionally identical to the amino acid sequence set forth in SEQ ID NO: 78, and amino acid sequences comprising L1CDR1, L1CDR2 and L1CDR3 set forth in SEQ ID NOs: 34, 35 and 36 and having at least 85% sequence identity to the amino acid sequence set forth in SEQ ID NO: 78. In some embodiments, for the anti-TIGIT/anti-PD-L1 antibody according to the present disclosure, the anti-TIGIT antibody or antigen-binding fragment thereof is a humanized antibody or antigen-binding fragment thereof, comprising a first heavy chain variable region and a first light chain variable region, wherein:

(1) the first heavy chain variable region has an amino acid sequence selected from the group consisting of:

(c1) amino acid sequences set forth in SEQ ID NO: 98 and SEQ ID NO: 99;

(c2) amino acid sequences derived from the amino acid sequences set forth in (c1) by substitution, deletion or addition of one or more amino acids and functionally identical or similar to the amino acid sequences set forth in (c1); and (c3) amino acid sequences having at least 80% sequence identity to the amino acid sequences set forth in (c1); and (2) the light chain variable region has an amino acid sequence selected from the group consisting of:

(c4) amino acid sequences set forth in SEQ ID NO: 100 and SEQ ID NO: 101;

(c5) amino acid sequences derived from the amino acid sequences set forth in (c4) by substitution, deletion or addition of one or more amino acids and functionally identical or similar to the amino acid sequences set forth in (c4), and (c6) amino acid sequences having at least 80% sequence identity to the amino acid sequences set forth in (c4).

In some embodiments, for the anti-TIGIT/anti-PD-L1 antibody according to the present disclosure, the anti-TIGIT antibody or antigen-binding fragment thereof is a humanized antibody or antigen-binding fragment thereof, comprising a first heavy chain variable region and a first light chain variable region, wherein the first heavy chain variable region has an amino acid sequence selected from the group consisting of: an amino sequence set forth in SEQ ID NO: 98, amino acid sequences derived from the amino acid sequence set forth in SEQ ID NO: 98 by substitution, deletion or addition of one or more amino acids and functionally identical to the amino acid sequence set forth in SEQ ID NO: 98, and amino acid sequences having at least 85% sequence identity to the amino acid sequence set forth in SEQ ID NO: 98, and the first light chain variable region has an amino acid sequence selected from the group consisting of: an amino sequence set forth in SEQ ID NO: 100, amino acid sequences derived from the amino acid sequence set forth in SEQ ID NO: 100 by substitution, deletion or addition of one or more amino acids and functionally identical to the amino acid sequence set forth in SEQ ID NO: 100, and amino acid sequences having at least 85% sequence identity to the amino acid sequence set forth in SEQ ID NO: 100; or the first heavy chain variable region has an amino acid sequence selected from the group consisting of: an amino sequence set forth in SEQ ID NO: 99, amino acid sequences derived from the amino acid sequence set forth in SEQ ID NO: 99 by substitution, deletion or addition of one or more amino acids and functionally identical to the amino acid sequence set forth in SEQ ID NO: 99, and amino acid sequences having at least 85% sequence identity to the amino acid sequence set forth in SEQ ID NO: 99, and the first light chain variable region has an amino acid sequence selected from the group consisting of: an amino sequence set forth in SEQ ID NO: 101, amino acid sequences derived from the amino acid sequence set forth in SEQ ID NO: 101 by substitution, deletion or addition of one or more amino acids and functionally identical to the amino acid sequence set forth in SEQ ID NO: 101, and amino acid sequences having at least 85% sequence identity to the amino acid sequence set forth in SEQ ID NO: 101.

In some preferred embodiments, the present disclosure provides an anti-TIGIT/anti-PD-L1 antibody comprising an anti-TIGIT antibody or antigen-binding fragment thereof and an anti-PD-L1 antibody or antigen-binding fragment thereof, wherein the anti-TIGIT antibody or antigen-binding fragment thereof is as defined in the above embodiments; and the anti-PD-L1 antibody or antigen-binding fragment thereof comprises a second heavy chain variable region and/or a second light chain variable region, wherein the second heavy chain variable region comprises a complementarity determining region 1 of the second heavy chain variable region (H2CDR1), a complementarity determining region 2 of the second heavy chain variable region (H2CDR2) and/or a complementarity determining region 3 of the second heavy chain variable region (H2CDR3), and the second light chain variable region comprises a complementarity determining region 1 of the second light chain variable region (L2CDR1), a complementarity determining region 2 of the second light chain variable region (L2CDR2) and/or a complementarity determining region 3 of the second light chain variable region (L2CDR3).

Further preferably, in some embodiments, the present disclosure provides an anti-TIGIT/anti-PD-L1 antibody comprising an anti-TIGIT antibody or antigen-binding fragment thereof and an anti-PD-L1 antibody or antigen-binding fragment thereof, wherein the anti-TIGIT antibody or antigen-binding fragment thereof is as defined in the above embodiments, and the anti-PD-L1 antibody or antigen-binding fragment thereof comprises a second heavy chain variable region and a second light chain variable region, wherein:

(1) the second heavy chain variable region comprises H2CDR1, H2CDR2 and H2CDR3 selected from the group consisting of:

(A1) amino acid sequences set forth in SEQ ID NOs: 1, 2 and 3;

(A2) amino acid sequences set forth in SEQ ID NOs: 4, 5 and 6;

(A3) amino acid sequences set forth in SEQ ID NOs: 7, 8 and 9;

(A4) amino acid sequences set forth in SEQ ID NOs: 10, 11 and 12; and (A5) amino acid sequences having at least 85% sequence identity to the amino acid sequences set forth in (A1), (A2), (A3) or (A4); and (2) the second light chain variable region comprises L2CDR1, L2CDR2 and L2CDR3 selected from the group consisting of:

(A6) amino acid sequences set forth in SEQ ID NOs: 13, 14 and 15;

(A7) amino acid sequences set forth in SEQ ID NOs: 16, 17 and 18;

(A8) amino acid sequences set forth in SEQ ID NOs: 19, 20 and 21;

(A9) amino acid sequences set forth in SEQ ID NOs: 22, 23 and 24;

(A10) amino acid sequences having at least 85% sequence identity to the amino acid sequences set forth in (A6), (A7), (A8) or (A9).

In some specific embodiments, the present disclosure provides an anti-TIGIT/anti-PD-L1 antibody comprising an anti-TIGIT antibody or antigen-binding fragment thereof and an anti-PD-L1 antibody or antigen-binding fragment thereof, wherein:

the anti-TIGIT antibody or antigen-binding fragment thereof comprises a first heavy chain variable region and a first light chain variable region, wherein:

(1) the first heavy chain variable region comprises H1CDR1, H1CDR2 and H1CDR3 selected from the group consisting of:

(a1) amino acid sequences set forth in SEQ ID NOs: 25, 26 and 27;

(a2) amino acid sequences set forth in SEQ ID NOs: 28, 29 and 30; and (a3) amino acid sequences having at least 85% sequence identity to the amino acid sequences set forth in (a1) or (a2); and (2) the first light chain variable region comprises L1CDR1, L1CDR2 and L1CDR3 selected from the group consisting of:

(a4) amino acid sequences set forth in SEQ ID NOs: 31, 32 and 33;

(a5) amino acid sequences set forth in SEQ ID NOs: 34, 35 and 36; and (a6) amino acid sequences having at least 85% sequence identity to the amino acid sequences set forth in (a4) or (a5); and the anti-PD-L1 antibody or antigen-binding fragment thereof comprises a second heavy chain variable region and a second light chain variable region, wherein:

(1) the second heavy chain variable region comprises H2CDR1, H2CDR2 and H2CDR3 selected from the group consisting of:

(A1) amino acid sequences set forth in SEQ ID NOs: 1, 2 and 3;

(A2) amino acid sequences set forth in SEQ ID NOs: 4, 5 and 6;

(A3) amino acid sequences set forth in SEQ ID NOs: 7, 8 and 9;

(A4) amino acid sequences set forth in SEQ ID NOs: 10, 11 and 12; and (A5) amino acid sequences having at least 85% sequence identity to the amino acid sequences set forth in (A1), (A2), (A3) or (A4); and (2) the second light chain variable region comprises L2CDR1, L2CDR2 and L2CDR3 selected from the group consisting of:

(A6) amino acid sequences set forth in SEQ ID NOs: 13, 14 and 15;

(A7) amino acid sequences set forth in SEQ ID NOs: 16, 17 and 18;

(A8) amino acid sequences set forth in SEQ ID NOs: 19, 20 and 21;

(A9) amino acid sequences set forth in SEQ ID NOs: 22, 23 and 24; and (A10) amino acid sequences having at least 85% sequence identity to the amino acid sequences set forth in (A6), (A7), (A8) or (A9).

In a specific embodiment, the present disclosure provides an anti-TIGIT/anti-PD-L1 antibody comprising an anti-TIGIT antibody or antigen-binding fragment thereof and an anti-PD-L1 antibody or antigen-binding fragment thereof, wherein the anti-TIGIT antibody or antigen-binding fragment thereof comprises the first heavy chain variable region comprising H1CDR1, H1CDR2 and H1CDR3 with amino acid sequences set forth in SEQ ID NOs: 28, 29 and 30, or with amino acid sequences having at least 85% sequence identity to the amino acid sequences set forth in SEQ ID NOs: 28, 29 and 30, respectively, and the first light chain variable region comprising L1CDR1, L1CDR2 and L1CDR3 with amino acid sequences set forth in SEQ ID NOs: 34, 35 and 36, or with amino acid sequences having at least 85% sequence identity to the amino acid sequences set forth in SEQ ID NOs: 34, 35 and 36, respectively; and the anti-PD-L1 antibody or antigen-binding fragment thereof comprises the second heavy chain variable region comprising H2CDR1, H2CDR2 and H2CDR3 with amino acid sequences set forth in SEQ ID NOs: 1, 2 and 3, or with amino acid sequences having at least 85% sequence identity to the amino acid sequences set forth in SEQ ID NOs: 1, 2, and 3, respectively, and the second light chain variable region comprising L2CDR1, L2CDR2, and L2CDR3 with amino acid sequences set forth in SEQ ID NOs: 13, 14, and 15, or with amino acid sequences having at least 85% sequence identity to the amino acid sequences set forth in SEQ ID NOs: 13, 14 and 15, respectively.

In a specific embodiment, the present disclosure provides an anti-TIGIT/anti-PD-L1 antibody comprising an anti-TIGIT antibody or antigen-binding fragment thereof and an anti-PD-L1 antibody or antigen-binding fragment thereof, wherein the anti-TIGIT antibody or antigen-binding fragment thereof comprises the first heavy chain variable region comprising H1CDR1, H1CDR2 and H1CDR3 with amino acid sequences set forth in SEQ ID NOs: 28, 29 and 30, or with amino acid sequences having at least 85% sequence identity to the amino acid sequences set forth in SEQ ID NOs: 28, 29 and 30, respectively, and the first light chain variable region comprising L1CDR1, L1CDR2 and L1CDR3 with amino acid sequences set forth in SEQ ID NOs: 34, 35 and 36, or with amino acid sequences having at least 85% sequence identity to the amino acid sequences set forth in SEQ ID NOs: 34, 35 and 36, respectively; and the anti-PD-L1 antibody or antigen-binding fragment thereof comprises the second heavy chain variable region comprising H2CDR1, H2CDR2 and H2CDR3 with amino acid sequences set forth in SEQ ID NOs: 7, 8 and 9, or with amino acid sequences having at least 85% sequence identity to the amino acid sequences set forth in SEQ ID NOs: 7, 8, and 9, respectively, and the second light chain variable region comprising L2CDR1, L2CDR2, and L2CDR3 with amino acid sequences set forth in SEQ ID NOs: 19, 20, and 21, or with amino acid sequences having at least 85% sequence identity to the amino acid sequences set forth in SEQ ID NOs: 19, 20, and 21, respectively.

In a specific embodiment, the present disclosure provides an anti-TIGIT/anti-PD-L1 antibody comprising an anti-TIGIT antibody or antigen-binding fragment thereof and an anti-PD-L1 antibody or antigen-binding fragment thereof, wherein the anti-TIGIT antibody or antigen-binding fragment thereof comprises the first heavy chain variable region comprising H1CDR1, H1CDR2 and H1CDR3 with amino acid sequences set forth in SEQ ID NOs: 28, 29 and 30, or with amino acid sequences having at least 85% sequence identity to the amino acid sequences set forth in SEQ ID NOs: 28, 29 and 30, respectively, and the first light chain variable region comprising L1CDR1, L1CDR2 and L1CDR3 with amino acid sequences set forth in SEQ ID NOs: 34, 35 and 36, or with amino acid sequences having at least 85% sequence identity to the amino acid sequences set forth in SEQ ID NOs: 34, 35 and 36, respectively; and the anti-PD-L1 antibody or antigen-binding fragment thereof comprises the second heavy chain variable region comprising H2CDR1, H2CDR2 and H2CDR3 with amino acid sequences set forth in SEQ ID NOs: 4, 5 and 6, or with amino acid sequences having at least 85% sequence identity to the amino acid sequences set forth in SEQ ID NOs: 4, 5 and 6, respectively, and the second light chain variable region comprising L2CDR1, L2CDR2, and L2CDR3 with amino acid sequences set forth in SEQ ID NOs: 16, 17, and 18, or with amino acid sequences having at least 85% sequence identity to the amino acid sequences set forth in SEQ ID NOs: 16, 17, and 18, respectively.

In a specific embodiment, the present disclosure provides an anti-TIGIT/anti-PD-L1 antibody comprising an anti-TIGIT antibody or antigen-binding fragment thereof and an anti-PD-L1 antibody or antigen-binding fragment thereof, wherein the anti-TIGIT antibody or antigen-binding fragment thereof comprises the first heavy chain variable region comprising H1CDR1, H1CDR2 and H1CDR3 with amino acid sequences set forth in SEQ ID NOs: 28, 29 and 30, or with amino acid sequences having at least 85% sequence identity to the amino acid sequences set forth in SEQ ID NOs: 28, 29 and 30, respectively, and the first light chain variable region comprising L1CDR1, L1CDR2 and L1CDR3 with amino acid sequences set forth in SEQ ID NOs: 34, 35 and 36, or with amino acid sequences having at least 85% sequence identity to the amino acid sequences set forth in SEQ ID NOs: 34, 35 and 36, respectively; and the anti-PD-L1 antibody or antigen-binding fragment thereof comprises the second heavy chain variable region comprising H2CDR1, H2CDR2 and H2CDR3 with amino acid sequences set forth in SEQ ID NOs: 10, 11 and 12, or with amino acid sequences having at least 85% sequence identity to the amino acid sequences set forth in SEQ ID NOs: 10, 11 and 12, respectively, and the second light chain variable region comprising L2CDR1, L2CDR2, and L2CDR3 with amino acid sequences set forth in SEQ ID NOs: 22, 23, and 24, or with amino acid sequences having at least 85% sequence identity to the amino acid sequences set forth in SEQ ID NOs: 22, 23, and 24, respectively.

In some specific embodiments, for the anti-TIGIT/anti-PD-L1 antibody according to the present disclosure, the anti-TIGIT antibody or antigen-binding fragment thereof and the anti-PD-L1 antibody or antigen-binding fragment thereof are each independently a murine-derived antibody, a chimeric antibody, a humanized antibody or a fully human antibody.

In some specific embodiments, the present disclosure provides an anti-TIGIT/anti-PD-L1 antibody, wherein the anti-TIGIT antibody or antigen-binding fragment thereof comprises a first heavy chain variable region and a first light chain variable region, wherein:

(1) the first heavy chain variable region has an amino acid sequence selected from the group consisting of:

(b1) amino acid sequences set forth in SEQ ID NO: 98 and SEQ ID NO: 99;

(b2) amino acid sequences derived from the amino acid sequences set forth in (b1) by substitution, deletion or addition of one or more amino acids and functionally identical or similar to the amino acid sequences set forth in (b1); and (b3) amino acid sequences having at least 80% sequence identity to the amino acid sequences set forth in (b1); and (2) the first light chain variable region has an amino acid sequence selected from the group consisting of:

(b4) amino acid sequences set forth in SEQ ID NO: 100 and SEQ ID NO: 101;

(b5) amino acid sequences derived from the amino acid sequences set forth in (b4) by substitution, deletion or addition of one or more amino acids and functionally identical or similar to the amino acid sequences set forth in (b4); and (b6) amino acid sequences having at least 80% sequence identity to the amino acid sequences set forth in (b4); and the anti-PD-L1 antibody or antigen-binding fragment thereof comprises a second heavy chain variable region and a second light chain variable region, wherein:

(1) the second heavy chain variable region has an amino acid sequence selected from the group consisting of:

(B1) amino acid sequences set forth in SEQ ID NO: 37, SEQ ID NO: 38, SEQ ID NO: 39, SEQ ID NO: 40, SEQ ID NO: 50, SEQ ID NO: 52 and SEQ ID NO: 61;

(B2) amino acid sequences derived from the amino acid sequences set forth in (B1) by substitution, deletion or addition of one or more amino acids and functionally identical or similar to the amino acid sequences set forth in (B1); and (B3) amino acid sequences having at least 80% sequence identity to the amino acid sequences set forth in (B1); and (2) the second light chain variable region has an amino acid sequence selected from the group consisting of:

(B4) amino acid sequences set forth in SEQ ID NO: 41, SEQ ID NO: 42, SEQ ID NO: 43, SEQ ID NO: 44, SEQ ID NO: 54, SEQ ID NO: 56 and SEQ ID NO: 64;

(B5) amino acid sequences derived from the amino acid sequences set forth in (B4) by substitution, deletion or addition of one or more amino acids and functionally identical or similar to the amino acid sequences set forth in (B4); and (B6) amino acid sequences having at least 80% sequence identity to the amino acid sequences set forth in (B4).

In some specific embodiments, the present disclosure provides an anti-TIGIT/anti-PD-L1 antibody, wherein the first heavy chain variable region has an amino acid sequence selected from the group consisting of: an amino sequence set forth in SEQ ID NO: 98, amino acid sequences derived from the amino acid sequence set forth in SEQ ID NO: 98 by substitution, deletion or addition of one or more amino acids and functionally identical to the amino acid sequence set forth in SEQ ID NO: 98, and amino acid sequences having at least 85% sequence identity to the amino acid sequence set forth in SEQ ID NO: 98, and the first light chain variable region has an amino acid sequence selected from the group consisting of: an amino sequence set forth in SEQ ID NO: 100, amino acid sequences derived from the amino acid sequence set forth in SEQ ID NO: 100 by substitution, deletion or addition of one or more amino acids and functionally identical to the amino acid sequence set forth in SEQ ID NO: 100, and amino acid sequences having at least 85% sequence identity to the amino acid sequence set forth in SEQ ID NO: 100.

In some specific embodiments, the present disclosure provides an anti-TIGIT/anti-PD-L1 antibody, wherein the first heavy chain variable region has an amino acid sequence selected from the group consisting of: an amino sequence set forth in SEQ ID NO: 98, amino acid sequences derived from the amino acid sequence set forth in SEQ ID NO: 98 by substitution, deletion or addition of one or more amino acids and functionally identical to the amino acid sequence set forth in SEQ ID NO: 98, and amino acid sequences comprising H1CDR1, H1CDR2 and H1CDR3 set forth in SEQ ID NOs: 25, 26 and 27 and having at least 85% sequence identity to the amino acid sequence set forth in SEQ ID NO: 98, and the first light chain variable region has an amino acid sequence selected from the group consisting of: an amino sequence set forth in SEQ ID NO: 100, amino acid sequences derived from the amino acid sequence set forth in SEQ ID NO: 100 by substitution, deletion or addition of one or more amino acids and functionally identical to the amino acid sequence set forth in SEQ ID NO: 100, and amino acid sequences comprising L1CDR1, L1CDR2 and L1CDR3 set forth in SEQ ID NOs: 31, 32 and 33 and having at least 85% sequence identity to the amino acid sequence set forth in SEQ ID NO: 100.

In some specific embodiments, for the anti-TIGIT/anti-PD-L1 antibody according to the present disclosure, the anti-TIGIT antibody or anti-PD-L1 antibody may be a murine-derived antibody, and further comprises a heavy chain constant region of murine-derived IgG1, IgG2a, IgG2b, IgG2c, IgG3 or a variant thereof, and a light chain constant region of murine-derived κ chain or a variant thereof.

In some preferred embodiments, for the anti-TIGIT/anti-PD-L1 antibody according to the present disclosure, the murine-derived anti-TIGIT antibody further comprises a heavy chain constant region of murine-derived IgG1, IgG2 or a variant thereof, and a light chain constant region of murine-derived κ chain or a variant thereof.

In some specific embodiments, the present disclosure provides an anti-TIGIT/anti-PD-L1 antibody, wherein the anti-TIGIT antibody or antigen-binding fragment thereof comprises a first heavy chain variable region and a first light chain variable region, wherein:

(1) the first heavy chain variable region has an amino acid sequence selected from the group consisting of:

(c1) an amino acid sequence set forth in SEQ ID NO: 99;

(c2) amino acid sequences derived from the amino acid sequence set forth in (c1) by substitution, deletion or addition of one or more amino acids and functionally identical or similar to the amino acid sequence set forth in (c1); and (c3) amino acid sequences having at least 80% sequence identity to the amino acid sequence set forth in (c1); and (2) the first light chain variable region has an amino acid sequence selected from the group consisting of:

(c4) an amino acid sequence set forth in SEQ ID NO: 101;

(c5) amino acid sequences derived from the amino acid sequence set forth in (c4) by substitution, deletion or addition of one or more amino acids and functionally identical or similar to the amino acid sequence set forth in (c4); and (c6) amino acid sequences having at least 80% sequence identity to the amino acid sequence set forth in (c4); and the anti-PD-L1 antibody or antigen-binding fragment thereof comprises a second heavy chain variable region and a second light chain variable region, wherein:

(1) the second heavy chain variable region has an amino acid sequence selected from the group consisting of:

(C1) amino acid sequences set forth in SEQ ID NO: 50, SEQ ID NO: 52 and SEQ ID NO: 61;

(C2) amino acid sequences derived from the amino acid sequences set forth in (C1) by substitution, deletion or addition of one or more amino acids and functionally identical or similar to the amino acid sequences set forth in (C1); and (C3) amino acid sequences having at least 80% sequence identity to the amino acid sequences set forth in (C1); and (2) the second light chain variable region has an amino acid sequence selected from the group consisting of:

(B4) amino acid sequences set forth in SEQ ID NO: 54, SEQ ID NO: 56 and SEQ ID NO: 64;

(C5) amino acid sequences derived from the amino acid sequences set forth in (C4) by substitution, deletion or addition of one or more amino acids and functionally identical or similar to the amino acid sequences set forth in (C4); and (C6) amino acid sequences having at least 80% sequence identity to the amino acid sequences set forth in (C4).

In some specific embodiments, the present disclosure provides an anti-TIGIT/anti-PD-L1 antibody, wherein the first heavy chain variable region has an amino acid sequence selected from the group consisting of: an amino sequence set forth in SEQ ID NO: 99, amino acid sequences derived from the amino acid sequence set forth in SEQ ID NO: 99 by substitution, deletion or addition of one or more amino acids and functionally identical to the amino acid sequence set forth in SEQ ID NO: 99, and amino acid sequences comprising H1CDR1, H1CDR2 and H1CDR3 set forth in SEQ ID NOs: 28, 29 and 30 and having at least 85% sequence identity to the amino acid sequence set forth in SEQ ID NO: 99, and the first light chain variable region has an amino acid sequence selected from the group consisting of: an amino sequence set forth in SEQ ID NO: 101, amino acid sequences derived from the amino acid sequence set forth in SEQ ID NO: 101 by substitution, deletion or addition of one or more amino acids and functionally identical to the amino acid sequence set forth in SEQ ID NO: 101, and amino acid sequences comprising L1CDR1, L1CDR2 and L1CDR3 set forth in SEQ ID NOs: 34, 35 and 36 and having at least 85% sequence identity to the amino acid sequence set forth in SEQ ID NO: 101; and the second heavy chain variable region has an amino acid sequence selected from the group consisting of: an amino sequence set forth in SEQ ID NO: 50, amino acid sequences derived from the amino acid sequence set forth in SEQ ID NO: 50 by substitution, deletion or addition of one or more amino acids and functionally identical to the amino acid sequence set forth in SEQ ID NO: 50, and amino acid sequences comprising H2CDR1, H2CDR2 and H2CDR3 set forth in SEQ ID NOs: 1, 2 and 3 and having at least 85% sequence identity to the amino acid sequence set forth in SEQ ID NO: 50, and the second light chain variable region has an amino acid sequence selected from the group consisting of: an amino sequence set forth in SEQ ID NO: 54, amino acid sequences derived from the amino acid sequence set forth in SEQ ID NO: 54 by substitution, deletion or addition of one or more amino acids and functionally identical to the amino acid sequence set forth in SEQ ID NO: 54, and amino acid sequences comprising L2CDR1, L2CDR2 and L2CDR3 set forth in SEQ ID NOs: 13, 14 and 15 and having at least 85% sequence identity to the amino acid sequence set forth in SEQ ID NO: 54.

In some specific embodiments, the present disclosure provides an anti-TIGIT/anti-PD-L1 antibody, wherein the first heavy chain variable region has an amino acid sequence selected from the group consisting of: an amino sequence set forth in SEQ ID NO: 99, amino acid sequences derived from the amino acid sequence set forth in SEQ ID NO: 99 by substitution, deletion or addition of one or more amino acids and functionally identical to the amino acid sequence set forth in SEQ ID NO: 99, and amino acid sequences comprising H1CDR1, H1CDR2 and H1CDR3 set forth in SEQ ID NOs: 28, 29 and 30 and having at least 85% sequence identity to the amino acid sequence set forth in SEQ ID NO: 99, and the first light chain variable region has an amino acid sequence selected from the group consisting of: an amino sequence set forth in SEQ ID NO: 101, amino acid sequences derived from the amino acid sequence set forth in SEQ ID NO: 101 by substitution, deletion or addition of one or more amino acids and functionally identical to the amino acid sequence set forth in SEQ ID NO: 101, and amino acid sequences comprising L1CDR1, L1CDR2 and L1CDR3 set forth in SEQ ID NOs: 34, 35 and 36 and having at least 85% sequence identity to the amino acid sequence set forth in SEQ ID NO: 101; and the second heavy chain variable region has an amino acid sequence selected from the group consisting of: an amino sequence set forth in SEQ ID NO: 52, amino acid sequences derived from the amino acid sequence set forth in SEQ ID NO: 52 by substitution, deletion or addition of one or more amino acids and functionally identical to the amino acid sequence set forth in SEQ ID NO: 52, and amino acid sequences comprising H2CDR1, H2CDR2 and H2CDR3 set forth in SEQ ID NOs: 1, 2 and 3 and having at least 85% sequence identity to the amino acid sequence set forth in SEQ ID NO: 52, and the second light chain variable region has an amino acid sequence selected from the group consisting of: an amino sequence set forth in SEQ ID NO: 56, amino acid sequences derived from the amino acid sequence set forth in SEQ ID NO: 56 by substitution, deletion or addition of one or more amino acids and functionally identical to the amino acid sequence set forth in SEQ ID NO: 56, and amino acid sequences comprising L2CDR1, L2CDR2 and L2CDR3 set forth in SEQ ID NOs: 13, 14 and 15 and having at least 85% sequence identity to the amino acid sequence set forth in SEQ ID NO: 56.

In some specific embodiments, the present disclosure provides an anti-TIGIT/anti-PD-L1 antibody, wherein the first heavy chain variable region has an amino acid sequence selected from the group consisting of: an amino sequence set forth in SEQ ID NO: 99, amino acid sequences derived from the amino acid sequence set forth in SEQ ID NO: 99 by substitution, deletion or addition of one or more amino acids and functionally identical to the amino acid sequence set forth in SEQ ID NO: 99, and amino acid sequences comprising H1CDR1, H1CDR2 and H1CDR3 set forth in SEQ ID NOs: 28, 29 and 30 and having at least 85% sequence identity to the amino acid sequence set forth in SEQ ID NO: 99, and the first light chain variable region has an amino acid sequence selected from the group consisting of: an amino sequence set forth in SEQ ID NO: 101, amino acid sequences derived from the amino acid sequence set forth in SEQ ID NO: 101 by substitution, deletion or addition of one or more amino acids and functionally identical to the amino acid sequence set forth in SEQ ID NO: 101, and amino acid sequences comprising L1CDR1, L1CDR2 and L1CDR3 set forth in SEQ ID NOs: 34, 35 and 36 and having at least 85% sequence identity to the amino acid sequence set forth in SEQ ID NO: 101; and the second heavy chain variable region has an amino acid sequence selected from the group consisting of: an amino sequence set forth in SEQ ID NO: 61, amino acid sequences derived from the amino acid sequence set forth in SEQ ID NO: 61 by substitution, deletion or addition of one or more amino acids and functionally identical to the amino acid sequence set forth in SEQ ID NO: 61, and amino acid sequences comprising H2CDR1, H2CDR2 and H2CDR3 set forth in SEQ ID NOs: 7, 8 and 9 and having at least 85% sequence identity to the amino acid sequence set forth in SEQ ID NO: 61, and the second light chain variable region has an amino acid sequence selected from the group consisting of: an amino sequence set forth in SEQ ID NO: 64, amino acid sequences derived from the amino acid sequence set forth in SEQ ID NO: 64 by substitution, deletion or addition of one or more amino acids and functionally identical to the amino acid sequence set forth in SEQ ID NO: 64, and amino acid sequences comprising L2CDR1, L2CDR2 and L2CDR3 set forth in SEQ ID NOs: 19, 20 and 21 and having at least 85% sequence identity to the amino acid sequence set forth in SEQ ID NO: 64.

In some preferred embodiments, the present disclosure provides an anti-TIGIT/anti-PD-L1 antibody, wherein the first heavy chain variable region has an amino acid sequence selected from the group consisting of: an amino sequence set forth in SEQ ID NO: 99, amino acid sequences derived from the amino acid sequence set forth in SEQ ID NO: 99 by substitution, deletion or addition of one or more amino acids and functionally identical to the amino acid sequence set forth in SEQ ID NO: 99, and amino acid sequences comprising H1CDR1, H1CDR2 and H1CDR3 set forth in SEQ ID NOs: 28, 29 and 30 and having at least 85%, or at least 90%, or at least 95%, or at least 98% sequence identity to the amino acid sequence set forth in SEQ ID NO: 99, and the first light chain variable region has an amino acid sequence selected from the group consisting of: an amino sequence set forth in SEQ ID NO: 101, amino acid sequences derived from the amino acid sequence set forth in SEQ ID NO: 101 by substitution, deletion or addition of one or more amino acids and functionally identical to the amino acid sequence set forth in SEQ ID NO: 101, and amino acid sequences comprising L1CDR1, L1CDR2 and L1CDR3 set forth in SEQ ID NOs: 34, 35 and 36 and having at least 85%, or at least 90%, or at least 95%, or at least 98% sequence identity to the amino acid sequence set forth in SEQ ID NO: 101; and the second heavy chain variable region has an amino acid sequence selected from the group consisting of: an amino sequence set forth in SEQ ID NO: 50, amino acid sequences derived from the amino acid sequence set forth in SEQ ID NO: 50 by substitution, deletion or addition of one or more amino acids and functionally identical to the amino acid sequence set forth in SEQ ID NO: 50, and amino acid sequences comprising H2CDR1, H2CDR2 and H2CDR3 set forth in SEQ ID NOs: 1, 2 and 3 and having at least 85%, or at least 90%, or at least 95%, or at least 98% sequence identity to the amino acid sequence set forth in SEQ ID NO: 50, and the second light chain variable region has an amino acid sequence selected from the group consisting of: an amino sequence set forth in SEQ ID NO: 54, amino acid sequences derived from the amino acid sequence set forth in SEQ ID NO: 54 by substitution, deletion or addition of one or more amino acids and functionally identical to the amino acid sequence set forth in SEQ ID NO: 54, and amino acid sequences comprising L2CDR1, L2CDR2 and L2CDR3 set forth in SEQ ID NOs: 13, 14 and 15 and having at least 85%, or at least 90%, or at least 95%, or at least 98% sequence identity to the amino acid sequence set forth in SEQ ID NO: 54.

In some specific embodiments, the present disclosure provides an anti-TIGIT/anti-PD-L1 antibody, wherein the first heavy chain variable region has an amino acid sequence selected from the group consisting of: an amino sequence set forth in SEQ ID NO: 99, amino acid sequences derived from the amino acid sequence set forth in SEQ ID NO: 99 by substitution, deletion or addition of one or more amino acids and functionally identical to the amino acid sequence set forth in SEQ ID NO: 99, and amino acid sequences comprising H1CDR1, H1CDR2 and H1CDR3 set forth in SEQ ID NOs: 28, 29 and 30 and having at least 85%, or at least 90%, or at least 95%, or at least 98% sequence identity to the amino acid sequence set forth in SEQ ID NO: 99, and the first light chain variable region has an amino acid sequence selected from the group consisting of: an amino sequence set forth in SEQ ID NO: 101, amino acid sequences derived from the amino acid sequence set forth in SEQ ID NO: 101 by substitution, deletion or addition of one or more amino acids and functionally identical to the amino acid sequence set forth in SEQ ID NO: 101, and amino acid sequences comprising L1CDR1, L1CDR2 and L1CDR3 set forth in SEQ ID NOs: 34, 35 and 36 and having at least 85%, or at least 90%, or at least 95%, or at least 98% sequence identity to the amino acid sequence set forth in SEQ ID NO: 101; and the second heavy chain variable region has an amino acid sequence selected from the group consisting of: an amino sequence set forth in SEQ ID NO: 52, amino acid sequences derived from the amino acid sequence set forth in SEQ ID NO: 52 by substitution, deletion or addition of one or more amino acids and functionally identical to the amino acid sequence set forth in SEQ ID NO: 52, and amino acid sequences comprising H2CDR1, H2CDR2 and H2CDR3 set forth in SEQ ID NOs: 1, 2 and 3 and having at least 85%, or at least 90%, or at least 95%, or at least 98% sequence identity to the amino acid sequence set forth in SEQ ID NO: 52, and the second light chain variable region has an amino acid sequence selected from the group consisting of: an amino sequence set forth in SEQ ID NO: 56, amino acid sequences derived from the amino acid sequence set forth in SEQ ID NO: 56 by substitution, deletion or addition of one or more amino acids and functionally identical to the amino acid sequence set forth in SEQ ID NO: 56, and amino acid sequences comprising L2CDR1, L2CDR2 and L2CDR3 set forth in SEQ ID NOs: 13, 14 and 15 and having at least 85%, or at least 90%, or at least 95%, or at least 98% sequence identity to the amino acid sequence set forth in SEQ ID NO: 56.

In some specific embodiments, the present disclosure provides an anti-TIGIT/anti-PD-L1 antibody, wherein the first heavy chain variable region has an amino acid sequence selected from the group consisting of: an amino sequence set forth in SEQ ID NO: 99, amino acid sequences derived from the amino acid sequence set forth in SEQ ID NO: 99 by substitution, deletion or addition of one or more amino acids and functionally identical to the amino acid sequence set forth in SEQ ID NO: 99, and amino acid sequences comprising H1CDR1, H1CDR2 and H1CDR3 set forth in SEQ ID NOs: 28, 29 and 30 and having at least 85%, or at least 90%, or at least 95%, or at least 98% sequence identity to the amino acid sequence set forth in SEQ ID NO: 99, and the first light chain variable region has an amino acid sequence selected from the group consisting of: an amino sequence set forth in SEQ ID NO: 101, amino acid sequences derived from the amino acid sequence set forth in SEQ ID NO: 101 by substitution, deletion or addition of one or more amino acids and functionally identical to the amino acid sequence set forth in SEQ ID NO: 101, and amino acid sequences comprising L1CDR1, L1CDR2 and L1CDR3 set forth in SEQ ID NOs: 34, 35 and 36 and having at least 85%, or at least 90%, or at least 95%, or at least 98% sequence identity to the amino acid sequence set forth in SEQ ID NO: 101; and the second heavy chain variable region has an amino acid sequence selected from the group consisting of: an amino sequence set forth in SEQ ID NO: 61, amino acid sequences derived from the amino acid sequence set forth in SEQ ID NO: 61 by substitution, deletion or addition of one or more amino acids and functionally identical to the amino acid sequence set forth in SEQ ID NO: 61, and amino acid sequences comprising H2CDR1, H2CDR2 and H2CDR3 set forth in SEQ ID NOs: 7, 8 and 9 and having at least 85%, or at least 90%, or at least 95%, or at least 98% sequence identity to the amino acid sequence set forth in SEQ ID NO: 61, and the second light chain variable region has an amino acid sequence selected from the group consisting of: an amino sequence set forth in SEQ ID NO: 64, amino acid sequences derived from the amino acid sequence set forth in SEQ ID NO: 64 by substitution, deletion or addition of one or more amino acids and functionally identical to the amino acid sequence set forth in SEQ ID NO: 64, and amino acid sequences comprising L2CDR1, L2CDR2 and L2CDR3 set forth in SEQ ID NOs: 19, 20 and 21 and having at least 85%, or at least 90%, or at least 95%, or at least 98% sequence identity to the amino acid sequence set forth in SEQ ID NO: 64. In some embodiments, the present disclosure provides a humanized anti-TIGIT/anti-PD-L1 antibody, wherein the heavy chain comprises a heavy chain constant region of human IgG1, IgG2, IgG3, IgG4 or a variant thereof, and the light chain comprises a light chain constant region of human κ, λ chain or a variant thereof.

In a preferred embodiment of the present disclosure, the murine-derived anti-TIGIT/anti-PD-L1 antibody may further comprise a light chain constant region of murine-derived κ, λ chain or a variant thereof, and/or further comprise a heavy chain constant region of murine-derived IgG1, IgG2a, IgG2b, IgG2c, IgG3 or a variant thereof.

In a preferred embodiment of the present disclosure, for the anti-TIGIT/anti-PD-L1 antibody according to the present disclosure, the antibody light chain of the anti-TIGIT antibody or antigen-binding fragment thereof further comprises a light chain constant region of murine-derived κ, λ chain or a mutant sequence thereof. The antibody heavy chain of the anti-TIGIT antibody or antigen-binding fragment thereof further comprises a heavy chain constant region of murine-derived IgG1, IgG2a, IgG2b, IgG2c, IgG3 or a mutant sequence thereof, preferably a heavy chain constant region of human IgG1, IgG2, or IgG4.

In some specific embodiments, for the anti-TIGIT/anti-PD-L1 antibody according to the present disclosure, the humanized anti-TIGIT antibody or antigen-binding fragment thereof further comprises a heavy chain constant region of human IgG1, IgG2a, IgG2b, IgG2c, IgG3 or a variant thereof, and a light chain constant region of human κ, λ chain or a variant thereof. In some preferred embodiments, the humanized anti-TIGIT antibody or antigen-binding fragment thereof of the present disclosure further comprises a heavy chain constant region of human IgG1, IgG2, IgG4 or a variant thereof, and a light chain constant region of human κ chain or a variant thereof.

In a preferred embodiment of the present disclosure, for the anti-TIGIT/anti-PD-L1 antibody according to the present disclosure, the antibody heavy chain of the anti-PD-L1 antibody or antigen-binding fragment thereof further comprises a heavy chain constant region of murine-derived IgG1, IgG2a, IgG2b, IgG2c, IgG3 or a mutant sequence thereof, preferably a heavy chain constant region of human IgG or a mutant sequence thereof; and the antibody light chain of the anti-PD-L1 antibody or antigen-binding fragment thereof further comprises a light chain constant region of murine-derived κ, λ chain or a mutant sequence thereof.

In some specific embodiments, for the anti-TIGIT/anti-PD-L1 antibody according to the present disclosure, the humanized anti-PD-L1 antibody or antigen-binding fragment thereof further comprises a heavy chain constant region of human IgG1, IgG2, IgG3 or IgG4 or a variant thereof, and a light chain constant region of human κ, λ chain or a variant thereof. In some preferred embodiments, the humanized anti-TIGIT antibody or antigen-binding fragment thereof of the present disclosure further comprises a heavy chain constant region of human IgG4 or a variant thereof, and a light chain constant region of human κ chain or a variant thereof.

In some embodiments, the present disclosure provides an anti-TIGIT/anti-PD-L1 antibody, wherein the anti-TIGIT antibody or antigen-binding fragment thereof and the anti-PD-L1 antibody or antigen-binding fragment thereof are Fab, Fv, sFv or $F(ab)_2$, respectively. In a specific embodiment, the anti-TIGIT/anti-PD-L1 antibody provided by the present disclosure is $scF(ab)_2$.

Preferably, the anti-TIGIT/anti-PD-L1 antibody in the above embodiments of the present disclosure is an anti-TIGIT/anti-PD-L1 bispecific antibody. In some embodiments, the bispecific antibody is a human antibody or a humanized antibody. In some embodiments, one of the binding sites is for TIGIT and the other is for any other antigen. In some embodiments, one of the binding sites is for TIGIT and the other is for PD-L1. In some embodiments, the bispecific antibody can bind to two different epitopes of TIGIT. The bispecific antibody can also be used to localize a cytotoxic agent to cells expressing TIGIT. These antibodies possess a TIGIT binding arm and a binding arm of a cytotoxic agent such as saporin, anti-interferon-α, *vinca* alkaloids, ricin A chain, methotrexate or radioisotope haptens. The bispecific antibody of the present disclosure may be prepared as a full-length antibody or an antibody fragment (e.g., $F(ab')_2$ bispecific antibody).

Methods for preparing bispecific antibodies are known in the art. Traditionally, the recombination and preparation of bispecific antibodies are based on the co-expression of two heavy chain-light chain pairs of immunoglobulin, where the two heavy chains have different specificities (Millstein and Cuello, Nature 305: 537 (1983)). Due to the random assortment of immunoglobulin heavy and light chains, the quadromas may produce a mixture of 10 different antibody molecules, only one of which has the correct bispecific structure. Purification of this correct molecule is usually carried out by an affinity chromatography, which is rather cumbersome and has low product yield. Similar methods are disclosed in WO93/08829 and Traunecker et al., EMBOJ. 10: 3655 (1991).

According to a different method, an antibody variable region with the desired binding specificities (antibody-antigen binding sites) is fused to an immunoglobulin constant region. In some embodiments, it is fused to an immunoglobulin heavy chain constant region comprising at least a portion of the hinge region, CH2 and CH3 regions. In some embodiments, the first heavy chain constant region (CH1) comprising the site necessary for binding to the light chain is present in at least a portion of the fusion. The DNA encoding the fusion fragment of the immunoglobulin heavy chain and, if desired, the immunoglobulin light chain, is inserted into separate expression vectors and co-transfected into a suitable host organism. This provides great flexibility for adjusting the mutual ratios of the three polypeptide fragments in embodiments where unequal ratios of the three polypeptide chains used in the construction provide optimal yields. However, it is possible to insert the coding sequences for two or all three polypeptide chains into one expression vector when at least two polypeptide chains are expressed in equal ratios to produce high yields or when the ratios are not of particular interest.

In one embodiment, the bispecific antibody is comprised of a hybrid immunoglobulin heavy chain with a first binding site in one arm and a hybrid immunoglobulin heavy chain-light chain pair in the other arm (providing a second binding site). Since the presence of the immunoglobulin light chain in only one half of the bispecific molecule provides a convenient separation route, this asymmetric structure facilitates separation of the desired bispecific material from the undesired immunoglobulin chain composition. This method is disclosed in WO 94/04690. For further information on the production of bispecific antibodies, reference could be made to, e.g., Suresh et al., Methods in Enzymology 121: 210 (1986).

According to another method, the interface between a pair of antibody molecules may be engineered to maximize the percentage of heterodimers recovered from recombinant cell culture. The interface comprises at least a portion of the CH3 domain of the antibody constant region. In this method, one or more small amino acids on the side chain at the interface of the first antibody molecule are replaced with big amino acids (e.g., tyrosine or tryptophan). By replacing big amino acids on the side chain with smaller amino acids (e.g., alanine or threonine), a compensatory "hole" of the same or similar size as the large side chain is created at the interface of the second antibody molecule. This provides a mechanism for increasing the yield of heterodimers other than other undesired end products such as homodimers.

Bispecific antibodies include cross-linked or "heteroconjugated" antibodies. For example, a heteroconjugated antibody may be conjugated to avidin and the other heteroconjugated antibody may be conjugated to biotin. Heteroconjugated antibodies can be prepared using any convenient cross-linking method. Suitable crosslinking agents are well known in the art and disclosed in U.S. Pat. No. 4,676,980, along with a number of crosslinking techniques.

The bispecific antibody of the present disclosure may be produced from antibody fragments. For example, bispecific antibodies may be prepared using chemical ligation techniques. Brennan et al., Science 229: 81 (1985) describes the proteolytic cleavage of intact antibodies to generate $F(ab')_2$ fragments. These fragments are decomposed in the presence of a dithiol complexing agent sodium arsenite (to stabilize adjacent dithiols and prevent the formation of intermolecular disulfide bonds). The resulting Fab' fragments are then converted into thionitrobenzoate (TNB) derivatives. One of the Fab'-TNB derivatives was then reconverted to Fab'-thiol by reduction with mercaptoethylamine and mixed with an equimolar amount of the other Fab'-TNB derivative to form a bispecific antibody.

Fab'-SH fragments may be recovered directly from *E. coli* and these fragments may be chemically coupled to form a bispecific antibody. Shalaby et al., J. Exp. Med. 175: 217-225 (1992) describes the generation of fully humanized bispecific antibody $F(ab')_2$ molecules. Each Fab' fragment is secreted separately from *E. coli* and subjected to targeting chemical coupling in vitro to form a bispecific antibody.

In some embodiments, the bispecific antibody fragments of the present disclosure may be produced and isolated directly from recombinant cell culture. For example, bispecific antibodies may be produced using leucine zippers (Kostelny et al., J. Immunol. 148(5): 1547-1553 (1992)). Leucine zipper peptides from Fos and Jun proteins were linked to the Fab' portions of two different antibodies by genetic fusion. Antibody homodimers are decomposed at the hinge region to form monomers, which are then reoxidized to form antibody heterodimers. This method can also be used to produce antibody homodimers. Diabody technology provides additional mechanisms for preparing bispecific antibody fragments. The bispecific antibody fragment comprises a heavy chain variable region (VH) and a light chain variable region (VL) joined by a linker that is too short to allow pairing between the two domains on the same chain. Thus, the VH and VL domains on one fragment are forced to pair with the complementary VL and VH domains on the other fragment, thereby forming two antigen binding sites. In another embodiment, bispecific antibody fragments may be constructed by using single-chain Fv(sFv) dimers.

The present disclosure encompasses multi-specific antibodies with more than two binding sites. For example, trispecific antibodies may be prepared. Multi-specific antibodies may be assimilated (and/or dissimilated) more rapidly than bispecific antibodies by cells expressing the antigens to which the antibody binds. The antibody of the present disclosure may be a multi-specific antibody (e.g., a tetravalent antibody) having three or more antigen binding sites that can be readily produced by recombinant expression of nucleic acids encoding antibody polypeptide chains. Multi-specific antibodies may contain a dimerization domain and three or more antigen binding sites. In some embodiments, the dimerization domain comprises (or consists of) an Fc region or a hinge region. In such case, the antibody will comprise an Fc region and three or more antigen binding sites amino-terminal to the Fe region. In some embodiments, the multi-specific antibody comprises (or consists of) three to about eight antigen binding sites. In some embodiments, the multi-specific antibody comprises four antigen binding sites. Multi-specific antibodies comprise at least one polypeptide chain (e.g., two polypeptide chains), wherein the polypeptide chains comprise two or more variable regions. The multi-specific antibody of the present disclosure may further comprise at least two (e.g., four) light chain variable region polypeptides. The multi-specific antibody of the present disclosure may comprise, for example, about two to about eight light chain variable region polypeptides. The light chain variable region polypeptide of the present disclosure comprises a light chain variable region, and optionally, further comprises a CL domain.

In a bispecific antibody comprising a TIGIT targeting moiety and a PD-L1 targeting moiety, one of the TIGIT targeting moiety and the PD-L1 targeting moiety may be a full-length antibody, and the other may be an antigen binding fragment (e.g., scFv) comprising heavy chain CDRs, light chain CDRs or a combination thereof. A full-length antibody targeting one of the TIGIT and PD-L1 proteins and an antigen-binding fragment targeting the other protein can be linked directly or chemically (e.g., covalently) via a peptide linker. The antigen-binding fragment (e.g., scFv) can be linked directly or via a peptide linker to the N-terminal of the full-length antibody (e.g., the N-terminal of the light or heavy chain of the full-length antibody), the C-terminal of the full-length antibody (e.g., the C-terminal of the heavy chain (or Fc or CH3 domain) of the full-length antibody), or both.

In one embodiment, the bispecific antibody may comprise a full-length anti-TIGIT antibody, an antigen-binding fragment of an anti-PD-L1 antibody (e.g., scFab, scFv), and a peptide linker between them. In other embodiments, the bispecific antibody may comprise a full-length anti-TIGIT antibody, an antigen-binding fragment of an anti-PD-L1 antibody (e.g., scFab, scFv), and a peptide linker between them.

In one embodiment, the scFv of the bispecific antibody may comprise a heavy chain variable region and a light chain variable region in any order. For example, the scFv of the bispecific antibody may comprise a heavy chain variable region and a light chain variable region in the direction from the N-terminal to the C-terminal, and optionally a peptide linker between them, or alternatively, the scFv of the bispecific antibody may comprise a light chain variable region and a heavy chain variable region in the direction from the N-terminal to the C-terminal, and optionally a peptide linker between them.

In some embodiments, the peptide linker may comprise, for example, Gly, Asn, and/or Ser residues, and may further comprise neutral amino acids, such as Thr and/or Ala. Amino acid sequences suitable for a peptide linker may be those known in the art. Meanwhile, the length of the peptide linker may be determined differently within such limits that the function of the fusion protein is not affected. For example, the peptide linker may include a total of about 1 to about 100, about 2 to about 50, or about 5 to about 25 residues selected from the group consisting of Gly, Asn, Ser, Thr, and Ala. In one embodiment, the peptide linker may be represented as $(G_mS_l)_n$ (m, l and n are independently integers from about 1 to about 10, particularly from about 2 to about 5).

In another embodiment, the PD-L1 targeting moiety and the TIGIT targeting moiety may both be full-length antibodies or antigen-binding fragments comprising heavy chain CDRs, light chain CDRs, or a combination thereof.

In another embodiment, the bispecific antibody may be in the form of a heterodimer comprising a first arm and a second arm, where the first arm comprises a pair of a first heavy chain and a first light chain targeting one of TIGIT and PD-L1, and the second arm comprises a pair of a second heavy chain and a second light chain targeting the other.

In one embodiment, the full-length antibody may be in the form of a full-length immunoglobulin (e.g., IgG, IgM, IgA, IgE, or IgD, such as human IgG, human IgM, human IgA, human IgE, or human IgD), and the antigen-binding fragment may be selected from the group consisting of Fab, Fab', $F(ab')_2$, Fd, Fv, scFv, scFab, single chain antibody, sdFv and the like. For example, the full-length antibody may be in the form of a full-length human IgG (human IgG1, human IgG2, human IgG3 or human IgG4), and the antigen-binding fragment may be scFv.

For example, the antibody described herein may contain a flexible linker sequence, or may be modified to add functional moieties (e.g., PEG, drugs, toxins, or labels). In some specific embodiments, for the anti-TIGIT/anti-PD-L1 bispecific antibody according to the present disclosure, the anti-TIGIT antibody or antigen-binding fragment thereof has a structure of (VL-CL)-peptide linker-(VH)-IgG4CH, and the anti-PD-L1 antibody or antigen-binding fragment thereof has a structure of (VL-CL)-peptide linker-(VH)-IgG4CH. In some other specific embodiments, for the anti-TIGIT/anti-PD-L1 bispecific antibody according to the present disclosure, the anti-TIGIT antibody or antigen-binding fragment thereof has a structure of (VL-VH)-peptide linker-IgG4FC, and the anti-PD-L1 antibody or antigen-binding fragment thereof has a structure of (VL-CL)-peptide linker-(VH)-IgG4CH. In some specific embodiments, the peptide linker is in the form of (GGGGS (SEQ ID NO: 112))n, wherein n is 1-12, preferably 3-10, more preferably 6-8, e.g. 6, 7, or 8 GGGGS (SEQ ID NO: 112) repeats. In some other specific embodiments, the IgG4FC in the (VL-CL)-peptide linker-(VH)-IgG4CH targeting the TIGIT moiety is an IgG4 CH fragment containing mutations S228P and L235E, and the IgG4FC in the (VL-CL)-peptide linker-(VH)-IgG4CH targeting the PD-L1 moiety is an IgG4 CH fragment containing mutations S228P and L235E. In some other specific embodiments, the IgG4FC in the (VL-CL)-peptide linker-(VH)-IgG4CH targeting the TIGIT moiety is an IgG4 CH fragment containing mutations S228P, S354C and T366W to form a “Hole” structure, and the IgG4FC in the (VL-CL)-peptide linker-(VH)-IgG4CH targeting the PD-L1 moiety is an IgG4 CH fragment containing mutations S228P, Y349C, T366S, L368A, and Y407V to form a “Knob” structure. In some other specific embodiments, the IgG4FC in the (VL-CL)-peptide linker-(VH)-IgG4CH targeting the TIGIT moiety is an IgG4 CH fragment containing mutations S228P, L235E, S354C, and T366W to form a “Hole” structure, and the IgG4FC in the (VL-CL)-peptide linker-(VH)-IgG4CH targeting the PD-L1 moiety is an IgG4 CH fragment containing mutations S228P, L235E, Y349C, T366S, L368A, and Y407V to form a “Knob” structure. In some specific embodiments, the anti-TIGIT/anti-PD-L1 bispecific antibody according to the present disclosure consists of two peptide chains, wherein:

peptide chain 1 has a structure as shown in FIG. 3A, and peptide chain 2 has a structure as shown in FIG. 3B; and wherein, IgG4CH/Ks represents the IgG4 constant region with mutations S228P, Y349C, T366S, L368A, and Y407V, and IgG4CH/Hs represents the IgG4 constant region with mutations S228P, S354C, and T366W.

In some other specific embodiments, the anti-TIGIT/anti-PD-L1 bispecific antibody according to the present disclosure consists of two peptide chains, wherein:

peptide chain 1 has a structure as shown in FIG. 4A, and peptide chain 2 has a structure as shown in FIG. 4B; and wherein, IgG4CH/PE represents the IgG4 constant region (mutations S228P and L235E).

In some specific embodiments, the anti-TIGIT/anti-PD-L1 bispecific antibody according to the present disclosure consists of two peptide chains, wherein peptide chain 1 has an amino acid sequence set forth in SEQ ID NO: 102, and peptide chain 2 has an amino acid sequence set forth in SEQ ID NO: 103. In some other specific embodiments, the anti-TIGIT/anti-PD-L1 bispecific antibody according to the present disclosure consists of two peptide chains, wherein peptide chain 1 has an amino acid sequence set forth in SEQ ID NO: 104, and peptide chain 2 has an amino acid sequence set forth in SEQ ID NO: 105. In some other specific embodiments, the anti-TIGIT/anti-PD-L1 bispecific antibody according to the present disclosure consists of two peptide chains, wherein peptide chain 1 has an amino acid sequence set forth in SEQ ID NO: 102, and peptide chain 2 has an amino acid sequence set forth in SEQ ID NO: 106. In some other specific embodiments, the anti-TIGIT/anti-PD-L1 bispecific antibody according to the present disclosure consists of two peptide chains, wherein peptide chain 1 has an amino acid sequence set forth in SEQ ID NO: 107, and peptide chain 2 has an amino acid sequence set forth in SEQ ID NO: 108. In some other specific embodiments, the anti-TIGIT/anti-PD-L1 bispecific antibody according to the present disclosure consists of two peptide chains, wherein peptide chain 1 has an amino acid sequence set forth in SEQ ID NO: 102, and peptide chain 2 has an amino acid sequence set forth in SEQ ID NO: 109. In some other specific embodiments, the anti-TIGIT/anti-PD-L1 bispecific antibody according to the present disclosure consists of two peptide chains, wherein peptide chain 1 has an amino acid sequence set forth in SEQ ID NO: 110, and peptide chain 2 has an amino acid sequence set forth in SEQ ID NO: 111. Another aspect of the present disclosure provides an isolated nucleic acid. In some embodiments, the isolated nucleic acid according to the present disclosure encodes the anti-TIGIT/anti-PD-L1 antibody of the present disclosure. In some embodiments, the isolated nucleic acid according to the present disclosure encodes the anti-TIGIT antibody or antigen-binding fragment thereof of the present disclosure. In some other embodiments, the isolated nucleic acid according to the present disclosure encodes the anti-PD-L1 antibody or antigen-binding fragment thereof of the present disclosure.

In a specific embodiment, the isolated nucleic acid according to the present disclosure comprises a nucleotide sequence encoding the first heavy chain variable region set forth in SEQ ID NO: 75, SEQ ID NO: 76, SEQ ID NO: 98 or SEQ ID NO: 99, and a nucleotide sequence encoding the first light chain variable region set forth in SEQ ID NO: 77, SEQ ID NO: 78, SEQ ID NO: 100 or SEQ ID NO: 101. In another specific embodiment, the isolated nucleic acid according to the present disclosure comprises a nucleotide sequence encoding the second heavy chain variable region set forth in SEQ ID NO: 50, SEQ ID NO: 52 or SEQ ID NO: 61, and a nucleotide sequence encoding the second light chain variable region set forth in SEQ ID NO: 54, SEQ ID NO: 56 or SEQ ID NO: 64. In another specific embodiment, the isolated nucleic acid according to the present disclosure comprises the isolated nucleic acid according to the present disclosure comprises a nucleotide sequence encoding the first heavy chain variable region set forth in SEQ ID NO: 99, and a nucleotide sequence encoding the first light chain variable region set forth in SEQ ID NO: 101. In another specific embodiment, the isolated nucleic acid according to the present disclosure comprises a nucleotide sequence encoding the second heavy chain variable region set forth in SEQ ID NO: 50, and a nucleotide sequence encoding the second light chain variable region set forth in SEQ ID NO: 54. In a specific embodiment, the isolated nucleic acid combination according to the present disclosure comprises a nucleotide sequence encoding the first heavy chain variable region set forth in SEQ ID NO: 99, a nucleotide sequence encoding the first light chain variable region set forth in SEQ ID NO: 101, a nucleotide sequence encoding the second heavy chain variable region set forth in SEQ ID NO: 50, and a nucleotide sequence encoding the second light chain variable region set forth in SEQ ID NO: 54. In another specific embodiment, the isolated nucleic acid combination according to the present disclosure comprises a nucleotide sequence encoding the first heavy chain variable region set forth in SEQ ID NO: 99, a nucleotide sequence encoding the first light chain variable region set forth in SEQ ID NO: 101, a nucleotide sequence encoding the second heavy chain variable region set forth in SEQ ID NO: 52, and a nucleotide sequence encoding the second light chain variable region set forth in SEQ ID NO: 56. In another specific embodiment, the isolated nucleic acid combination according to the present disclosure comprises a nucleotide sequence encoding the first heavy chain variable region set forth in SEQ ID NO: 99, a nucleotide sequence encoding the first light chain variable region set forth in SEQ ID NO: 101, a nucleotide sequence encoding the second heavy chain variable region set forth in SEQ ID NO: 61, and a nucleotide sequence encoding the second light chain variable region set forth in SEQ ID NO: 64.

Another aspect of the present disclosure provides an expression vector. In some embodiments, the expression vector of the present disclosure expresses the anti-TIGIT/anti-PD-L1 bispecific antibody of the present disclosure. In some embodiments, the expression vectors of the present disclosure express the anti-TIGIT antibody or antigen-binding fragment thereof of the present disclosure. In some other embodiments, the expression vector of the present disclosure expresses the anti-PD-L1 antibody or antigen-binding fragment thereof of the present disclosure. In some embodiments, for the expression vector according to the present disclosure, the vector expressing the anti-TIGIT antibody or antigen-binding fragment thereof of the present disclosure and the vector expressing the anti-PD-L1 antibody or antigen-binding fragment thereof of the present disclosure are the same expression vector. The expression vector according to the present disclosure comprises the isolated nucleic acid molecule of the present disclosure.

Another aspect of the present disclosure provides a host cell transformed with the above expression vector.

In some embodiments, the host cell according to the present disclosure is selected from the group consisting of prokaryotic cells and eukaryotic cells. In some embodiments, the host cell is bacteria, preferably *Escherichia coli*. In another preferred embodiment, the host cell is a mammalian cell.

Another aspect of the present disclosure provides a method for producing the anti-TIGIT/anti-PD-L1 bispecific antibody of the present disclosure, comprising expressing the antibody in the host cell and isolating the antibody from the host cell.

Another aspect of the present disclosure provides a pharmaceutical composition, comprising the anti-TIGIT/anti-PD-L1 bispecific antibody of the present disclosure and a pharmaceutically acceptable carrier. In some embodiments, the present disclosure provides a pharmaceutical composition comprising the anti-TIGIT/anti-PD-L1 bispecific antibody of the present disclosure, and additional active components, such as other antibodies, targeted drugs, and the like. In some embodiments, the pharmaceutically acceptable carrier is selected from the group consisting of antioxidants, polypeptides, proteins, hydrophilic polymers, amino acids, saccharides, chelating agents, alditols, ions, and surfactants. In a specific embodiment, the pharmaceutically acceptable carrier is a buffered aqueous solution. In another specific embodiment, the pharmaceutically acceptable carrier is in the form of liposomes.

Another aspect of the present disclosure provides a chimeric antigen receptor (CAR) fusion protein comprising the anti-TIGIT antibody or antigen-binding fragment thereof and/or anti-PD-L1 antibody or antigen-binding fragment thereof of the present disclosure. In some embodiments, the chimeric antigen receptor fusion protein comprises the anti-TIGIT antibody or antigen-binding fragment thereof of the present disclosure, which is a single-chain variable fragment (scFv) of $V_H$ and $V_L$ against TIGIT antigen. In some other embodiments, the chimeric antigen receptor fusion protein comprises the anti-PD-L1 antibody or antigen-binding fragment thereof of the present disclosure, which is a single-chain variable fragment (scFv) of $V_H$ and $V_L$ against PD-L1 antigen. In some other embodiments, the chimeric antigen receptor fusion protein comprises a first single-chain variable fragment (scFv) of $V_H$ and $V_L$ against TIGIT antigen and a second single-chain variable fragment (scFv) of $V_H$ and $V_L$ against PD-L1 antigen. The first scFv of $V_H$ and $V_L$ against TIGIT antigen comprises H1CDR1, H1CDR2 and H1CDR3 of the first heavy chain variable region and L1CDR1, L1CDR2 and L1CDR3 of the first light chain variable region as described in the above embodiments. The second scFv of $V_H$ and $V_L$ against PD-L1 antigen comprises H2CDR1, H2CDR2 and H2CDR3 of the second heavy chain variable region and L2CDR1, L2CDR2 and L2CDR3 of the second light chain variable region as described in the above embodiments.

The anti-TIGIT/anti-PD-L1 bispecific antibody of the present disclosure may be combined with a pharmaceutically acceptable carrier, diluent or excipient to prepare a pharmaceutical preparation suitable for oral or parenteral administration. The routes of administration include, but are not limited to oral, intradermal, intramuscular, intraperitoneal, intravenous, intracerebral, intraocular, intratracheal, subcutaneous, and intranasal routes. The preparation may be administered by any means, for example, by infusion or bolus injection, by the means of absorption through epithelium or skin mucosa (for example, oral mucosa or rectum, etc.). Administration can be systemic or local. The preparation can be prepared by methods known in the art, and contains a carrier, diluent or excipient conventionally used in the field of pharmaceutical preparations.

Another aspect of the present disclosure provides a method for treating and/or preventing a disease associated with TIGIT, PD-L1, or both. The method comprises administering to a subject in need thereof the anti-TIGIT/anti-PD-L1 bispecific antibody of the present disclosure or the pharmaceutical composition of the present disclosure.

Another aspect of the present disclosure provides use of the anti-TIGIT/anti-PD-L1 bispecific antibody or the pharmaceutical composition of the present disclosure in the manufacture of a medicament for treating and/or preventing a disease associated with TIGIT, PD-L1 or both. In some embodiments, the disease associated with TIGIT, PD-L1, or both includes hematological tumor, lymphoma, breast cancer, lung cancer, gastric cancer, intestinal cancer, esophageal cancer, ovarian cancer, cervical cancer, kidney cancer, bladder cancer, pancreatic cancer, glioma and/or melanoma. The tumor may be any type of tumor that expresses PD-L1 protein, such as bladder cancer, liver cancer, colon cancer, rectal cancer, endometrial cancer, leukemia, lymphoma, pancreatic cancer, lung cancer (e.g., small cell lung cancer, non-small cell lung cancer, etc.), breast cancer, urethral cancer, head and neck cancer, gastrointestinal cancer, gastric cancer, esophageal cancer, ovarian cancer, kidney cancer, melanoma, prostate cancer, thyroid cancer, etc. The tumor may be a primary or metastatic tumor. In some embodiments, the present disclosure provides use of the above anti-TIGIT/anti-PD-L1 bispecific antibody or the pharmaceutical composition of the present disclosure in the manufacture of anti-tumor drugs. For example, the tumor is selected from the group consisting of hematological tumor, lymphoma, breast cancer, lung cancer, gastric cancer, intestinal cancer, esophageal cancer, ovarian cancer, cervical cancer, kidney cancer, bladder cancer, pancreatic cancer, glioma, melanoma, myeloma, and prostate cancer.

The anti-TIGIT/anti-PD-L1 bispecific antibody provided by the present disclosure has a significant anti-tumor effect and can significantly inhibit tumor growth, which can be used in the manufacture of medicaments for the treatment of various tumors with broad market prospects.

Definitions

Unless otherwise defined, the meanings of scientific and technical terms used herein are those commonly understood by those skilled in the art. The nomenclature and techniques used in cell and tissue culture, molecular biology, as well as protein and oligo/polynucleotide chemistry and hybridization described herein are well known and commonly used in the art. Standard techniques are used for recombinant DNA, oligonucleotide synthesis, tissue culture and transformation (e.g. electroporation, lipofection). The enzymatic reaction and purification techniques are carried out according to the manufacturer's instructions or methods commonly used in the art or described herein. The aforementioned techniques and methods are generally used according to what's well known in the art and what's described in the multiple comprehensive and more specific documents cited and discussed in this specification. Reference could be made to, Sambrook et al., Molecular Cloning: A Laboratory Manual (2nd edition, Cold Spring Harbor Laboratory Press, Cold Spring Harbor, New York (1989)). The nomenclature as well as laboratory methods and techniques used in analytical chemistry, synthetic organic chemistry, and medical and pharmaceutical chemistry described herein are well known and commonly used in the art.

In the present disclosure, the term "at least 80% sequence identity" refers to at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity. In the present disclosure, the term "at least 85% sequence identity" refers to at least 85%, 86%, 87%, 88%, 89%, 90%, 91%, 92%, 93%, 94%, 95%, 96%, 97%, 98%, 99%, or 100% sequence identity. In some preferred embodiments, the sequence identity described in the present disclosure may be at least 90%, 91%, 92%, 93%, 94%, 95%, 96%, 97%, 98%, 99%, or 100%. Sequence comparison and determination of identity percentage between two sequences may be performed by the BLASTN/BLASTP algorithm on the website of National Center for Biotechnology Institute.

In an antibody molecule, three hypervariable regions of the light chain and three hypervariable regions of the heavy chain are arranged relative to each other in a three-dimensional space to form an antigen-binding surface. The antigen-binding surface is complementary to the three-dimensional surface of the bound antigen, and the three hypervariable regions of each heavy chain and light chain are referred as "complementarity determining region" or "CDR". The assignment of amino acids to each domain is defined by Kabat "Sequences of Proteins of Immunological Interest" (National Institutes of Health, Bethesda, Maryland (1987 and 1991)) or Chothia and Lesk (J. Mol. Biol. 196: 901-917 (1987), Chothia et al., Nature 342: 878-883 (1989)).

The "antibody" of the present disclosure refers to a polypeptide or a polypeptide complex that specifically recognizes and binds to an antigen. The antibody may be an intact antibody and any antigen-binding fragments or single chains thereof. The "antibody" of the present disclosure includes any protein or peptide containing at least a portion of an Ig molecule that has the biological activity of binding to an antigen. Examples of the "antibody" of the present disclosure include, but are not limited to, heavy or light chain CDRs or ligand binding portions thereof, heavy or light chain variable regions, heavy or light chain constant regions, framework regions, or any portion thereof.

The "antigen-binding fragment" of the present disclosure includes the following fragment with antigen-binding activity: Fab fragment, Fab' fragment, $F(ab')_2$ fragment, and Fv fragment and scFv fragment that bind to human TIGIT or PD-L1. The Fv fragment comprises a first heavy chain variable region and a first light chain variable region of the antibody but no constant region, and it is the smallest antibody fragment with all antigen binding sites. Generally, Fv antibody further comprises a polypeptide linker between the VH and VL domains, and is able to form the structure required for antigen binding. Different linkers may also be utilized to link the two variable regions of antibody to form a polypeptide chain, which is called single-chain antibody or single-chain Fv (scFv). The anti-TIGIT or anti-PD-L1 antibody of the present disclosure may be a single-chain variable fragment (scFv), which is derived from the single-chain polypeptide of an antibody and retains the ability to bind to antigen. Examples of scFv include antibody polypeptides generated by recombinant DNA techniques in which the Fv regions of immunoglobulin heavy chain (H chain) and light chain (L chain) fragments are linked via a spacer sequence. Various methods for preparing scFv are well known to those skilled in the art.

The antibody of the present disclosure refers to an immunoglobulin molecule or an immunologically active part thereof, i.e., a molecule that contains antigen-binding sites that specifically bind to the antigen (through immunological reaction). "Specific binding" means that an antibody reacts with one or more antigenic determinants of an antigen but does not react with other polypeptides, or it binds to other polypeptides with very low affinity ($Kd>10^{-6}$). Antibodies include but are not limited to polyclonal, monoclonal, chimeric, dAb (domain antibody), single chain, Fab, Fab' and $F(ab')_2$ fragment, Fv, scFv and Fab expression library. A monoclonal antibody (mAb) is the antibody obtained from a single cloned cell line, and the cell line is not limited to eukaryotic, prokaryotic or phage cloned cell lines. A monoclonal antibody or antigen-binding fragment thereof can be obtained by recombination using, for example, hybridoma technology, recombination technology, phage display technology, and synthesis technology such as CDR grafting, or other existing technology.

The "murine-derived antibody" of the present disclosure is a monoclonal antibody against human TIGIT produced according to the knowledge and skills in the art. During the production, the test subject is injected with the TIGIT antigen, and then the hybridomas expressing the antibody with the desired sequence or functional property are isolated.

The "chimeric antibody" of the present disclosure is an antibody formed by fusing the variable regions of a murine-derived antibody with the constant regions of a human antibody, which can reduce the immune response induced by the murine-derived antibody. To establish a chimeric antibody, it is necessary to establish a hybridoma secreting murine-derived specific monoclonal antibodies first, clone the variable region genes from the mouse hybridoma cells, and then clone the constant region genes of the human antibody as needed, and chimeric genes formed by linking the mouse variable region with the human constant region genes are inserted into a human vector. Finally, the chimeric antibody is expressed in a eukaryotic system or a prokaryotic system.

The "humanized antibody" of the present disclosure is also called a CDR grafted antibody, which is an antibody produced by grafting mouse CDR sequences into the framework (FR) of a human antibody. Such framework sequences of variable region may be obtained from public DNA databases or public references, for example, from the ImMunoGeneTics (IMGT) website http: //imgt.cines.fr or from the Journal of Immunoglobulin, 2001ISBN012441351.

The "bispecific antibody" as used herein refers to a monoclonal antibody that has binding sites for at least two different antigens.

The "peptide linker" as used herein may be those comprising any amino acid from 1 to 10, especially 2 to 50, and may comprise any kind of amino acids without any limitation.

BRIEF DESCRIPTION OF DRAWINGS

FIG. 3A shows a schematic diagram of the structure of the peptide chain 1 and FIG. 3B shows the structure of the peptide chain 2 of the bispecific anti-TIGIT/anti-PD-L1 antibody in some embodiments.

FIG. 4A shows a schematic diagram of the structure of the peptide chain 1 and FIG. 4B shows the structure of the peptide chain 2 of the bispecific anti-TIGIT/anti-PD-L1 antibody in some embodiments.

DETAILED DESCRIPTION

Figure 1:
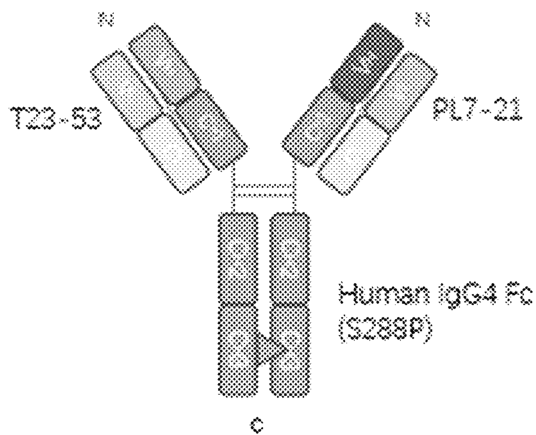
FIG. 1 shows a schematic diagram of the structure of the bispecific anti-TIGIT/anti-PD-L1 antibody with a ScFab structure.

The following representative examples are used to illustrate the present disclosure better, rather than to limit the scope of protection of the present disclosure. The experimental methods without conditions indicated in the following examples are usually carried out according to conventional conditions, such as the antibody technology experiment manual and molecular cloning manual of Cold Spring Harbor, or according to the conditions recommended by the raw material or commodity manufacturers. The materials and reagents used in the examples are all commercially available unless otherwise specified.

Example 1 Preparation of Anti-Human PD-L1 Antibody

1. Animal Immunization

Experimental BALB/c and SJL mice and SD rats were immunized with mFc-tagged PD-L1 antigen protein (purchased from Beijing Acrobiosystems Co., Ltd., China) together with adjuvants.

The immune adjuvant was Freund's Adjuvant, Complete (SIGMA, F5881-10ML) for the first time, and Freund's Adjuvant, Incomplete (SIGMA, F5506-10ML) later. Different tagged PD-L1 antigen protein samples were added dropwise to the adjuvant solution with vortex to mix thoroughly. The dosages of the adjuvant were referred to the instructions. After the mixture was mixed well and formed a water-in-oil emulsion, the mice or rats were immunized. The immunization protocol is shown in Table 1:

TABLE 1

Immunization protocol

| Group | Strain | Antigen | Adjuvant | Dosage | Route* |
|---|---|---|---|---|---|
| 1 | BALB/c | PBS | None | | |
| 2 | BALB/c | PD-L1-mFc | Freund's Adjuvant, Complete (First time) | 50 μg | i.m. |
| | | | Freund's Adjuvant, Incomplete | 25 μg | |
| 3 | SJL | PBS | None | | |
| 4 | SJL | PD-L1-mFc | Freund's Adjuvant, Complete (First time) | 50 μg | i.m. |
| | | | Freund's Adjuvant, Incomplete | 25 μg | |
| 5 | SD | PBS | None | | |
| 6 | SD | PD-L1-mFc | Freund's Adjuvant, Complete (First time) | 100 μg | i.m. |
| | | | Freund's Adjuvant, Incomplete | 50 μg | |

*i.m.: intramuscular injection

2. Cell Fusion

The mouse spleen was aseptically removed and prepared into a cell suspension, and the cells were fused at the ratio of spleen cells: Sp2/0 cells (mouse myeloma cells)=1:1. The fused cell suspension was transferred to 15 mL RPMI 1640 complete medium containing 20% FBS and then left at room temperature for 20 min. The fused cells were resuspended with RPMI 1640 medium containing 1×HAT, 1×BIOMYC3, and 20% FBS. The cell suspension was added to several 96-well cell culture plates at 100 μL/well to ensure a cell volume per well of about $4\times10^4$ cells/well, and the plates were placed in a 37° C. cell incubator. After 5 days, additional 100 μL of RPMI 1640 complete medium containing 20% FBS, 1×HAT, and 1×BIOMYC-3 was added to each well.

3. Screening of Positive Clones

After one week of fusion, the cell supernatant was collected. The hybridoma parent clones with binding and blocking abilities were screened by ELISA, expanded, tested for binding and blocking activities, and screened again for hybridoma positive cell lines with binding and blocking abilities. The positive cell lines were subcloned by the limiting dilution method, and after one week of culture, the activities of binding to PD-L1 molecules and blocking the interaction of PD-L1/PD-1 of the subcloned supernatant were detected by ELISA. Four preferable cell strains that showed positive results in the above two tests, PL-7, PL-15, PL-16 and PL-18, were selected.

4. Acquisition of Variable Region Sequences of Anti-PD-L1 Antibodies

The subcloned positive hybridoma cells were expanded, and an appropriate amount of cells was used for total RNA extraction according to the instructions of RNeasy Plus Mini Kit (Qiagen, 74134). The first strand of cDNA was synthesized using Prime Script 1st strand cDNA Synthesis Kit (Takara, 6110A).

Specific primers were designed according to the variable region of the mouse antibody subtype, and 5' end of the primers contained the homologous arm sequence for homologous recombination with the eukaryotic expression vector. PCR amplification for the variable region of antibodies was performed using cDNA as a template to obtain the gene fragments of the light chain variable region and heavy chain variable region of the mouse antibody, named SHS009PL-7, SHS009PL-15, SHS009PL-16 and SHS009PL-18, respectively. The design of primers refers to references: 1. Anke Krebber, Susanne Bornhauser, Jorg Burmester et al. Reliable cloning of functional antibody variable domains from hybridomas and spleen cell repertoires employing a reengineered phage display system. Journal of Immunological Methods, 1997, 201: 35-55; 2. Simon KorenMiha KosmačAnja Colja Venturini et al. Antibody variable-region sequencing as a method for hybridoma cell-line authentication, 2008, 78: 1071-1078. DNA sequencing was performed and the results are shown in Table 2.

TABLE 2

Sequences of murine-derived anti-PD-L1 monoclonal antibodies

| Antibody | Amino acid sequence of heavy chain variable region | Amino acid sequence of light chain variable region | H2CDR1, H2CDR2, H2CDR3 | L2CDR1, L2CDR2, L2CDR3 |
|---|---|---|---|---|
| SHS009PL-7 | SEQ ID NO: 37 | SEQ ID NO: 41 | SEQ ID NOs: 1, 2, 3 | SEQ ID NOs: 13, 14, 15 |
| SHS009PL-15 | SEQ ID NO: 38 | SEQ ID NO: 42 | SEQ ID NOs: 4, 5, 6 | SEQ ID NOs: 16, 17, 18 |
| SHS009PL-16 | SEQ ID NO: 39 | SEQ ID NO: 43 | SEQ ID NOs: 7, 8, 9 | SEQ ID NOs: 19, 20, 21 |
| SHS009PL-18 | SEQ ID NO: 40 | SEQ ID NO: 44 | SEQ ID NOs: 10, 11, 12 | SEQ ID NOs: 22, 23, 24 |

5. Construction of Chimeric Antibodies

The purified gene fragments of the light chain and the heavy chain variable regions of the mouse antibodies were respectively co-transformed into *Escherichia coli* DH5a competent cells with the linearized eukaryotic expression plasmid containing the light chain constant region or the heavy chain constant region of human antibodies. The chimeric antibodies with correct sequences were selected and named PL-7CHI, PL-15CHI, PL-16CHI and PL-18CHI. The sequencing results of the chimeric antibodies are shown in Table 3.

The amino acid sequences of VL and VH of PL-7CHI, PL-15CHI, PL-16CHI and PL-18CHI are identical to those of the murine-derived antibodies SHS009PL-7, SHS009PL-15, SHS009PL-16 and SHS009PL-18, respectively.

The plasmids for light and heavy chains of chimeric antibodies were transfected into HEK 293F cells, and the antibodies were expressed and purified. The purity, activity and affinity were tested and analyzed.

TABLE 3

Sequences of chimeric anti-PD-L1 antibodies

| Chimeric antibody | Amino acid sequence of heavy chain variable region | Amino acid sequence of light chain variable region |
|---|---|---|
| PL-7CHI | SEQ ID NO: 37 | SEQ ID NO: 41 |
| PL-15CHI | SEQ ID NO: 38 | SEQ ID NO: 42 |
| PL-16CHI | SEQ ID NO: 39 | SEQ ID NO: 43 |
| PL-18CHI | SEQ ID NO: 40 | SEQ ID NO: 44 |

6. Humanization of Anti-PD-L1 Antibodies

Based on the results of activity analysis and affinity KD value of chimeric antibodies, PL-7CHI and PL-16CHI were modified to humanized antibodies.

The humanization of murine-derived monoclonal chimeric antibodies PL-7CHI and PL-16CHI was carried out with reference to the classic CDR transplantation strategy. With the framework region sequence FR1-FR3 of antibodies PL-7CHI and PL-16CHI as templates, full human framework regions with similar 3D structure but low immunogenicity were screened in the human framework region library to replace FR1-FR3 sequence of PL-7CHI and PL-16CHI. After homology comparison, it was found that the FR region sequences of the heavy chain variable region of the antibodies PL-7CHI and PL-16CHI were the most similar to the human antibody germline genes M99683|IGHV4-31*02 (SEQ ID NO: 45) and X62109|IGHV1-3*01 (SEQ ID NO: 46), respectively; and the FR region sequences of the light chain variable region of the antibodies PL-7CHI and PL-16CHI were the most similar to the human antibody germline gene Z00023|IGKV4-1*01 (SEQ ID NO: 47). The full-length sequences of the humanized heavy/light chain were 3D modeled and compared structurally with the heavy/light chain sequences of the original antibodies. The antigenicity and 3D structural similarity were considered comprehensively, and the amino acids that were shown to play a key role in the structural stability of the antibody in the structural simulation were back mutated to murine-derived amino acid residues. Finally, 5 humanized heavy chains (the humanized heavy chain variable region sequences of PL-7CHI: VH1-0 (SEQ ID NO: 48), VH1-1 (SEQ ID NO: 49, VH1-2 (SEQ ID NO: 50), VH1-3 (SEQ ID NO: 51) or VH1-4 (SEQ ID NO: 52)) and 4 humanized light chains (the humanized light chain variable region sequences of PL-7CHI: VL1-0 (SEQ ID NO: 53), VL1-1 (SEQ ID NO: 54), VL1-2 (SEQ ID NO: 55) or VL1-3 (SEQ ID NO: 56)) of PL-7CHI were obtained; and 5 humanized heavy chains (the humanized heavy chain variable region sequences of PL-16CHI: VH1-0 (SEQ ID NO: 57), VH1-1 (SEQ ID NO: 58), VH1-2 (SEQ ID NO: 59), VH1-3 (SEQ ID NO: 60) or VH1-4 (SEQ ID NO: 61)) and 3 humanized light chains (the humanized light chain variable region sequences of PL-16CHI: VL1-0 (SEQ ID NO: 62), VL1-1 (SEQ ID NO: 63) or VL1-2 (SEQ ID NO: 64)) of PL-16CHI were obtained. On this basis, multiple humanized antibodies were obtained through different combinations of light and heavy chains. After activity detection, it was determined that the anti-PD-L1 humanized antibodies with the highest scores were HuPL7-21 and HuPL16-42.

Example 2 Production of Humanized Anti-PD-L1 Antibody

Corresponding polynucleotides were synthesized based on the amino acid sequences of the light chain and heavy chain variable region of humanized antibodies obtained above, and oligonucleotide fragments containing complementary sequences between adjacent fragments were synthesized. The oligonucleotide fragments were annealed and assembled by Overlap PCR. Then nucleotide fragments encoding the entire light chain and heavy chain variable regions were amplified by specific primers (5' end contained the homologous arm sequence for homologous recombination with the eukaryotic expression vector). The purified nucleotide fragments of the light chain variable region were co-transformed into *Escherichia coli* DH5a competent cells with the linearized eukaryotic expression plasmid containing light chain constant region of IgG4. The purified nucleotide fragments of the heavy chain variable region were co-transformed into *Escherichia coli* DH5a competent cells with the eukaryotic expression plasmid containing heavy chain constant region of IgG4 containing S228P/L235E mutation. The competent cells with the transformed plasmids were spread evenly on the surface of the agar plates containing the corresponding antibiotics. The agar plates were incubated in a 37° C. constant temperature incubator overnight, and then several single colonies were picked out for DNA sequencing.

The positive clones with correct sequences were subjected to plasmid extraction to obtain the expression plasmids for the light chain and the heavy chain of humanized antibodies. The concentration and purity of the plasmids were detected by a nucleic acid quantitative analyzer.

The plasmids were transfected into HEK293 F cells, and a large number of antibodies were expressed and purified. The purity, activity and affinity were tested and analyzed. The sequences are shown in Table 4.

TABLE 4

Sequences of humanized anti-PD-L1 antibodies

| Humanized antibody | Amino acid sequence of heavy chain variable region | Amino acid sequence of light chain variable region | H2CDR1, H2CDR2, H2CDR3 | L2CDR1, L2CDR2, L2CDR3 |
|---|---|---|---|---|
| HuPL7-21 | SEQ ID NO: 50 | SEQ ID NO: 54 | SEQ ID NOs: 1, 2 and 3 | SEQ ID NOs: 13, 14, 15 |
| HuPL16-42 | SEQ ID NO: 61 | SEQ ID NO: 64 | SEQ ID NOs: 7, 8 and 9 | SEQ ID NOs: 19, 20, 21 |

Example 3 Preparation of TIGIT Antibody-Related Antigen Protein and Positive Control Antibody 1. Construction of Expression Vector of Antigen Protein and Positive Control Antibody (1) Construction of Expression Vector of Antigen Protein The amino acid sequence of the extracellular region of human TIGIT protein and the amino acid sequence of hIgG1-Fc or mIgG1-Fc tag were designed as shown in SEQ ID NO: 65 and SEQ ID NO: 66, respectively. After codon optimization of the above amino acid sequences, the tagged extracellular region of TIGIT protein coding fragments TIGIT-hFc and TIGIT-mFc were synthesized and cloned into the eukaryotic expression plasmid pHR respectively to obtain the expression plasmid pHR-TIGIT-hFc and pHR-TIGIT-mFc.

The amino acid sequence of the extracellular region of human TIGIT protein was fused with his amino acid sequence, and the designed amino acid sequence is shown in SEQ ID NO: 67.

After codon optimization of the amino acid sequence, a complete expression plasmid pcDNA3.1-TIGIT-his was synthesized.

2) Construction of Expression Vector of Ligand Protein

The amino acid sequence of the extracellular region of human CD155 protein and the amino acid sequence of hIgG1-Fc or mIgG1-Fc tag were designed as shown in SEQ ID NO: 68 and SEQ ID NO: 69, respectively. After codon optimization of the above amino acid sequences, the tagged extracellular region of CD155 protein coding fragments CD155-hFc and CD155-mFc were synthesized and cloned into the eukaryotic expression plasmid pHR respectively to obtain the expression plasmid pHR-CD155-hFc and pHR-CD155-mFc.

The amino acid sequence of the extracellular region of human CD155 protein was fused with his amino acid sequence, and the designed amino acid sequence is shown in SEQ ID NO: 70. After codon optimization of the amino acid sequence, a complete expression plasmid pcDNA3.1(+)-CD155-his was synthesized.

3) Construction of Expression Vector of Positive Control Antibody

The humanized antibody 22G2 (abbreviated as 22G2 hereinafter) disclosed in the patent application US 2016/0176963A1 was used as a positive control antibody. 22G2 was prepared according to the method disclosed in US 2016/0176963A1. The amino acid sequence of 22G2 is as follows:

- the amino acid sequence of the heavy chain variable region of 22G2 is shown in SEQ ID NO: 71;
- the amino acid sequence of the light chain variable region of 22G2 is shown in SEQ ID NO: 72;

The amino acid sequence of antibody 22G2 was subjected to codon optimization. The heavy chain fragment was cloned into the eukaryotic expression plasmid pHR containing the light chain constant region of IgG4 to obtain the heavy chain eukaryotic expression plasmid pHR-22G2-hG4, and the light chain expression plasmid was pHR-22G2-hk.

2. Expression and Purification of Antigen Protein and Positive Control Antibody

1) Construction of Stable Transgenic Cell Line of Antigen Protein

A gene fragment encoding the full-length TIGIT protein was synthesized, with an amino acid sequence designed as shown in SEQ ID NO: 73, and then cloned into the eukaryotic expression plasmid pTargeT to obtain the expression plasmid pTargeT-TIGIT.

CHO-K1 cells (Shanghai Institute of Biochemistry and Cell Biology, Chinese Academy of Sciences) were electrotransfected with eukaryotic expression plasmid pTargeT-TIGIT under a square pulse of 15 msec at a voltage of 160 V and then cultured in an incubator at 37° C. with 5% $CO_2$. After 24 h, the cells were subjected to selection with culture medium containing 500 μg/mL G418. After 16 days, the positive rate of cell pool was detected by FACS. The cells electrotransfected with plasmid were plated ($1\times10^6$ cells/mL of cell density, 100 μL/well), and incubated with PE mouse anti-human TIGIT antibody (BD, 556046). Flow cytometer (BD, FACSJazz) was used to read the mean value at a wavelength of 585 nm, and data analysis was performed using GraphPad. The positive cell lines were subcloned, and a CHO-K1 cell line was selected, which expressed TIGIT at a high level and was named hTIGIT-CHO-K1.

2) Construction of Stable Transgenic Cell Line of Ligand Protein

A gene fragment encoding the full-length CD155 protein was synthesized, with an amino acid sequence designed as shown in SEQ ID NO: 74, and then cloned into the eukaryotic expression plasmid pTargeT to obtain the expression plasmid pTargeT-CD155.

CHO-K1 cells (Shanghai Institute of Biochemistry and Cell Biology, Chinese Academy of Sciences) were electrotransfected with eukaryotic expression plasmid pTargeT-CD155 under a square pulse of 15 msec at a voltage of 160 V and then cultured in an incubator at 37° C. with 5% $CO_2$. After 24 h, the cells were subjected to selection with culture medium containing 500 μg/mL G418. After 16 days, the positive rate of cell pool was detected by FACS. The cells electrotransfected with plasmid were plated ($1\times10^6$ cells/mL of cell density, 100 L/well), and incubated with PE mouse anti-human CD155 antibody (BD, 556046). Flow cytometer (BD, FACSJazz) was used to read the mean value at a wavelength of 585 nm, and data analysis was performed using GraphPad. The positive cell lines were subcloned, and a CHO-K1 cell line was selected, which expressed CD155 at a high level and was named hCD155-CHO-K1

3) Expression of Tagged Protein and Positive Control Antibody 293F cells were inoculated into a 1 L cell culture flask at a density of $0.5\times10^6$ cells/mL. Fresh and pre-warmed FreeStyle 293 expression medium was added to make the total volume 250 mL. The cells were cultured in a humidified $CO_2$ incubator at 37° C. with 8% $CO_2$ overnight. 500 μL of 1 mg/mL PEI solution was added to 8.5 mL FreeStyle 293 expression medium and mixed well. 250 μg of plasmid to be transfected was added to 8.5 mL of FreeStyle 293 expression medium and mixed well, wherein, the plasmids encoding tagged antigen protein, pHR-TIGIT-hFc, pHR-TIGIT-his, and pcDNA3.1(+)-TPA-TIGIT-mIgG1-Fc, were transfected respectively. The heavy chain plasmid pHR-22G2-hG4 and the light chain plasmid pHR-22G2-hk of positive control antibody 22G2 were co-transfected. The FreeStyle 293 expression medium containing PEI was added to the expression medium containing plasmids and mixed well, then the mixture was added to the cells, and the cells were cultured in a humidified $CO_2$ incubator at 37° C. with 8% $CO_2$. The cells were fed on the 1st and 3rd day after cell transfection with 2.5 mL of 200 mM glutamine and 5 mL of 180 g/L glucose per flask. The cell culture supernatant was collected when the cell viability dropped to 65%-75%. The cell culture was centrifuged at 1,500 rpm for 5 min to collect the supernatant. The supernatants were centrifuged at 8,000 rpm for 20 min to collect the supernatant again 4) Affinity Chromatography Purification Different affinity chromatography columns were used to perform purification by using AKTA machine (GE, AKTA pure-150) according to the properties of the proteins (see Table 5 for affinity chromatography columns suitable for different proteins). The specific purification steps are as follows.

TABLE 5

Affinity chromatography columns suitable for different proteins

| Protein | Column | Brand | Model |
|---|---|---|---|
| Murine monoclonal antibody (hybridoma)/ TIGIT-mFc/CD155-mFc | Protein G prepacked column | Bestchrom | Ezfast Protein G/4FF |
| TIGIT-his/CD155-His | NI prepacked column | GE | His Trap, HP/5 mL |
| TIGIT-hFc/CD155-hFc/ chimeric antibody, humanized antibody | Protein A prepacked column | GE | Hi Trap, Mabselect SuRe/5 mL |
| | Protein A self-packed column | GE | Mabselect LX/ 18 mL |

Cleaning: The equipment and pipelines were cleaned with ultrapure water for 2 min with a flow rate of 10 mL/min, and then the chromatography system was cleaned with 0.1 M NaOH;

Column connection: The chromatography column was connected to the chromatography equipment, rinsed with ultrapure water for 5 min, and then rinsed with 0.1 M NaOH for 30 min with a retention time of 5 min;

Equilibration: Five CVs (column volume) of 20 mM PB+0.15 M NaCl (pH 7.2) was used to equilibrate the column;

Sample loading: The supernatant from cell culture was loaded to the column with a retention time of 5 min;

Post-equilibration: Five CVs of 20 mM PB+0.15 M NaCl (pH 7.2) was used to equilibrate the column;

Elution: Elution was performed with 50 mM acetic acid (pH=3.4), for a retention time of 5 min. Collection was started when UV280 reached about 50 mAu, and stopped when UV280 dropped to about 50 mAu. The sample was adjusted to the pH of 7.0 with 1 M Tris-HCl (pH 9.0);

Re-equilibration: Three CVs of 20 mM PB+0.15 M NaCl (pH 7.2) was used for equilibration with a retention time of 5 min;

On-column cleaning: Cleaning was performed with 0.1 M NaOH for 30 min with a retention time of 5 min;

Cleaning and preservation: Cleaning was performed with purified water for 10 min, and then 2 CVs of 20% ethanol.

Example 4 Preparation of Anti-TIGIT Monoclonal Antibodies

1. Preparation of Hybridomas (1) Animal Immunization

The experimental C57 and SJL mice were immunized with purchased different tagged TIGIT antigen proteins (TIGIT-His (Sino Biological, 10917-H08H), TIGIT-hFc (R & D, 7898-TG), TIGIT-mFc (Acro Biosystems, Cat. No. TIT-H5253)) together with adjuvants. 50 g of antigen was used for the first shoot, and 25 μg of antigen was used for the subsequent immunization. The experimental SD rats were immunized with different tagged TIGIT antigen proteins together with adjuvants. 100 μg of antigen was used for the first shoot, and 50 μg of antigen was used for the subsequent immunization.

The immune adjuvant may be QuickAntibody-Mouse5W (Beijing Biodragon immunotech. Co., Ltd.), TiterMax (Sigma), CpG (GenScript Biotechnology Co., Ltd.), or Alum (thermo) adjuvant. Different tagged TIGIT protein samples were added dropwise to the adjuvant solution with vortex to mix thoroughly. The dosages of the adjuvant used were referred to the instructions. After the mixture was mixed well and formed a water-in-oil emulsion, the mice and rats were immunized.

Cell lines expressing high level of TIGIT, such as hTIGIT-CHO-K1, were also used to immunize rats to produce antibodies. The cultured hTIGIT-CHO-K1 positive cells obtained in Example 1 were treated with trypsin and then centrifuged at 1,000 rpm for 5 min. The supernatant was discarded and the cell pellets were resuspended in PBS. Part of the cell sample was taken out for cell counting, and the remaining cell sample was centrifuged at 1,000 rpm for 5 min. The supernatant was discarded and the cell pellet was resuspended in PBS. An appropriate amount of PBS was added to obtain a cell suspension of $1\times10^8$ cells/mL. Each mouse in the experimental group was immunized with $1\times10^7$ cells.

The immunization protocol is shown in Table 6 and Table 7:

TABLE 6

Mouse immunization protocol

| Group | Antigen | Adjuvant | Route* | Strain |
|---|---|---|---|---|
| 1 | PBS | None | i.p. | C57/SJL |
| 2 | TIGIT-His | Freund's adjuvant | i.p./s.c. | C57 |
| 3 | TIGIT-His | Titermax/cpg + Alum | s.c./i.m. | C57 |

TABLE 6-continued

| Mouse immunization protocol | | | | |
|---|---|---|---|---|
| Group | Antigen | Adjuvant | Route* | Strain |
| 4 | TIGIT-His | Titermax/cpg + Alum | s.c./i.m. | SJL |
| 5 | TIGIT-mFc | Titermax/cpg + Alum | s.c./i.m. | SJL |
| 6 | TIGIT-hFc | Freund's adjuvant | i.p./s.c. | C57 |

TABLE 7

| Rat immunization protocol | | | | |
|---|---|---|---|---|
| Group | Antigen | Adjuvant | Route* | Strain |
| 1 | PBS | None | i.p. | SD |
| 2 | TIGIT-His | Quick 5W | i.m. | SD |
| 3 | TIGIT-mFc | Quick 5W | i.m. | SD |
| 4 | hTIGIT-CHO-K1 | None | i.p. | SD |

*i.m. intramuscular injection;
s.c. subcutaneous injection;
i.p. intraperitoneal injection.

(2) Hybridoma Fusion

Acquisition and preparation of spleen cells. The mice/rats after booster immunization were sacrificed and soaked in 75% alcohol. The spleen was dissected out, ground with a grinding rod, and filtered through a cell strainer to prepare a single cell suspension. The spleen cell suspension was centrifuged at 2,000 rpm for 5 min, and the supernatant was discarded. 2 mL of red blood cell lysate was added to lyse red blood cells at room temperature for 2 min and PBS was added to reach 20 mL. After centrifugation at 1,500 rpm for 7 min, the supernatant was discarded. Viable cells were counted after resuspension. The Sp2/0 cells in the culture flask were collected, and after centrifugation at 1,000 rpm for 5 min, the supernatant was discarded. Viable cells were counted after resuspension. The spleen cells were mixed with Sp2/0 cells at a ratio of 1:1 and subjected to centrifugation at 1,500 rpm for 7 min, and the supernatant was discarded. The cells were resuspended in 20 mL electroporation buffer. After centrifugation at 1,500 rpm for 7 min, the supernatant was discarded and the step was repeated once. The cells were resuspended with an appropriate amount of electroporation buffer to ensure the cell concentration of about $2\times10^7$ cells/mL. The cell suspension was added to a 9 mL electroporation tank for fusion. After fusion, the cell suspension was transferred to 15 mL of RPMI 1640 complete medium containing 20% FBS and then left at room temperature for 20 min. The fused cells were resuspended with RPMI 1640 medium containing 1×HAT, 1×BIOMYC-3, and 20% FBS. The cell suspension was added to several 96-well cell culture plates at 100 μL/well to ensure that the cell volume per well was about $4\times10^4$ cells/well, and the plates were placed in a 37° C. cell incubator. After 5 days, additional 100 μL of RPMI 1640 complete medium containing 20% FBS, 1×HAT, and 1×BIOMYC-3 was added to each well.

(3) Screening of Hybridoma and Subcloning Supernatant

Primary screening: After one week of fusion, the supernatants of culture were collected and used for screening the hybridoma supernatants that can bind to TIGIT-his protein or TIGIT on cell surface by ELISA. TIGIT-his was used to screen for antibodies against TIGIT instead of hFc and mFc. The ability of the hybridoma supernatant to block the TIGIT-CD155 interaction was analyzed by ELISA. CD155-hFc was coated on ELISA plates. The mixture of recombinant humanized TIGIT-mFc and hybridoma supernatant was added for 2 h of incubation. HRP-labeled anti mouse IgG Fc specific antibody (Jackson Immuno Research) was added for 1 h of incubation. Microplate reader was used to detect absorbance at 450 nm.

Re-test: The hybridoma parent clones showing binding and blocking activities in the screening experiments were expanded. The binding activity was tested again by ELISA. The hybridoma supernatants that can bind to TIGIT on the surface of hTIGIT-CHO-K1 cells were screened by FACS. The hybridoma supernatants that can bind to the cyno-TIGIT-his protein were screened by ELISA. The hybridoma supernatants that showed crossed positive results in the three experiments were used as candidate positive clones.

The positive cell lines were subcloned by the limiting dilution method. After one week of culture, the binding activity to TIGIT and the activity of blocking the TIGIT-CD155 interaction of the supernatants were detected by ELISA. Five cell lines that showed positive results in the above two tests were obtained, respectively named as SHS006-17 and SHS006-23.

2. Preparation of Monoclonal Antibodies

According to the activity analysis results of the supernatants from subcloned cell culture, the parent clones of monoclonal antibodies SHS006-17 and SHS006-23 were identified and expanded. The culture medium was 1640 medium containing 10% fetal bovine serum, 1×NAEE, lx sodium pyruvate, and 1% penicillin-streptomycin double antibiotics. When the cell confluence was >80%, the cells were subcultured and expanded. When the cells were culture to about 50 mL, the supernatant was collected, and the antibody was purified. The obtained antibody was subjected to SDS-PAGE gel electrophoresis, which showed a good purity.

3. Sequencing of Monoclonal Antibodies

The subcloned positive hybridomas were expanded, and an appropriate amount of cells was used for total RNA extraction according to the instructions of RNeasy Plus Mini Kit (Qiagen, 74134). The first strand of cDNA was synthesized using Prime Script 1st strand cDNA Synthesis Kit (Takara, 6110A).

Specific primers were designed according to the variable region of the rat antibody subtype, and 5' end of the primers contained the homologous arm sequence for homologous recombination with the eukaryotic expression vector. PCR amplification for the variable region of antibodies was performed using cDNA as a template to obtain the gene fragments of the light chain variable region and heavy chain variable region of the rat antibody respectively. The design of primers refers to references: 1. Anke Krebber, Susanne Bornhauser, Jorg Burmester et al. Reliable cloning of functional antibody variable domains from hybridomas and spleen cell repertoires employing a reengineered phage display system. Journal of Immunological Methods, 1997, 201: 35-55; 2. Simon KorenMiha KosmačAnja Colja Venturini et al. Antibody variable-region sequencing as a method for hybridoma cell-line authentication, 2008, 78: 1071-1078. DNA sequencing was performed and the results are shown in Table 8.

TABLE 8

| Sequences of murine-derived anti-TIGIT monoclonal antibodies | | | | |
|---|---|---|---|---|
| Antibody | Amino acid sequence of heavy chain variable region | Amino acid sequence of light chain variable region | H1CDR1, H1CDR2, H1CDR3 | L1CDR1, L1CDR2, L1CDR3 |
| SHS006-17 | SEQ ID NO: 75 | SEQ ID NO: 77 | SEQ ID NOs: 25, 26, 27 | SEQ ID NOs: 31, 32, 33 |
| SHS006-23 | SEQ ID NO: 76 | SEQ ID NO: 78 | SEQ ID NOs: 28, 29, 30 | SEQ ID NOs: 34, 35, 36 |

Example 5 Construction of Chimeric Anti-TIGIT Antibodies

The purified gene fragments of the light chain and the heavy chain variable regions of the murine-derived antibody (see Example 3 for the purification steps) were respectively co-transformed into *Escherichia coli* DH5a competent cells with the linearized eukaryotic expression plasmid containing the light chain constant region or the heavy chain constant region of the human antibody. The mixture was spread evenly on the surface of the agar plates containing the corresponding antibiotics. The agar plates were incubated in a 37° C. constant temperature incubator overnight, and then several single colonies were selected for DNA sequencing. The chimeric antibodies with correct sequences were named SHS006-17CHI and SHS006-23CHI.

The positive clones with correct sequences were inoculated in 2×YT liquid medium containing the corresponding antibiotics and cultured at 37° C. for more than 12 h with shaking. The bacterial cells were collected for plasmid extraction to obtain the expression plasmids for the light chain and the heavy chain of the chimeric antibody. The concentration and purity of the plasmids were detected by a nucleic acid quantitative analyzer.

The plasmids for chimeric antibodies were transfected into HEK293E cells, and a large number of antibodies were expressed and purified. The purity, activity and affinity were tested and analyzed.

The chimeric antibody sequencing results are shown in Table 9.

TABLE 9

| Sequences of chimeric anti-TIGIT antibodies | | |
|---|---|---|
| Chimeric Antibody | Amino acid sequence of heavy chain variable region | Amino acid sequence of light chain variable region |
| SHS006-17 CHI | SEQ ID NO: 75 | SEQ ID NO: 77 |
| SHS006-23 CHI | SEQ ID NO: 76 | SEQ ID NO: 78 |

Example 6 Construction and Production of Humanized Anti-TIGIT Antibodies

Based on the results of activity analysis and affinity KD value of chimeric antibodies, SHS006-17CHI and SHS006-23CHI were modified to humanized antibodies.

To construct the humanized antibodies, the variable regions of antibodies SHS006-17CHI and SHS006-23CHI were compared with the mouse antibody sequences in the ImMunoGeneTics (IMGT) to determine their murine-derived germlines. After homology comparison, it was found that the FR region sequences of the heavy chain variable region of antibodies SHS006-17CHI and SHS006-23CHI were the most similar to mouse antibody germline genes IGHV2-26*01 and IGHV3-7*01 respectively; the FR sequences of the light chain variable region of the antibodies were the most similar to the mouse antibody germline genes IGKV2-28*01 and IGKV1-39*01, respectively. With the framework region sequence FR1-FR3 of antibody SHS006-17CHI/SHS006-23CHI as a template, full human framework regions with similar 3D structure but low immunogenicity were screened in the human framework region library to replace FR1-FR3 sequence of SHS006-17CHI/SHS006-23CHI. The full-length sequences of the heavy/light chain were 3D modeled and compared structurally with the heavy/light chain sequences of the original antibodies. Considering the antigenicity and 3D structural similarity, the amino acid sites that were shown to play a key role in the stability of antibody structures in structural simulations were mutated back to murine-derived amino acid residues. 5 humanized heavy chain variable regions (see SEQ ID NOs: 79, 80, 81, 82, and 83) and 4 humanized light chain variable regions (see SEQ ID NOs: 84, 85, 86, and 87) of SHS006-17CHI, and 5 humanized heavy chain variable regions (see SEQ ID NOs: 88, 89, 90, 91, and 92) and 5 humanized light chain variable regions (see SEQ ID NOs: 93, 94, 95, 96, and 97) of SHS006-23CHI were ultimately selected for further optimization. More than 95% of non-CDR regions of SHS006-17CHI or SHS006-23CHI antibody were humanized.

The amino acid sequences of the light chain and heavy chain variable region of humanized antibody obtained above were reversely transcribed into their corresponding nucleotide sequences, and oligonucleotide fragments containing complementary sequences between adjacent fragments were generated. The oligonucleotide fragments were annealed and assembled by Overlap PCR. Then nucleotide fragments of the entire light chain and heavy chain variable regions were amplified using specific primers (5' end contained the homologous arm sequence for homologous recombination with the eukaryotic expression vector). The purified nucleotide fragments of the light chain variable region were co-transformed into *Escherichia coli* DH5a competent cells with the linearized eukaryotic expression plasmid containing light chain constant region of IgG4. The purified nucleotide fragments of the heavy chain variable region were co-transformed into *Escherichia coli* DH5a competent cells with the eukaryotic expression plasmid containing heavy chain constant region of IgG4 containing S228P/L235E mutation. The competent cells with the transformed plasmid were spread evenly on the surface of the agar plates containing the corresponding antibiotics. The agar plates were incubated in a 37° C. constant temperature incubator overnight, and then several single colonies were picked out for DNA sequencing.

The positive clones with correct sequences were inoculated in 2×YT liquid medium containing the corresponding antibiotics and cultured at 37° C. with shaking for more than 12 h. The bacterial cells were collected for plasmid extraction to obtain the expression plasmids for the light chain and the heavy chain of humanized antibodies. The concentration and purity of the plasmids were detected by a nucleic acid quantitative analyzer.

The plasmids were transfected into HEK293E cells, and a large number of antibodies were expressed and purified. The purity, activity and affinity were tested and analyzed.

The humanized antibodies with good purity, activity and affinity were selected, and named as SHS006-T-Hu17-31, and SHS006-T-Hu23-53. The sequences are shown in Table 10.

TABLE 10

| Sequences of humanized anti-TIGIT antibodies | | | | |
|---|---|---|---|---|
| Humanized Antibody | Amino acid sequence of heavy chain variable region | Amino acid sequence of light chain variable region | H1CDR1, H1CDR2, H1CDR3 | L1CDR1, L1CDR2, L1CDR3 |
| HS006-T-Hu17-31 | SEQ ID NO: 98 | SEQ ID NO: 100 | SEQ ID NOs: 25, 26, 27 | SEQ ID NO: 31, 32, 33 |
| SHS006-T-Hu23-53 | SEQ ID NO: 99 | SEQ ID NO: 101 | SEQ ID NO: 28, 29, 30 | SEQ ID NO: 34, 35, 36 |

Example 7 Determination of Cell Function of Anti-TIGIT Antibody

The cell function of the anti-TIGIT antibody of the present disclosure was determined by a luciferase reporter gene system (purchased from BPS Bioscience, USA), with antibody 22G2 as a control.

The experimental steps are as follows:

(1) Preparation of target cells: CD155/TCR Activator-CHO cells were plated in a cell culture plate at a density of $2.5\times10^4$ cells/mL (detection well and NTC) and 100 μL/well, and the cell culture plate was placed in a 37° C., 5% $CO_2$ incubator for culture overnight;

(2) Preparation of effector cells: TIGIT/NFAT-reporter-Jurkat cells were washed with assay medium, and adjusted to a density of $4\times10^5$ cells/mL;

(3) Incubation of antibody with effector cells: The gradiently diluted anti-TIGIT antibody of the present disclosure and the effector cells (V:V=1:1, 60 μL each) were incubated at 37° C. for 30 min;

(4) Incubation with target cells: The medium in the target cell culture plate was discarded. A complex of TIGIT/NFAT-reporter-Jurkat cells and the antibody was added at 100 L/well, and 100 μL of assay medium was added to BG well. The cell culture plate was placed into the incubator for 5-6 h of incubation;

(5) Detection: Reagent A and reagent B were melted in a water bath. Reagent B was diluted with reagent A at a volume ratio of 1:100 and mixed well in the dark. 100 μL of the one-step luciferase reagent was added to each well. The cell culture plate was shaken slightly at room temperature for 15-30 min and then detected by a luminometer.

The relationship between the absorbance of each sample and the concentration of the antibody was plotted to show the folds of the expression of luciferase induced by the antibody at different concentrations comparing to the blank control group. The Top value and $EC_{50}$ value were calculated according to the data and are shown in Table 11.

TABLE 11

| Luciferase expression induced by anti-TIGIT antibody | | |
|---|---|---|
| | Antibody name | |
| Parameter | 22G2 | SHS006-23 |
| Top (fold) | 1.589 | 1.621 |
| $EC_{50}$ (nM) | 0.104 | 0.019 |

The experimental results show that the $EC_{50}$ value of the luciferase expression induced by the anti-TIGIT antibody of the present disclosure was significantly lower than that of the control antibody 22G2, indicating that the anti-TIGIT antibody of the present disclosure can more effectively activate T cells by blocking the binding of TIGIT-CD155, and has a significantly better effect than 22G2 in terms of activating T cells and killing tumors.

Example 8 Binding Activity Assay of Anti-TIGIT Antibodies to Human TIGIT (by ELISA)

The binding activity of antibodies was analyzed by ELISA. Human TIGIT-His protein (1 μg/well, Sino Biological, 10917-H08H) was coated on 96-well ELISA plates for 2 h of incubation at 37° C. The plates were washed with 1×PBST 3 times, blocked with 5% skimmed milk at 4° C. overnight and then washed 3 times with 1×PBST. The anti-TIGIT antibodies of the present disclosure were used as the primary antibody and added to the ELISA plates in 5-fold gradient dilution with a total of 8 concentrations: 2000 ng/mL, 400 ng/mL, 80 ng/mL, 16 ng/mL, 3.2 ng/mL, 0.64 ng/mL, 0.128 ng/mL, and 0 ng/mL respectively. The plates were incubated at 37° C. for 1.5 h and washed with 1×PBST 5 times. Anti-Human IgG HRP (Jackson, 109-035-003, 1:10000) was used as the secondary antibody. The plates were incubated at 37° C. for 40 min. After the plates were washed with 1×PBST 5 times, the color developing solution TMB was added to the plates, and microplate reader (Thermo, Multiskan FC) was used to read OD450 value after termination of the reaction. $EC_{50}$ was generated by GraphPad. The results are shown in Table 12.

TABLE 12

| Binding activity of anti-TIGIT antibody to human TIGIT | | | | |
|---|---|---|---|---|
| | Antibody name | | | |
| Parameter | SHS006-23CHI | SHS006-HuT23-53 | SHS006-17CHI | SHS006-T-Hu17-31 |
| $EC_{50}$ (nM) | 1.686 | 2.428 | 1.578 | 1.589 |

The experimental results show that the anti-TIGIT antibodies SHS006-17CHI, SHS006-T-Hul7-31, SHS006-23CHI, and SHS006-T-Hu23-53 of the present disclosure all have good binding ability to human TIGIT.

Example 9 Binding Activity Assay of Anti-TIGIT Antibodies to TIGIT on Cell Surface (by FACS)

The binding activity of antibodies was analyzed by FACS. hTIGIT-CHO-K1 cells were plated at $1\times10^5$ cells per well, and cultured overnight at 37° C. and 5% $CO_2$. On the second day, the cells were washed twice with cell staninning buffer. The anti-TIGIT antibodies provided by the present disclosure were used as the primary antibody and added to the cell plates in gradient dilution with a total of 8 concentrations: 2000 ng/mL, 400 ng/mL, 80 ng/mL, 40 ng/mL, 20 ng/mL, 4 ng/mL, 0.8 ng/mL, and 0.16 ng/mL respectively. 22G2 was used as the positive control antibody. The cell plates were incubated at 37° C. for 1 h. After the cell plates were washed with cell staninning buffer twice, PE anti-human IgG Fc (Biolegend, 409304, 1.2 μL/well) was added as the secondary antibody. The cell plates were incubated at 4° C. in the dark for 30 min. After the plates were washed with cell staninning buffer twice, the mean value at the wavelength of 585 nm was measured by a flow cytometry (ACEABIO, Novocyte). $EC_{50}$ was generated by GraphPad.

The results are shown in Table 13.

TABLE 13

Binding activity of anti-TIGIT antibodies to TIGIT on cell surface

| | Antibody name | | | | |
|---|---|---|---|---|---|
| Parameter | 22G2 | SHS006-23CHI | SHS006-T-Hu23-53 | SHS006-17CHI | SHS006-T-Hu17-31 |
| $EC_{50}$ (nM) | 0.4114 | 0.2349 | 0.1989 | 0.4076 | 0.3033 |

The experimental results show that the humanized anti-TIGIT antibodies SHS006-T-Hu23-53 and SHS006-T-Hul7-31 of the present disclosure can bind to TIGIT on the cell surface, and have a better binding ability than antibody 22G2.

Example 10 Affinity Assay of Anti-TIGIT Antibodies to Human TIGIT Protein

The affinity of the humanized anti-TIGIT antibodies prepared in Examples 1 and 2 to the antigen TIGIT-his was determined by Fortebio Octet. The humanized anti-TIGIT antibodies were diluted with SD buffer (PBST+0.02% Tween™20+0.1% BSA) to a concentration of 5 μg/mL, and the antigen TIGIT-His was diluted with SD buffer in 4-fold gradient dilution to make the concentrations to be 1 μg/mL, 0.25 μg/mL, 0.0625 μg/mL and 0 μg/mL. SA sensor was used to solidify the antigen, and affinity assay was performed according to the manual of Fortebio Octet RED96. The specific parameters and experimental results are shown in Table 14.

TABLE 14

Affinity assay of antibodies to human TIGIT protein

| Antibody | KD (M) | kon (1/Ms) | kdis (1/s) |
|---|---|---|---|
| SHS006-T-Hu17-31 | 3.27E−10 | 7.31E+05 | 2.39E−04 |
| SHS006-T-Hu23-53 | 1.14E−09 | 1.33E+06 | 1.51E−03 |

The experimental results show that the humanized anti-TIGIT antibodies SHS006-T-Hul7-31 and SHS006-T-Hu23-53 of the present disclosure have high affinity with human TIGIT protein.

Example 11 Blocking Activity Assay on Binding of TIGIT and CD155 by ELISA

The blocking activity of the antibodies was analyzed by ELISA. Human CD155-hFc protein (1 μg/well) was coated onto 96-well ELISA plates for 2 h of incubation at 37° C. The plates were washed with 1×PBST 3 times, blocked with 5% skimmed milk at 4° C. overnight, and then washed with 1×PBST 3 times. The anti-TIGIT antibodies provided by the present disclosure were mixed with TIGIT-mFc and served as the primary antibody, where the anti-TIGIT antibody was added to the ELISA plates in gradient dilution with a total of 8 concentrations: 5000 ng/mL, 1667 ng/mL, 556 ng/mL, 278 ng/mL, 139 ng/mL, 46 ng/mL, 15 ng/mL, and 0 ng/mL, respectively. 22G2 was used as the positive control antibody, and TIGIT-mFc had a constant concentration of 1 μg/mL. The plates were incubated at 37° C. for 2 h and washed with 1×PBST 5 times. Goat anti mouse IgG-HRP antibody (abeam, Ab6789, 1:10000) was used as the secondary antibody. The plates were incubated at 37° C. for 40 min. After the plates were washed with 1×PBST 5 times, the color developing solution TMB was added to the plates, and microplate reader (Thermo, Multiskan FC) was used to read OD450 value after termination of the reaction. $IC_{50}$ was generated by GraphPad. The results are shown in Table 15.

TABLE 15

Blocking activity of anti-TIGIT antibodies on binding of TIGIT and CD155

| | Antibody name | | | | |
|---|---|---|---|---|---|
| Parameter | 22G2 | SHS006-23CHI | SHS006-T-Hu23-53 | SHS006-17CHI | SHS006-T-Hu17-31 |
| $IC_{50}$ (nM) | 1.336 | 1.042 | 1.015 | 1.031 | 0.9537 |

The experimental results show that the humanized anti-TIGIT antibodies SHS006-T-Hu23-53 and SHS006-T-Hul7-31 of the present disclosure have the ability to block the binding between human TIGIT and CD155, and have a better blocking ability than antibody 22G2.

Example 12 Blocking Activity Assay on Binding of TIGIT and CD155 by FACS

The ability of the anti-TIGIT antibody provided by the present disclosure to block TIGIT from binding to CD155 on cell surface was detected by FACS. hCD155-CHO-K1 cells positive for CD155 were used as a CD155 provider. In the presence of a serially diluted anti-TIGIT antibody, the binding of TIGIT-mFc to CD155-CHO-K1 was monitored. PE Goat anti mouse IgG (Biolegend, 405307, 1.2 L/well) was used as the secondary antibody to monitor the changes of TIGIT-mFc. 22G2 was used as the positive control for blocking TIGIT from binding to CD155 on cell surface. Flow cytometer (ACEABIO, Novocyte) was used to read the mean value at a wavelength of 585 nm, and $IC_{50}$ was generated by GraphPad. The results are shown in Table 16.

TABLE 16

| Blocking activity of anti-TIGIT antibodies on binding of TIGIT and CD155 | | | | | |
|---|---|---|---|---|---|
| | Antibody name | | | | |
| Parameter | 22G2 | SHS006-23CHI | SHS006-T-Hu23-53 | SHS006-17CHI | SHS006-T-Hu17-31 |
| $IC_{50}$ | 1.667 | 1.493 | 1.396 | 1.041 | 0.9820 |

The experimental results show that the humanized anti-TIGIT antibodies SHS006-T-Hul7-31 and SHS006-T-Hu23-53 of the present disclosure have the ability to block the binding between human TIGIT and CD155, and have a better blocking ability than antibody 22G2.

Example 13 Construction, Expression and Purification of Anti-TIGIT/Anti-PD-L1 Bispecific Antibodies 1. Construction of Expression Vector for Bispecific Anti-TIGIT/Anti-PD-L1 Antibodies The anti-PD-L1 antibodies used in the present disclosure were mouse monoclonal antibodies obtained by screening after immunizing mice with human PD-L1-his protein, including PL-7 (heavy chain variable region set forth in SEQ ID NO: 37 and light chain variable region set forth in SEQ ID NO: 41) and PL-16 (heavy chain variable region set forth in SEQ ID NO: 39 and light chain variable region set forth in SEQ ID NO: 43), which were then humanized and screened to obtain humanized monoclonal antibodies HuPL7-21 (heavy chain variable region set forth in SEQ ID NO: 50 and light chain variable region set forth in SEQ ID NO: 54), HuPL7-43 (heavy chain variable region set forth in SEQ ID NO: 52 and light chain variable region set forth in SEQ ID NO: 56), and HuPL16-42 (heavy chain variable region set forth in SEQ ID NO: 61, and light chain variable region set forth in SEQ ID NO: 64).

The anti-TIGIT antibody used in the present disclosure is mouse monoclonal antibody T-23 (heavy chain variable region set forth in SEQ ID NO: 76, and light chain variable region set forth in SEQ ID NO: 78) obtained by screening after immunizing mice with human TIGIT-his protein, which was then humanized and screened to obtain humanized monoclonal antibody HuT23-53 (heavy chain variable region set forth in SEQ ID NO: 99 and light chain variable region set forth in SEQ ID NO: 101).

Figure 2:
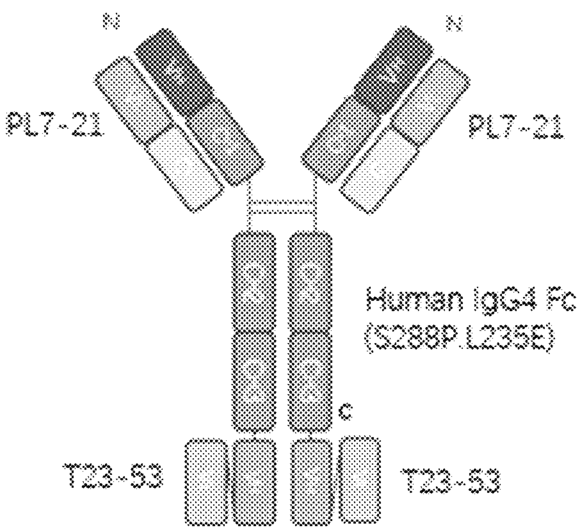
FIG. 2 shows a schematic diagram of the structure of the bispecific anti-TIGIT/anti-PD-L1 antibody with a ScFv structure.

An anti-TIGIT/anti-PD-L1 bispecific antibody involving two structures was constructed using the variable region sequences of the above humanized anti-PD-L1 and anti-TIGIT antibodies in the present disclosure. These two structures were respectively an asymmetric structure constituted with ScFab components (such as the bispecific antibody HuPL721-T2353-ScFab in this example) and a symmetrical structure constituted with ScFv components (such as the bispecific antibody HuPL721-T2353-ScFv in this example). Among them, the bispecific antibody with ScFab structure is shown in FIG. 1. Specifically, the bispecific antibody was formed by heterodimerization of two single chains from anti-PD-L1 antibody and anti-TIGIT antibody respectively. Unlike the natural IgG antibody, the light chains of both anti-PD-L1 and anti-TIGIT antibodies in the bispecific antibody were linked to the N-terminal of the heavy chain by an additional flexible peptide linker, which contained glycine (G) and serine (S) residues, including GGGGS (SEQ ID NO: 112) repeats, preferably 8 GGGGS (SEQ ID NO: 112) repeats. In addition, in order to promote the formation of heterodimers, the S354C/T366W mutation was further added to the CH3 domain of the anti-TIGIT antibody single chain, and the Y349C/T366S/L368A/Y407V mutation was further added to the CH3 domain of the anti-PD-L1 antibody single chain on the basis of the above S228P or S228P/L235E mutation. The bispecific antibody with ScFv structure is shown in FIG. 2. Specifically, the ScFv heavy chain of the TIGIT antibody was linked to the C-terminal of the complete heavy chain of the anti-PD-L1 antibody by a flexible peptide linker, which contained glycine (G) and serine (S) residues, including GGGGS (SEQ ID NO: 112) repeats, preferably 8 GGGGS (SEQ ID NO: 112) repeats. In addition, in the above two bispecific antibodies, a cysteine mutation can be introduced both at the VH44 position of the heavy chain variable region and the VL100 position of the light chain variable region, to form a VH44-VL100 disulfide bond, thereby increasing the stability of the antibody structure.

Figure 5A:
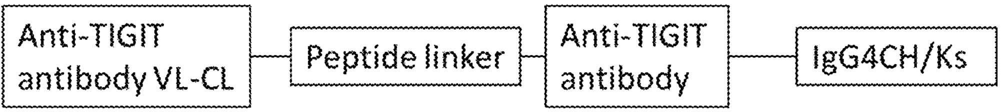
FIG. 5A shows a schematic diagram of the structure of Peptide 1 and FIG. 5B shows the structure of Peptide 2 of the bispecific antibody with asymmetric structure.
Figure 5B:
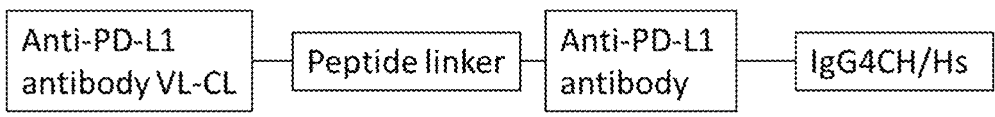

Schematic diagrams of the sequences of the bispecific antibody with asymmetric structure of the present disclosure are as follows:

Structure of peptide 1 is shown in FIG. 5A, and structure of peptide 2 is shown in FIG. 5B.

Schematic diagrams of the sequences of the bispecific antibody with symmetrical structure of the present disclosure are as follows:

structure of Peptide 1 is shown in FIG. 4A; and structure of Peptide 2 is shown in FIG. 4B;

wherein, IgG4CH/Ks represents the IgG4 constant region with mutations S228P, Y349C, T366S, L368A, and Y407V, IgG4CH/Hs represents the IgG4 constant region with mutations S228P, S354C, and T366W, and IgG4CH/PE represents the IgG4 constant region with mutations S228P and L235E.

According to the asymmetric structure above, the variable region sequences of the anti-PD-L1 antibody HuPL7-21 and the anti-TIGIT antibody HuT23-53 were used to construct the expression vectors ScFab-T2353-Knob-PHR (the sequence set forth in SEQ ID NO: 102) and HuPL721-scfab-hole-PHR (the sequence set forth in SEQ ID NO: 103) of the bispecific antibody HuPL721-T2353-ScFab.

According to the above symmetrical structure, the variable region sequences of the anti-PD-L1 antibody HuPL7-21 and the anti-TIGIT antibody HuT23-53 were used to construct the expression vectors PL721-T2353-scFv-HC-PHR (the sequence set forth in SEQ ID NO: 104) and HuPL721-VL1-PHR (the sequence set forth in SEQ ID NO: 105) of the bispecific antibody HuPL721-T2353-ScFv.

According to the above asymmetric structure, the variable region sequences of the anti-PD-L1 antibody HuPL7-43 and the anti-TIGIT antibody HuT23-53 were used to construct the expression vectors ScFab-T2353-Knob-PHR (the sequence set forth in SEQ ID NO: 102) and HuPL743-scfab-hole-PHR (the sequence set forth in SEQ ID NO: 106) of the bispecific antibody HuPL743-T2353-ScFab.

According to the above symmetrical structure, the variable region sequences of the anti-PD-L1 antibody HuPL7-43 and the anti-TIGIT antibody HuT23-53 were used to construct the expression vectors PL743-T2353-scFv-HC-PHR (the sequence set forth in SEQ ID NO: 107) and HuPL743-VL3-PHR (the sequence set forth in SEQ ID NO: 108) of the bispecific antibody HuPL743-T2353-ScFv.

According to the above asymmetric structure, the variable region sequences of the anti-PD-L1 antibody HuPL16-42 and the anti-TIGIT antibody HuT23-53 were used to construct the expression vectors ScFab-T2353-Knob-PHR (the sequence set forth in SEQ ID NO: 102) and HuPL1642-scfab-hole-PHR (the sequence set forth in SEQ ID NO: 109) of the bispecific antibody HuPL1642-T2353-ScFab.

According to the above symmetrical structure, the variable region sequences of the anti-PD-L1 antibody HuPL16-42 and the anti-TIGIT antibody HuT23-53 were used to construct the expression vectors PL1642-T2353-scFv-HC-PHR (the sequence set forth in SEQ ID NO: 110) and HuPL1642-VL2-PHR (the sequence set forth in SEQ ID NO: 111) of the bispecific antibody HuPL1642-T2353-ScFv;

2. Expression and Purification of Anti-TIGIT/Anti-PD-L1 Bispecific Antibodies

1) Expression of Anti-TIGIT/Anti-PD-L1 Bispecific Antibodies

HEK293E cells were inoculated in a 1 L cell culture flask at a density of $1.0\times10^6$ cells/mL, added with fresh pre-warmed FreeStyle 293 expression medium to make the total volume after inoculation reach 250 mL, and cultured overnight at 37° C. and 8% $CO_2$ in a humidified $CO_2$ incubator. 8 mL of FreeStyle 293 expression medium was added with 500 μL of 1 mg/mL PEI solution and mixed well. 250 μg of the expression vector to be transfected was added to 8.0 mL of FreeStyle 293 expression medium and mixed well, where the bispecific antibodies were co-transfected according to the ratio of the two vectors at 1:1. The mixed solution of PEI and FreeStyle 293 expression medium was added to the plasmid and mixed well. Then the resulting mixture was added to the cell culture for culture at 37° C. and 8% $CO_2$ in a humidified $CO_2$ incubator. The cells were fed on the 1st and 3rd day after cell transfection with 2.5 mL of glutamine (the stock solution had a concentration of 200 mM) to each bottle and 12.5 mL of OPM-CHO PFF05 and 5 mL of glucose (the stock solution had a concentration of 180 g/L) per 250 mL. When the cell viability dropped to 65%-75%, the cell supernatant was collected. The cell culture was centrifuged at 1500 rpm for 5 min to collect the supernatant, and then centrifuged at 8000 rpm for 20 min to collect the supernatant.

2) Affinity Chromatography Purification

Different affinity chromatography columns were used to perform purification by using AKTA (GE, AKTA pure-150) according to the properties of the proteins (see Table 17 for affinity chromatography columns suitable for the anti-TIGIT/anti-PD-L1 bispecific antibodies). The specific purification steps are as follows.

TABLE 17

Affinity chromatography columns suitable for anti-TIGIT/anti-PD-L1 bispecific antibodies

| Protein | Column | Brand | Model |
|---|---|---|---|
| Anti-TIGIT/anti-PD-L1 bispecific antibody | Protein A pre-packed column | GE | Hi Trap, Mabselect SuRe 5 ml |

Cleaning: The equipment and pipelines were cleaned with ultrapure water for 2 min with a flow rate of 10 mL/min, and then the chromatography system was cleaned with 0.1 M NaOH;

Column connection: The chromatography column was connected to the chromatography equipment, rinsed with ultrapure water for 5 min, and then rinsed with 0.1 M NaOH for 30 min with a retention time of 5 min;

Equilibration: Five CVs (column volume) of 20 mM PB+0.15 M NaCl (pH 7.2) was used to equilibrate the column;

Sample loading: The supernatant from cell culture was loaded to the column with a retention time of 5 min;

Post-equilibration: Five CVs of 20 mM PB+0.15 M NaCl (pH 7.2) was used to equilibrate the column;

Elution: Elution was performed with 50 mM acetic acid (pH=3.4), for a retention time of 5 min. Collection was started when UV280 reached about 50 mAu, and stopped when UV280 dropped to about 50 mAu. The sample was adjusted to the pH of 7.0 with 1 M Tris-HCl (pH 9.0);

Re-equilibration: Three CVs of 20 mM PB+0.15 M NaCl (pH 7.2) was used for equilibration with a retention time of 5 min;

On-column cleaning: Cleaning was performed with 0.1 M NaOH for 30 min with a retention time of 5 min;

Cleaning and preservation: Cleaning was performed with purified water for 10 min, and then 2 CVs of 20% ethanol.

The purity of the purified antibodies HuPL721-T2353-ScFab/ScFv, HuPL743-T2353-ScFab/ScFv, and HuPL1642-T2353-ScFab/ScFv was identified by SDS-PAGE and SEC-HPLC. If the purity was lower than 95%, the antibody was further purified to obtain a bispecific antibody molecule with SEC purity>95% for subsequent experiments.

Example 14 Binding Activity Assay of Anti-TIGIT/Anti-PD-L1 Bispecific Antibodies to Human PD-L1

The binding activity of antibodies was analyzed by FACS. hPD-L1-CHO-K1 cells were plated in cell plates at $1.5\times10^5$ cells per well. The anti-TIGIT/anti-PD-L1 bispecific antibodies provided by the present disclosure were used as the primary antibody, and added to the plates in gradient dilution with a total of 8 concentrations: 10000 ng/mL, 2000 ng/mL, 400 ng/mL, 80 ng/mL, 16 ng/mL, 3.2 ng/mL, 0.64 ng/mL and 0.128 ng/mL, respectively. The plates were incubated at 4° C. for 1.5 h, and washed with diluent (PBS+2% FBS) twice. PE anti-human IgG Fc (Abcam, ab98596, 0.8 μL/well) was used as the secondary antibody. The plates were incubated at 4° C. in the dark for 60 min. After the plates were washed with the diluent twice, the mean value at the wavelength of 585 nm was measured by a flow cytometry (ACEABIO, Novocyte). After converting the mass concentration to molar concentration, $EC_{50}$ was generated by GraphPad. The results are shown in Table 18.

TABLE 18

Binding activity of anti-TIGIT/anti-PD-L1 bispecific antibodies to human PD-L1

| Parameter | Antibody name | | | |
|---|---|---|---|---|
| | HuPL1642-T2353-ScFv | HuPL721-T2353-ScFv | HuPL743-T2353-ScFv | HuPL721-T2353-ScFab |
| $EC_{50}$ (nM) | 0.9553 | 0.7147 | 0.8204 | 1.766 |

The experimental results show that the anti-TIGIT/anti-PD-L1 bispecific antibodies HuPL721-T2353-ScFab, HuPL1642-T2353-ScFv, HuPL721-T2353-ScFv and HuPL743-T2353-ScFv provided by the present disclosure all have good binding ability to PD-L1.

Example 15 Binding Activity Assay of Anti-TIGIT/Anti-PD-L1 Bispecific Antibodies to Human TIGIT The binding activity of antibodies was analyzed by FACS. hTIGIT-CHO-K1 cells were plated in cell plates at $1.5\times10^5$ cells per well. The anti-TIGIT/anti-PD-L1 bispecific antibodies provided by the present disclosure were used as the primary antibody, and added to the plates in gradient dilution with a total of 8 concentrations: 2000 ng/mL, 400 ng/mL, 80 ng/mL, 40 ng/mL, 20 ng/mL, 4 ng/mL, 0.8 ng/mL, and 0.16 ng/mL, respectively. The plates were incubated at 4° C. for 1.5 h, and washed with diluent (PBS+2% FBS) twice. PE anti-human IgG Fc (Abeam, ab98596, 0.8 μL/well) was used as the secondary antibody. The plates were incubated at 4° C. in the dark for 60 min. After the plates were washed with the diluent twice, the mean value at the wavelength of 585 nm was measured by a flow cytometry (ACEABIO, Novocyte). After converting the mass concentration to molar concentration, $EC_{50}$ was generated by GraphPad. The results are shown in Table 19.

TABLE 19

Binding activity of anti-TIGIT/anti-PD-L1 bispecific antibodies to human TIGIT

| Parameter | Antibody name | |
|---|---|---|
| | HuPL721-T2353-ScFab | HuPL721-T2353-ScFv |
| $EC_{50}$ (nM) | 1.303 | 0.6118 |

The experimental results show that the anti-TIGIT/anti-PD-L1 bispecific antibodies HuPL721-T2353-ScFab and HuPL721-T2353-ScFv of the present disclosure have good binding ability to PD-L1.

Example 16 Blocking Activity Assay of Anti-TIGIT/Anti-PD-L1 Bispecific Antibodies on Binding of PD-L1 and PD-1

The binding activity of antibodies was analyzed by FACS. hPD-L1-CHO-K1 cells were plated in cell plates at $2.5\times10^5$ cells per well. The anti-TIGIT/anti-PD-L1 bispecific antibodies provided by the present disclosure were serially diluted, mixed with PD-1-mFc with a final concentration of 2 μg/mL, and then served as the primary antibody, which was then added to the plates in 3-fold gradient dilution with a total of 8 concentrations: 20000 ng/mL, 6666.66 ng/mL, 2222.22 ng/mL, 740.74 ng/mL, 246.9 ng/mL, 82.3 ng/mL, 27.4 ng/mL and 9.14 ng/mL, respectively. The plates were incubated at 4° C. for 1.5 h, and washed with diluent (PBS+2% FBS) twice. PE anti-Mouse IgG Fc (Biolegend, 405307, 0.8 μL/well) was used as the secondary antibody. The plates were incubated at 4° C. in the dark for 60 min. After the plates were washed with the diluent twice, the mean value at the wavelength of 585 nm was measured by a flow cytometry (ACEABIO, Novocyte). After converting the mass concentration to molar concentration, $IC_{50}$ was generated by GraphPad. The results are shown in Table 20.

TABLE 20

Blocking activity of anti-TIGIT/anti-PD-L1 bispecific antibodies on binding of PD-L1 and PD-1

| Parameter | Antibody name | |
|---|---|---|
| | HuPL721-T2353-ScFab | HuPL721-T2353-ScFv |
| $IC_{50}$ (nM) | 3.191 | 3.338 |

The experimental results show that the anti-TIGIT/anti-PD-L1 bispecific antibodies HuPL721-T2353-ScFab and HuPL721-T2353-ScFv of the present disclosure have the ability to block the binding of PD-L1 and PD-1.

Example 17 Blocking Activity Assay of Anti-TIGIT/Anti-PD-L1 Bispecific Antibodies on Binding of TIGIT and CD155

The blocking activity of antibodies was analyzed by FACS. hTIGIT-CHO-K1 cells were plated in cell plates at $2.5\times10^5$ cells per well. The anti-TIGIT/anti-PD-L1 bispecific antibodies provided by the present disclosure were serially diluted, mixed with TIGIT-mFc with a final concentration of 0.4 μg/mL, and served as the primary antibody, which was then added to the cell plates in gradient dilution with a total of 8 concentrations: 20000 ng/mL, 4000 ng/mL, 800 ng/mL, 400 ng/mL, 200 ng/mL, 100 ng/mL, 33.33 ng/mL, and 11.11 ng/mL, respectively. The plates were incubated at 4° C. for 1.5 h, and washed with diluent (PBS+2% FBS) twice. PE anti-Mouse IgG Fc (Biolegend, 405307, 0.8 μL/well) was used as the secondary antibody. The plates were incubated at 4° C. in the dark for 60 min. After the plates were washed with the diluent twice, the mean value at the wavelength of 585 nm was measured by a flow cytometry (ACEABIO, Novocyte). After converting the mass concentration to molar concentration, $IC_{50}$ was generated by GraphPad. The results are shown in Table 21.

TABLE 21

Blocking activity of anti-TIGIT/anti-PD-L1 bispecific antibodies on binding of TIGIT and CD155

| Parameter | Antibody name | | | |
|---|---|---|---|---|
| | HuPL1642-T2353-ScFab | HuPL1642-T2353-ScFv | HuPL721-T2353-ScFv | HuPL721-T2353-ScFab |
| $IC_{50}$ (nM) | 1.506 | 1.678 | 2.134 | 4.082 |

The experimental results show that the anti-TIGIT/anti-PD-L1 bispecific antibodies HuPL721-T2353-ScFab, HuPL721-T2353-ScFv, HuPL1642-T2353-ScFab and HuPL1642-T2353-ScFv of the present disclosure have a good ability to block the binding of TIGTI and CD155.

Example 18 Affinity Assay of Anti-TIGIT/Anti-PD-L1 Bispecific Antibodies

The affinity of the humanized anti-TIGIT/anti-PD-L1 antibodies prepared in Example 15 to the antigens PD-L1-his and TIGIT-his was determined by Fortebio Octet. Firstly, the antibodies HuPL721-T2353-ScFab/ScFv, HuPL743-T2353-ScFab/ScFv, and HuPL1642-T2353-ScFab/ScFv were diluted to 67 nM. AHC sensor was used to solidify the above antibodies. PD-L1-his was gradiently diluted with SD buffer (0.02% Tween™20+0.1% BSA solution) to 2 μg/mL, 0.4 μg/mL, and 0.08 μg/mL. TIGIT-his was gradiently diluted with SD buffer to 0.5 μg/mL, 0.1 μg/mL, and 0.02 μg/mL. Affinity assay was performed according to the manual of Fortebio Octet RED96. The specific parameters and experimental results are shown in Table 22 and Table 23.

TABLE 22

Affinity assay of anti-TIGIT/anti-PD-L1 bispecific antibodies to human PD-L1 protein

| Antibody | KD (M) | kon (1/Ms) | kdis (1/s) |
|---|---|---|---|
| HuPL7-21 | 1.49E−09 | 1.85E+05 | 2.76E−04 |
| HuPL16-42 | 1.90E−09 | 1.19E+05 | 2.25E−04 |

TABLE 22-continued

Affinity assay of anti-TIGIT/anti-PD-L1 bispecific antibodies to human PD-L1 protein

| Antibody | KD (M) | kon (1/Ms) | kdis (1/s) |
|---|---|---|---|
| HuPL1642-T2353-ScFab | 1.15E−09 | 1.84E+05 | 2.12E−04 |
| HuPL1642-T2353-ScFv | 2.08E−09 | 1.57E+05 | 3.26E−04 |
| HuPL721-T2353-ScFab | 1.32E−09 | 2.07E+05 | 2.73E−04 |
| HuPL721-T2353-ScFv | 2.67E−09 | 1.77E+05 | 4.72E−04 |

TABLE 23

Affinity assay of anti-TIGIT/anti-PD-L1 bispecific antibodies to human TIGIT protein

| Antibody | KD (M) | kon (1/Ms) | kdis (1/s) |
|---|---|---|---|
| T-Hu23-53 | 2.43E−09 | 7.92E+05 | 1.92E−03 |
| HuPL1642-T2353-ScFab | 1.39E−08 | 3.50E+05 | 4.87E−03 |
| HuPL1642-T2353-ScFv | 2.74E−09 | 8.72E+05 | 2.39E−03 |
| HuPL721-T2353-ScFab | 3.06E−09 | 1.09E+06 | 3.33E−03 |
| HuPL721-T2353-ScFv | 2.49E−09 | 9.96E+05 | 2.48E−03 |

The experimental results show that the anti-TIGIT/anti-PD-L1 bispecific antibodies HuPL1642-T2353-ScFab, HuPL1642-T2353-ScFv, HuPL721-T2353-ScFab and HuPL721-T2353-ScFv of the present disclosure have good affinity to human PD-L1 protein and to human TIGIT protein.

Example 19 In Vitro Efficacy Assay of Anti-TIGIT/Anti-PD-L1 Bispecific Antibodies The in vitro efficacy of the bispecific antibodies of the present disclosure was determined by using SEB (*Staphylococcus aureus* enterotoxin B) to stimulate PBMCs (peripheral blood mononuclear cells) twice.

PBMCs were thawed according to the required cell volume, added to 8-9 mL of IMDM complete medium, and centrifuged at 1200 rpm for 10 min. The supernatant was discarded, and the residue was resuspended with an appropriate amount of medium. The cells were counted with a hemocytometer, added to a 6-well plate, and added with SEB solution with a final concentration of 100 ng/mL for 48 h of incubation. After 48 h, the cell culture was centrifuged at 1200 rpm for 10 min, and the supernatant was discarded. The cells were washed with IMDM complete medium 1-2 times, resuspended with an appropriate amount of medium, counted with a hemocytometer, and resuspended to 1 M/mL. The cell suspension was added into a 96-well plate at 100 μL/well. Control IgG4 (Isotype) was prepared with IMDM complete medium to 4-fold concentration (80 μg/mL), added at 50 μL/well, marked well, and mixed by vortex. The antibody solutions were added to the corresponding wells, and medium was added to the control group at 50 L/well. The 96-well plate was placed in a 37° C. incubator for 1 h of incubation of cells with antibodies. After 1 h, SEB solution was prepared with IMDM complete medium to 4-fold concentration (400 ng/mL), and added to the corresponding wells at 50 μL/well. The 96-well plate was placed in a 5% $CO_2$ incubator at 37° C. for 48 h of incubation, and centrifuged to remove the supernatant to collect 150 μL of cell-free supernatant, which was then diluted according to a certain ratio, and detected for the concentration of IFN-γ in the supernatant according to the instructions of hIFN-γ (R&D system Cat: DY285B) ELISA detection kit. The results are shown in Table 24.

TABLE 24

Effect of antibodies of the present disclosure on the release of IFN-γ

| Group | IFN-γ (pg/mL) |
|---|---|
| Without SEB | 211.09 |
| SEB (100 ng/mL) | 526.09 |
| IgG4 (Isotype) (20 μg/mL) | 644.73 |
| HuPL16-42 (20 μg/mL) | 1662.55 |
| HuPL7-21 (20 μg/mL) | 999.00 |
| HuT23-53 (20 μg/mL) | 742.09 |
| HuPL16-42 (20 μg/mL) + HuT23-53 (20 μg/mL) | 1992.27 |
| HuPL7-21 (20 μg/mL) + HuT23-53 (20 μg/mL) | 1264.91 |
| HuPL1642-T2353-scFab (20 μg/mL) | 1765.64 |
| HuPL721-T2353-scFab (20 μg/mL) | 2146.91 |
| HuPL721-T2353-scFab (40 μg/mL) | 2862.82 |
| HuPL721-T2353-scFv (13.4 μg/mL) | 1542.27 |
| HuPL721-T2353-scFv (26.8 μg/mL) | 2842.36 |

The experimental results show that the antibodies of the present disclosure have good ability to promote IFN-γ release. The combination of antibodies HuPL16-42 and HuPL7-21 with antibody HuT23-53 has a better effect than that of an antibody alone. The bispecific antibody HuPL721-2353 promoted the release of IFN-γ in a dose-dependent manner. HuPL721-T2353-ScFv at half the molar number was still superior to the combination group [20 μg/mL+20 μg/mL for the monoclonal antibody combination group, 40 μg/mL for the scFab bispecific antibody group and 26.8 μg/mL for the scFv bispecific antibody group. These three groups of concentrations were equal based on the numbers of the two antigen-binding arms of TIGIT and PD-L1 (called "equal arm" concentration). Compared with 20 μg/mL+20 μg/mL of the monoclonal antibody combination group, the concentrations of 20 μg/mL of the scFab bispecific antibody group and 13.4 μg/mL of the scFv bispecific antibody group were equivalent to the concentration of half of the number of binding arms. From the perspective of molar number, the total molar number of the two molecules with concentrations of 20 μg/mL+20 μg/mL in the monoclonal antibody combination group was equal to the molar number of the scFab bispecific antibody group with a concentration of 40 μg/mL, and the molar number of the scFv bispecific antibody group with a concentration of 26.8 μl/mL was only half of that of the combination group with a concentration of 20 μg/mL+20 μg/mL and scFab bispecific antibody group with a concentration of 40 μg/mL].

Example 20 Detection of Inhibition of Transplanted Tumor Growth in Mice (Raji-PBMC-NSG Model) by Anti-PD-L1/Anti-TIGIT Bispecific Antibodies In the present disclosure, NSG mice (purchased from Beijing Biocytogen Pharmaceuticals Co., Ltd., China) and Raji-PD-L1 tumor cells (purchased from Immune Onco Biopharmaceuticals Co., Ltd., China) were used to establish a tumor xenograft model-Raji-PBMC-NSG model, to study the anti-tumor effect of the antibodies of the present disclosure in the subcutaneous transplant model of Raji-hPD-L1 lymphoma. Atezolizumab (Sino Biological, Cat: 68049-H001) was used as the anti-PD-L1 positive control antibody. Table 25 shows the experimental design for testing the antitumor effect of the drugs in Raji-PBMC-NSG tumor model.

TABLE 25

| Experimental design for testing drugs in Raji-PBMC-NSG model | | | | | | |
|---|---|---|---|---|---|---|
| Group | N* | Antibody | Mouse strain | Dosage (mg/kg) | Administration route | Administration frequency |
| 1 | 6 | PBS | NSG + PBMC | / | i.p. | BIW × 3 |
| 2 | 6 | Atezolizumab | NSG + PBMC | 10 | i.p. | BIW × 3 |
| 3 | 6 | HuPL7-21 | NSG + PBMC | 10 | i.p. | BIW × 3 |
| 4 | 6 | HuPL721-T2353-ScFab | NSG + PBMC | 20 | i.p. | BIW × 3 |
| 5 | 6 | HuPL721-T2353-ScFab | NSG + PBMC | 40 | i.p. | BIW × 3 |

*N refers to the number of mice per group;
i.p.: intraperitoneal injection;
BIW refers to administration twice a week.

The tumor growth inhibition rate ($TGI_{TV}$)% of each group is shown in Table 26.

TABLE 26

| Effect of each antibody on tumor volume of Raji-PBMC-NSG model mice | | |
|---|---|---|
| Group | Dosage (mg/kg) | $TGI_{TV}$ (%) |
| PBS | — | 0.00 |
| Atezolizumab | 10 | 37.40 |
| HuPL7-21 | 10 | 48.75 |
| HuPL721-T2353-ScFab | 20 | 53.83 |
| HuPL721-T2353-ScFab | 40 | 57.14 |

The antibodies HuPL7-21 and HuPL721-T2353-ScFab of the present disclosure have significantly better anti-tumor effect than that of Atezolizumab in vivo.

Example 21 Detection of Inhibition of Transplanted Tumor Growth in Mice (MC38-hPD-L1 Colon Cancer Model) by Anti-PD-L1/Anti-TIGIT Bispecific Antibodies Humanized bispecific B-hPD-L1/hTIGIT mice (purchased from Beijing Biocytogen Pharmaceuticals Co., Ltd., China) and MC38-hPD-L1 colon cancer cells (purchased from Shunran Biology (Shanghai) Co., Ltd., China) were used to establish an animal model for drug efficacy experiments. MC38-hPD-L1 colon cancer cells resuspended in PBS were inoculated subcutaneously on the right side of humanized B-hPD-L1/hTIGIT mice at a concentration of $5\times10^5$ cells/0.1 mL and a volume of 0.1 mL per mouse. When the average tumor volume reached 98 $mm^3$, appropriate mice were selected according to the tumor volume and body weight of the mice, and were evenly allocated to 6 experimental groups, with 8 mice in each group. The administration was started on the day of grouping. The specific administration protocol is shown in Table 27.

TABLE 27

| Administration protocol for humanized bispecific B-hPD-L1/hTIGIT mouse MC38-hPD-L1 colon cancer animal model experiment | | | | | |
|---|---|---|---|---|---|
| Group | Test substance | Dosage (mg/kg)[a] | Administration route | Administration frequency[b] | Administration number |
| G1 | PBS | — | i.p. | BIW | 6 |
| G2 | Atezolizumab | 3 | i.p. | BIW | 6 |
| G3 | HuPL721-T2353-ScFab | 3.14 | i.p. | BIW | 6 |

TABLE 27-continued

| Administration protocol for humanized bispecific B-hPD-L1/hTIGIT mouse MC38-hPD-L1 colon cancer animal model experiment | | | | | |
|---|---|---|---|---|---|
| Group | Test substance | Dosage (mg/kg)[a] | Administration route | Administration frequency[b] | Administration number |
| G4 | HuPL721-T2353-ScFab | 6.27 | i.p. | BIW | 6 |

Note:
PBS: normal saline control group;
athe administration volume was calculated according to the body weight of the experimental animal at 10 μL/g;
[b]BIW refers to administration twice a week.

The results were recorded, and the tumor growth inhibition rate ($TGI_{TV}$) was calculated.

At the end of the experiment (i.e., the 24th day of administration after grouping), Atezolizumab at a dose of 3 mg/kg had a tumor inhibition rate of 35.3%. HuPL721-T2353-ScFab at a dose of 3.14 mg/kg and 6.27 mg/kg had a tumor inhibition rate of 30.6% and 50.7%, respectively. The experimental results show that the bispecific anti-TIGIT/anti-PD-L1 antibody HuPL721-T2353-ScFab had a significant inhibitory effect on the growth of MC38-hPD-L1 subcutaneous xenograft tumor in a dose-dependent manner.

The above examples demonstrate that the anti-TIGIT antibodies, anti-PD-L1 antibodies, and anti-TIGIT/anti-PD-L1 bispecific antibodies provided by the present disclosure can significantly inhibit tumor growth and have significant anti-tumor effects, suggesting that these antibodies can be used in the manufacture of anti-tumor medicaments with a good market prospect.

Although the present disclosure has been described above in detail, those skilled in the art should understand that various modifications and changes can be made to the present disclosure without departing from the spirit and scope of the present disclosure. The scope of the present disclosure should not be limited to the detailed description above, but should be attributed to the claims.

The invention claimed is:

1. An anti-TIGIT antibody or antigen-binding fragment thereof, comprising a heavy chain variable region and a light chain variable region, wherein:
(1) the heavy chain variable region comprises H1CDR1, H1CDR2 and H1CDR3 set forth in SEQ ID NOs: 28, 29 and 30, respectively; and
(2) the light chain variable region comprises L1CDR1, L1CDR2 and L1CDR3 set forth in SEQ ID NOs: 34, 35 and 36, respectively.

2. The anti-TIGIT antibody or antigen-binding fragment thereof according to claim 1, wherein:
(1) the heavy chain variable region has an amino acid sequence selected from the group consisting of:
(b1) an amino acid sequence set forth in SEQ ID NO: 99;
(b2) amino acid sequences derived from the amino acid sequence set forth in (b1) by substitution, deletion or addition of one or more amino acids and functionally identical or similar to the amino acid sequence set forth in (b1); and
(b3) amino acid sequences having at least 80% sequence identity to the amino acid sequence set forth in (b1); and
(2) the light chain variable region has an amino acid sequence selected from the group consisting of:
(b4) an amino acid sequence set forth in SEQ ID NO: 101;
(b5) amino acid sequences derived from the amino acid sequence set forth in (b4) by substitution, deletion or addition of one or more amino acids and functionally identical or similar to the amino acid sequence set forth in (b4); and
(b6) amino acid sequences having at least 80% sequence identity to the amino acid sequence set forth in (b4).

3. An anti-TIGIT/anti-PD-L1 antibody comprising the anti-TIGIT antibody or antigen-binding fragment thereof according to claim 1 and an anti-PD-L1 antibody or antigen-binding fragment thereof, wherein:
the anti-TIGIT antibody or antigen-binding fragment thereof comprises a first heavy chain variable region and a first light chain variable region, wherein:
(1) the first heavy chain variable region comprises H1CDR1, H1CDR2 and H1CDR3 set forth in SEQ ID NOs: 28, 29 and 30, respectively; and
(2) the first light chain variable region comprises L1CDR1, L1CDR2 and L1CDR3 set forth in SEQ ID NOs: 34, 35 and 36, respectively; and
the anti-PD-L1 antibody or antigen-binding fragment thereof comprises a second heavy chain variable region and a second light chain variable region, wherein:
(1) the second heavy chain variable region comprises H2CDR1, H2CDR2 and H2CDR3 set forth in SEQ ID NOs: 1, 2 and 3, respectively; and
(2) the second light chain variable region comprises L2CDR1, L2CDR2 and L2CDR3 set forth in SEQ ID NOs: 13, 14 and 15, respectively.

4. The anti-TIGIT/anti-PD-L1 antibody according to claim 3, wherein:
the anti-TIGIT antibody or antigen-binding fragment thereof comprises a first heavy chain variable region and a first light chain variable region, wherein:
(1) the first heavy chain variable region has an amino acid sequence selected from the group consisting of:
(b1) an amino acid sequence set forth in SEQ ID NO: 99;
(b2) amino acid sequences derived from the amino acid sequence set forth in (b1) by substitution, deletion or addition of one or more amino acids and functionally identical or similar to the amino acid sequence set forth in (b1); and
(b3) amino acid sequences having at least 80% sequence identity to the amino acid sequence set forth in (b1); and
(2) the first light chain variable region has an amino acid sequence selected from the group consisting of:
(b4) an amino acid sequence set forth in SEQ ID NO: 101;
(b5) amino acid sequences derived from the amino acid sequence set forth in (b4) by substitution, deletion or addition of one or more amino acids and functionally identical or similar to the amino acid sequence set forth in (b4); and
(b6) amino acid sequences having at least 80% sequence identity to the amino acid sequence set forth in (b4); and
the anti-PD-L1 antibody or antigen-binding fragment thereof comprises a second heavy chain variable region and a second light chain variable region, wherein:
(1) the second heavy chain variable region has an amino acid sequence selected from the group consisting of:
(B1) an amino acid sequence set forth in SEQ ID NO: 50;
(B2) amino acid sequences derived from the amino acid sequence set forth in (B1) by substitution, deletion or addition of one or more amino acids and functionally identical or similar to the amino acid sequence set forth in (B1); and
(B3) amino acid sequences having at least 80% sequence identity to the amino acid sequence set forth in (B1); and
(2) the second light chain variable region has an amino acid sequence selected from the group consisting of:
(B4) an amino acid sequence set forth in SEQ ID NO: 54;
(B5) amino acid sequences derived from the amino acid sequence set forth in (B4) by substitution, deletion or addition of one or more amino acids and functionally identical or similar to the amino acid sequence set forth in (B4); and (B6) amino acid sequences having at least 80% sequence identity to the amino acid sequence set forth in (B4).

5. The anti-TIGIT/anti-PD-L1 antibody according to claim 3, wherein the antibody is a bispecific antibody.

6. The anti-TIGIT/anti-PD-L1 antibody according to claim 3, wherein the antibody is a humanized antibody.

7. An isolated nucleic acid encoding the anti-TIGIT/anti-PD-L1 antibody according to claim 3.

8. An expression vector comprising the nucleic acid according to claim 7.

9. A host cell transformed with the expression vector according to claim 8, wherein the host cell is selected from the group consisting of prokaryotic cells and eukaryotic cells.

10. A method for producing the anti-TIGIT/anti-PD-L1 antibody according to claim 3, comprising expressing the antibody in a host cell transformed with an expression vector comprising an isolated nucleic acid encoding the anti-TIGIT/anti-PD-L1 antibody, and isolating the antibody from the host cell.

11. A pharmaceutical composition comprising the anti-TIGIT/anti-PD-L1 antibody according to claim 3 and a pharmaceutically acceptable carrier.

12. A method for treating a tumor, comprising administering to a subject in need thereof the anti-TIGIT/anti-PD-L1 antibody according to claim 3.

13. The host cell according to claim 9, wherein the cell is a mammalian cell.

14. A pharmaceutical composition comprising the anti-TIGIT antibody according to claim 1 and a pharmaceutically acceptable carrier.

15. A method for treating a tumor, comprising administering to a subject in need thereof the anti-TIGIT antibody according to claim 1.

16. The anti-TIGIT/anti-PD-L1 antibody according to claim 3, wherein the anti-TIGIT antibody or antigen-binding fragment thereof has a structure of (VL-CL)-peptide linker-(VH)-IgG4CH, and the anti-PD-L1 antibody or antigen-binding fragment thereof has a structure of (VL-CL)-peptide linker-(VH)-IgG4CH; or the anti-TIGIT antibody or antigen-binding fragment thereof has a structure of (VL-VH)-peptide linker-IgG4FC, and the anti-PD-L1 antibody or antigen-binding fragment thereof has a structure of (VL-CL)-peptide linker-(VH)-IgG4CH;

wherein the peptide linker is in the form of (GGGGS; SEQ ID NO: 112)n, wherein n is 1-12.

17. The anti-TIGIT/anti-PD-L1 antibody according to claim 3, wherein the antibody consists of two peptide chains, wherein one peptide chain has an amino acid sequence set forth in SEQ ID NO: 102, and the other peptide chain has an amino acid sequence set forth in SEQ ID NO: 103, or one peptide chain has an amino acid sequence set forth in SEQ ID NO: 104, and the other peptide chain has an amino acid sequence set forth in SEQ ID NO: 105.

* * * * *

SEQUENCE LISTING

<160> NUMBER OF SEQ ID NOS: 112

<210> SEQ ID NO 1
<211> LENGTH: 10
<212> TYPE: PRT
<213> ORGANISM: Mus musculus
<220> FEATURE:
<223> OTHER INFORMATION: HCDR1

<400> SEQUENCE: 1

```
Gly Asp Ser Ile Thr Ser Gly Tyr Trp Asn
1               5                   10
```

<210> SEQ ID NO 2
<211> LENGTH: 16
<212> TYPE: PRT
<213> ORGANISM: Mus musculus
<220> FEATURE:
<223> OTHER INFORMATION: HCDR2

<400> SEQUENCE: 2

```
Tyr Ile Ser Tyr Thr Gly Ser Thr Tyr Tyr Asn Leu Ser Leu Lys Ser
1               5                   10                  15
```

<210> SEQ ID NO 3
<211> LENGTH: 10
<212> TYPE: PRT
<213> ORGANISM: Mus musculus
<220> FEATURE:
<223> OTHER INFORMATION: HCDR3

<400> SEQUENCE: 3

```
Tyr Ile Leu Trp Leu Arg His Phe Asp Tyr
1               5                   10
```

<210> SEQ ID NO 4
<211> LENGTH: 10
<212> TYPE: PRT
<213> ORGANISM: Mus musculus
<220> FEATURE:
<223> OTHER INFORMATION: HCDR1

<400> SEQUENCE: 4

```
Gly Tyr Ser Ile Thr Ser Asp Tyr Trp Asn
1               5                   10
```

<210> SEQ ID NO 5
<211> LENGTH: 16
<212> TYPE: PRT
<213> ORGANISM: Mus musculus
<220> FEATURE:
<223> OTHER INFORMATION: HCDR2

<400> SEQUENCE: 5

```
Tyr Ile Ser Tyr Thr Gly Ser Thr Tyr Tyr Asn Pro Ser Leu Lys Arg
1               5                   10                  15
```

<210> SEQ ID NO 6
<211> LENGTH: 10
<212> TYPE: PRT
<213> ORGANISM: Mus musculus
<220> FEATURE:
<223> OTHER INFORMATION: HCDR3

<400> SEQUENCE: 6

```
Tyr Arg Asp Trp Pro Gly Tyr Phe Asp Val
1               5                   10
```

<210> SEQ ID NO 7
<211> LENGTH: 10
<212> TYPE: PRT
<213> ORGANISM: Mus musculus
<220> FEATURE:
<223> OTHER INFORMATION: HCDR1

<400> SEQUENCE: 7

Gly Tyr Thr Phe Thr Arg Asn Thr Met His
1               5                   10

<210> SEQ ID NO 8
<211> LENGTH: 17
<212> TYPE: PRT
<213> ORGANISM: Mus musculus
<220> FEATURE:
<223> OTHER INFORMATION: HCDR2

<400> SEQUENCE: 8

Phe Ile Asp Pro His Asn Thr Tyr Thr Arg Tyr Asn Gln Lys Phe Lys
1               5                   10                  15

Asp

<210> SEQ ID NO 9
<211> LENGTH: 5
<212> TYPE: PRT
<213> ORGANISM: Mus musculus
<220> FEATURE:
<223> OTHER INFORMATION: HCDR3

<400> SEQUENCE: 9

Trp Pro Met Asp Tyr
1               5

<210> SEQ ID NO 10
<211> LENGTH: 10
<212> TYPE: PRT
<213> ORGANISM: Mus musculus
<220> FEATURE:
<223> OTHER INFORMATION: HCDR1

<400> SEQUENCE: 10

Gly Tyr Ser Phe Thr Ser Asn Trp Met Asn
1               5                   10

<210> SEQ ID NO 11
<211> LENGTH: 17
<212> TYPE: PRT
<213> ORGANISM: Mus musculus
<220> FEATURE:
<223> OTHER INFORMATION: HCDR2

<400> SEQUENCE: 11

Met Ile His Leu Tyr Asp Ser Glu Thr Lys Leu Asn Pro Asn Phe Gln
1               5                   10                  15

Asp

<210> SEQ ID NO 12
<211> LENGTH: 9
<212> TYPE: PRT
<213> ORGANISM: Mus musculus
<220> FEATURE:
<223> OTHER INFORMATION: HCDR3

<400> SEQUENCE: 12

Ser Ala Gly Asn Tyr Arg Phe Ala Tyr
1 5

<210> SEQ ID NO 13
<211> LENGTH: 17
<212> TYPE: PRT
<213> ORGANISM: Mus musculus
<220> FEATURE:
<223> OTHER INFORMATION: LCDR1

<400> SEQUENCE: 13

Lys Ser Ser Gln Ser Leu Leu Tyr Ser Ser Asn Gln Lys Asn Ser Leu
1 5 10 15

Ala

<210> SEQ ID NO 14
<211> LENGTH: 7
<212> TYPE: PRT
<213> ORGANISM: Mus musculus
<220> FEATURE:
<223> OTHER INFORMATION: LCDR2

<400> SEQUENCE: 14

Trp Ala Ser Thr Arg Glu Ser
1 5

<210> SEQ ID NO 15
<211> LENGTH: 9
<212> TYPE: PRT
<213> ORGANISM: Mus musculus
<220> FEATURE:
<223> OTHER INFORMATION: LCDR3

<400> SEQUENCE: 15

Gln Gln Tyr Tyr Gly Tyr Pro Leu Thr
1 5

<210> SEQ ID NO 16
<211> LENGTH: 11
<212> TYPE: PRT
<213> ORGANISM: Mus musculus
<220> FEATURE:
<223> OTHER INFORMATION: LCDR1

<400> SEQUENCE: 16

Arg Ala Ser Lys Ser Ile Arg Lys Phe Leu Ala
1 5 10

<210> SEQ ID NO 17
<211> LENGTH: 7
<212> TYPE: PRT
<213> ORGANISM: Mus musculus
<220> FEATURE:
<223> OTHER INFORMATION: LCDR2

<400> SEQUENCE: 17

Ser Gly Ser Thr Leu Gln Ser
1 5

<210> SEQ ID NO 18
<211> LENGTH: 9
<212> TYPE: PRT
<213> ORGANISM: Mus musculus
<220> FEATURE:
<223> OTHER INFORMATION: LCDR3

<400> SEQUENCE: 18

Gln His Tyr Asn Glu Tyr Pro Phe Thr
1 5

<210> SEQ ID NO 19
<211> LENGTH: 17
<212> TYPE: PRT
<213> ORGANISM: Mus musculus
<220> FEATURE:
<223> OTHER INFORMATION: LCDR1

<400> SEQUENCE: 19

Lys Ser Ser Gln Ser Leu Ser Trp Ser Glu Asn Gln Asn Asn Tyr Leu
1 5 10 15

Ser

<210> SEQ ID NO 20
<211> LENGTH: 7
<212> TYPE: PRT
<213> ORGANISM: Mus musculus
<220> FEATURE:
<223> OTHER INFORMATION: LCDR2

<400> SEQUENCE: 20

Gly Ala Ser Ile Arg Glu Ser
1 5

<210> SEQ ID NO 21
<211> LENGTH: 11
<212> TYPE: PRT
<213> ORGANISM: Mus musculus
<220> FEATURE:
<223> OTHER INFORMATION: LCDR3

<400> SEQUENCE: 21

Gln His Asn His Gly Ser Phe Leu Pro Tyr Thr
1 5 10

<210> SEQ ID NO 22
<211> LENGTH: 11
<212> TYPE: PRT
<213> ORGANISM: Mus musculus
<220> FEATURE:
<223> OTHER INFORMATION: LCDR1

<400> SEQUENCE: 22

Lys Ala Ser Gln Ser Val Ser Asn Glu Val Ala
1 5 10

<210> SEQ ID NO 23
<211> LENGTH: 7
<212> TYPE: PRT
<213> ORGANISM: Mus musculus
<220> FEATURE:
<223> OTHER INFORMATION: LCDR2

<400> SEQUENCE: 23

Ser Ala Ser Ser Arg Tyr Thr
1 5

<210> SEQ ID NO 24
<211> LENGTH: 9
<212> TYPE: PRT
<213> ORGANISM: Mus musculus
<220> FEATURE:
<223> OTHER INFORMATION: LCDR3

<400> SEQUENCE: 24

Gln Gln His Tyr Ser Ser Pro Leu Thr
1 5

<210> SEQ ID NO 25
<211> LENGTH: 7
<212> TYPE: PRT
<213> ORGANISM: Mus musculus
<220> FEATURE:
<223> OTHER INFORMATION: HCDR1

<400> SEQUENCE: 25

Thr Tyr Gly Leu Gly Val Gly
1 5

<210> SEQ ID NO 26
<211> LENGTH: 16
<212> TYPE: PRT
<213> ORGANISM: Mus musculus
<220> FEATURE:
<223> OTHER INFORMATION: HCDR2

<400> SEQUENCE: 26

Asn Ile Trp Trp Asp Asp Asp Glu Tyr Tyr Asn Pro Ser Leu Lys Asn
1 5 10 15

<210> SEQ ID NO 27
<211> LENGTH: 16
<212> TYPE: PRT
<213> ORGANISM: Mus musculus
<220> FEATURE:
<223> OTHER INFORMATION: HCDR3

<400> SEQUENCE: 27

Ile Ala Arg Pro His Tyr Tyr Trp Asp Gly Arg Tyr Ile Leu Asp Val
1 5 10 15

<210> SEQ ID NO 28
<211> LENGTH: 5
<212> TYPE: PRT
<213> ORGANISM: Mus musculus
<220> FEATURE:
<223> OTHER INFORMATION: HCDR1

<400> SEQUENCE: 28

Asp His Trp Met Ser
1 5

<210> SEQ ID NO 29
<211> LENGTH: 17
<212> TYPE: PRT
<213> ORGANISM: Mus musculus
<220> FEATURE:
<223> OTHER INFORMATION: HCDR2

<400> SEQUENCE: 29

Asn Ile Gln Tyr Asp Gly Ser Tyr Thr Asn Tyr Ala Pro Ser Leu Lys
1 5 10 15

Asn

<210> SEQ ID NO 30
<211> LENGTH: 17
<212> TYPE: PRT
<213> ORGANISM: Mus musculus
<220> FEATURE:

<223> OTHER INFORMATION: HCDR3

<400> SEQUENCE: 30

Gly His Phe Arg Ile Thr Met Ala Ser Met Gly Ala Ser Ala Ser Val
1 5 10 15

Tyr

<210> SEQ ID NO 31
<211> LENGTH: 16
<212> TYPE: PRT
<213> ORGANISM: Mus musculus
<220> FEATURE:
<223> OTHER INFORMATION: LCDR1

<400> SEQUENCE: 31

Arg Ser Ser Lys Ser Leu Leu His Ser Asn Gly Ile Thr Tyr Leu Ser
1 5 10 15

<210> SEQ ID NO 32
<211> LENGTH: 7
<212> TYPE: PRT
<213> ORGANISM: Mus musculus
<220> FEATURE:
<223> OTHER INFORMATION: LCDR2

<400> SEQUENCE: 32

Gln Ile Ser Asn Leu Ala Ser
1 5

<210> SEQ ID NO 33
<211> LENGTH: 9
<212> TYPE: PRT
<213> ORGANISM: Mus musculus
<220> FEATURE:
<223> OTHER INFORMATION: LCDR3

<400> SEQUENCE: 33

Met Gln Phe Leu Glu Val Pro Tyr Thr
1 5

<210> SEQ ID NO 34
<211> LENGTH: 11
<212> TYPE: PRT
<213> ORGANISM: Mus musculus
<220> FEATURE:
<223> OTHER INFORMATION: LCDR1

<400> SEQUENCE: 34

Arg Thr Ser Gln Asp Ile Gly Asn Ser Leu Arg
1 5 10

<210> SEQ ID NO 35
<211> LENGTH: 7
<212> TYPE: PRT
<213> ORGANISM: Mus musculus
<220> FEATURE:
<223> OTHER INFORMATION: LCDR2

<400> SEQUENCE: 35

Gly Ala Thr Asn Leu Ala Asn
1 5

<210> SEQ ID NO 36
<211> LENGTH: 9
<212> TYPE: PRT
<213> ORGANISM: Mus musculus

```
<220> FEATURE:
<223> OTHER INFORMATION: LCDR3

<400> SEQUENCE: 36

Leu Gln His Asn Glu Tyr Pro Leu Thr
1               5


<210> SEQ ID NO 37
<211> LENGTH: 118
<212> TYPE: PRT
<213> ORGANISM: Mus musculus
<220> FEATURE:
<223> OTHER INFORMATION: Heavy chain variable region

<400> SEQUENCE: 37

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
            20                  25                  30

Tyr Trp Asn Trp Ile Arg Lys Phe Pro Gly Asn Lys Leu Glu Tyr Met
        35                  40                  45

Gly Tyr Ile Ser Tyr Thr Gly Ser Thr Tyr Tyr Asn Leu Ser Leu Lys
    50                  55                  60

Ser Arg Ile Ser Ile Thr Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Arg Tyr Ile Leu Trp Leu Arg His Phe Asp Tyr Trp Gly Gln Gly Thr
            100                 105                 110

Thr Leu Thr Val Ser Ser
        115


<210> SEQ ID NO 38
<211> LENGTH: 118
<212> TYPE: PRT
<213> ORGANISM: Mus musculus
<220> FEATURE:
<223> OTHER INFORMATION: Heavy chain variable region

<400> SEQUENCE: 38

Glu Val Gln Leu Gln Glu Ser Gly Pro Gly Leu Ala Lys Pro Ser Gln
1               5                   10                  15

Thr Leu Ser Leu Thr Cys Ser Val Thr Gly Tyr Ser Ile Thr Ser Asp
            20                  25                  30

Tyr Trp Asn Trp Ile Arg Lys Phe Pro Gly Asn Lys Leu Glu Tyr Met
        35                  40                  45

Gly Tyr Ile Ser Tyr Thr Gly Ser Thr Tyr Tyr Asn Pro Ser Leu Lys
    50                  55                  60

Arg Arg Val Ser Ile Thr Arg Asp Thr Ser Lys Asn Asn Tyr Tyr Leu
65                  70                  75                  80

Gln Leu Asn Ser Val Thr Thr Glu Asp Thr Ala Thr Tyr Tyr Cys Ala
                85                  90                  95

Arg Tyr Arg Asp Trp Pro Gly Tyr Phe Asp Val Trp Gly Ala Gly Thr
            100                 105                 110

Thr Val Thr Val Ser Ser
        115


<210> SEQ ID NO 39
<211> LENGTH: 114
```

<212> TYPE: PRT
<213> ORGANISM: Mus musculus
<220> FEATURE:
<223> OTHER INFORMATION: Heavy chain variable region

<400> SEQUENCE: 39

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Asn
            20                  25                  30

Thr Met His Trp Ile Lys Gln Arg Pro Gly Gln Gly Leu Glu Trp Ile
        35                  40                  45

Gly Phe Ile Asp Pro His Asn Thr Tyr Thr Arg Tyr Asn Gln Lys Phe
    50                  55                  60

Lys Asp Arg Ala Thr Leu Thr Ala Asp Lys Ser Ser Ser Thr Ala Tyr
65                  70                  75                  80

Met Gln Leu Ser Ser Leu Ser Ser Glu Asp Ser Ala Val Tyr Tyr Cys
                85                  90                  95

Ala Arg Trp Pro Met Asp Tyr Trp Gly Gln Gly Thr Ser Val Thr Val
            100                 105                 110

Ser Ser
```

<210> SEQ ID NO 40
<211> LENGTH: 118
<212> TYPE: PRT
<213> ORGANISM: Mus musculus
<220> FEATURE:
<223> OTHER INFORMATION: Heavy chain variable region

<400> SEQUENCE: 40

```
Gln Val Gln Leu Gln Gln Pro Gly Ala Glu Leu Val Arg Pro Gly Thr
1               5                   10                  15

Ser Val Asn Leu Ser Cys Lys Ala Ser Gly Tyr Ser Phe Thr Ser Asn
            20                  25                  30

Trp Met Asn Trp Val Lys Gln Arg Pro Gly Gln Gly Leu Glu Trp Ile
        35                  40                  45

Gly Met Ile His Leu Tyr Asp Ser Glu Thr Lys Leu Asn Pro Asn Phe
    50                  55                  60

Gln Asp Lys Ala Thr Leu Thr Val Asp Lys Ser Ser Ser Ile Ala Tyr
65                  70                  75                  80

Met Gln Leu Ser Ser Pro Thr Ser Glu Asp Ser Ala Val Tyr Tyr Cys
                85                  90                  95

Ala Arg Ser Ala Gly Asn Tyr Arg Phe Ala Tyr Trp Gly Gln Gly Thr
            100                 105                 110

Leu Val Thr Val Ser Ala
        115
```

<210> SEQ ID NO 41
<211> LENGTH: 113
<212> TYPE: PRT
<213> ORGANISM: Mus musculus
<220> FEATURE:
<223> OTHER INFORMATION: Light chain variable region

<400> SEQUENCE: 41

```
Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30
```

```
Ser Asn Gln Lys Asn Ser Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Gly Tyr Pro Leu Thr Phe Gly Ala Gly Thr Lys Leu Glu Leu
            100                 105                 110

Lys


<210> SEQ ID NO 42
<211> LENGTH: 107
<212> TYPE: PRT
<213> ORGANISM: Mus musculus
<220> FEATURE:
<223> OTHER INFORMATION: Light chain variable region

<400> SEQUENCE: 42

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Arg Lys Phe
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Thr Leu Glu Pro
65                  70                  75                  80

Glu Asp Phe Ala Val Tyr Tyr Cys Gln His Tyr Asn Glu Tyr Pro Phe
                85                  90                  95

Thr Phe Gly Gly Gly Thr Lys Leu Glu Ile Lys
            100                 105


<210> SEQ ID NO 43
<211> LENGTH: 115
<212> TYPE: PRT
<213> ORGANISM: Mus musculus
<220> FEATURE:
<223> OTHER INFORMATION: Light chain variable region

<400> SEQUENCE: 43

Asp Ile Val Met Thr Gln Phe Pro Ser Ser Leu Ala Val Thr Ala Gly
1               5                   10                  15

Glu Lys Val Thr Met Arg Cys Lys Ser Ser Gln Ser Leu Ser Trp Ser
            20                  25                  30

Glu Asn Gln Asn Asn Tyr Leu Ser Trp Tyr Gln Gln Lys Gln Gly Gln
        35                  40                  45

Pro Pro Lys Leu Leu Ile Tyr Gly Ala Ser Ile Arg Glu Ser Trp Val
    50                  55                  60

Pro Asp Arg Phe Thr Gly Ser Gly Ser Gly Thr Asp Phe Thr Leu Thr
65                  70                  75                  80

Ile Ser Asn Val His Ala Glu Asp Leu Gly Val Tyr Phe Cys Gln His
                85                  90                  95

Asn His Gly Ser Phe Leu Pro Tyr Thr Phe Gly Gly Gly Thr Lys Leu
            100                 105                 110
```

```
Glu Ile Lys
        115


<210> SEQ ID NO 44
<211> LENGTH: 107
<212> TYPE: PRT
<213> ORGANISM: Mus musculus
<220> FEATURE:
<223> OTHER INFORMATION: Light chain variable region

<400> SEQUENCE: 44

Ser Ile Val Met Thr Gln Thr Pro Lys Phe Leu Pro Val Thr Ala Glu
1               5                   10                  15

Asp Arg Val Thr Ile Thr Cys Lys Ala Ser Gln Ser Val Ser Asn Glu
            20                  25                  30

Val Ala Trp Tyr Gln Gln Lys Pro Gly Gln Ser Pro Lys Leu Leu Ile
        35                  40                  45

Tyr Ser Ala Ser Ser Arg Tyr Thr Gly Val Pro Asp Arg Phe Ile Gly
    50                  55                  60

Gly Gly Ser Ala Thr Asp Phe Thr Phe Thr Ile Ser Ser Val Gln Val
65                  70                  75                  80

Glu Asp Leu Ala Val Tyr Phe Cys Gln Gln His Tyr Ser Ser Pro Leu
                85                  90                  95

Thr Phe Gly Ala Gly Thr Lys Leu Glu Leu Lys
            100                 105


<210> SEQ ID NO 45
<211> LENGTH: 99
<212> TYPE: PRT
<213> ORGANISM: Artificial Sequence
<220> FEATURE:
<223> OTHER INFORMATION: Heavy chain variable region

<400> SEQUENCE: 45

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg


<210> SEQ ID NO 46
<211> LENGTH: 98
<212> TYPE: PRT
<213> ORGANISM: Artificial Sequence
<220> FEATURE:
<223> OTHER INFORMATION: Heavy chain variable region

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
```

```
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg


<210> SEQ ID NO 47
<211> LENGTH: 101
<212> TYPE: PRT
<213> ORGANISM: Artificial Sequence
<220> FEATURE:
<223> OTHER INFORMATION: Light chain variable region

<400> SEQUENCE: 47

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro
            100


<210> SEQ ID NO 48
<211> LENGTH: 118
<212> TYPE: PRT
<213> ORGANISM: Artificial Sequence
<220> FEATURE:
<223> OTHER INFORMATION: Heavy chain variable region

<400> SEQUENCE: 48

Gln Val Gln Leu Gln Glu Ser Gly Pro Gly Leu Val Lys Pro Ser Gln
1               5                   10                  15

Thr Leu Ser Leu Thr Cys Thr Val Ser Gly Asp Ser Ile Thr Ser Gly
            20                  25                  30

Tyr Trp Asn Trp Ile Arg Gln His Pro Gly Lys Gly Leu Glu Trp Ile
        35                  40                  45

Gly Tyr Ile Ser Tyr Thr Gly Ser Thr Tyr Tyr Asn Leu Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Tyr Ile Leu Trp Leu Arg His Phe Asp Tyr Trp Gly Gln Gly Thr
            100                 105                 110

Leu Val Thr Val Ser Ser
```

115

<210> SEQ ID NO 49
<211> LENGTH: 118
<212> TYPE: PRT
<213> ORGANISM: Artificial Sequence
<220> FEATURE:
<223> OTHER INFORMATION: Heavy chain variable region

<400> SEQUENCE: 49

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Asp Ser Ile Thr Ser Gly
            20                  25                  30

Tyr Trp Asn Trp Ile Arg Gln His Pro Gly Lys Gly Leu Glu Tyr Ile
        35                  40                  45

Gly Tyr Ile Ser Tyr Thr Gly Ser Thr Tyr Tyr Asn Leu Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Tyr Ile Leu Trp Leu Arg His Phe Asp Tyr Trp Gly Gln Gly Thr
            100                 105                 110

Leu Val Thr Val Ser Ser
        115
```

<210> SEQ ID NO 50
<211> LENGTH: 118
<212> TYPE: PRT
<213> ORGANISM: Artificial Sequence
<220> FEATURE:
<223> OTHER INFORMATION: Heavy chain variable region

<400> SEQUENCE: 50

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Asp Ser Ile Thr Ser Gly
            20                  25                  30

Tyr Trp Asn Trp Ile Arg Gln His Pro Gly Lys Gly Leu Glu Tyr Ile
        35                  40                  45

Gly Tyr Ile Ser Tyr Thr Gly Ser Thr Tyr Tyr Asn Leu Ser Leu Lys
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Tyr Ile Leu Trp Leu Arg His Phe Asp Tyr Trp Gly Gln Gly Thr
            100                 105                 110

Leu Val Thr Val Ser Ser
        115
```

<210> SEQ ID NO 51
<211> LENGTH: 118
<212> TYPE: PRT
<213> ORGANISM: Artificial Sequence
<220> FEATURE:
<223> OTHER INFORMATION: Heavy chain variable region

<400> SEQUENCE: 51

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Asp Ser Ile Thr Ser Gly
            20                  25                  30

Tyr Trp Asn Trp Ile Arg Gln His Pro Gly Lys Gly Leu Glu Tyr Ile
        35                  40                  45

Gly Tyr Ile Ser Tyr Thr Gly Ser Thr Tyr Tyr Asn Leu Ser Leu Lys
    50                  55                  60

Ser Arg Ile Thr Ile Ser Arg Asp Thr Ser Lys Asn Gln Tyr Ser Leu
65                  70                  75                  80

Lys Leu Ser Ser Val Thr Ala Ala Asp Thr Ala Val Tyr Tyr Cys Ala
                85                  90                  95

Arg Tyr Ile Leu Trp Leu Arg His Phe Asp Tyr Trp Gly Gln Gly Thr
            100                 105                 110

Leu Val Thr Val Ser Ser
        115


<210> SEQ ID NO 52
<211> LENGTH: 118
<212> TYPE: PRT
<213> ORGANISM: Artificial Sequence
<220> FEATURE:
<223> OTHER INFORMATION: Heavy chain variable region

<400> SEQUENCE: 52

Gln Val Gln Leu Gln Glu Ser Gly Pro Gly Leu Val Lys Pro Ser Gln
1               5                   10                  15

Thr Leu Ser Leu Thr Cys Thr Val Ser Gly Asp Ser Ile Thr Ser Gly
            20                  25                  30

Tyr Trp Asn Trp Ile Arg Gln His Pro Gly Lys Gly Leu Glu Tyr Met
        35                  40                  45

Gly Tyr Ile Ser Tyr Thr Gly Ser Thr Tyr Tyr Asn Leu Ser Leu Lys
    50                  55                  60

Ser Arg Ile Thr Ile Ser Arg Asp Thr Ser Lys Asn Gln Tyr Ser Leu
65                  70                  75                  80

Lys Leu Ser Ser Val Thr Ala Ala Asp Thr Ala Val Tyr Tyr Cys Ala
                85                  90                  95

Arg Tyr Ile Leu Trp Leu Arg His Phe Asp Tyr Trp Gly Gln Gly Thr
            100                 105                 110

Leu Leu Thr Val Ser Ser
        115


<210> SEQ ID NO 53
<211> LENGTH: 113
<212> TYPE: PRT
<213> ORGANISM: Artificial Sequence
<220> FEATURE:
<223> OTHER INFORMATION: Light chain variable region

<400> SEQUENCE: 53

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Asn Gln Lys Asn Ser Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
```

```
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Gly Tyr Pro Leu Thr Phe Gly Gly Gly Thr Lys Leu Glu Ile
            100                 105                 110

Lys


<210> SEQ ID NO 54
<211> LENGTH: 113
<212> TYPE: PRT
<213> ORGANISM: Artificial Sequence
<220> FEATURE:
<223> OTHER INFORMATION: Light chain variable region

<400> SEQUENCE: 54

Asp Ile Val Met Thr Gln Ser Pro Asp Ser Leu Ala Val Ser Leu Gly
1               5                   10                  15

Glu Arg Ala Thr Ile Ser Cys Lys Ser Ser Gln Ser Leu Leu Tyr Ser
            20                  25                  30

Ser Asn Gln Lys Asn Ser Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Gly Tyr Pro Leu Thr Phe Gly Gly Gly Thr Lys Leu Glu Ile
            100                 105                 110

Lys


<210> SEQ ID NO 55
<211> LENGTH: 113
<212> TYPE: PRT
<213> ORGANISM: Artificial Sequence
<220> FEATURE:
<223> OTHER INFORMATION: Light chain variable region

<400> SEQUENCE: 55

Asp Ile Val Met Thr Gln Ser Pro Asp Ser Leu Ala Val Ser Leu Gly
1               5                   10                  15

Glu Arg Val Thr Ile Ser Cys Lys Ser Ser Gln Ser Leu Leu Tyr Ser
            20                  25                  30

Ser Asn Gln Lys Asn Ser Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Tyr Tyr Gly Tyr Pro Leu Thr Phe Gly Gly Gly Thr Lys Leu Glu Ile
            100                 105                 110

Lys
```

<210> SEQ ID NO 56
<211> LENGTH: 113
<212> TYPE: PRT
<213> ORGANISM: Artificial Sequence
<220> FEATURE:
<223> OTHER INFORMATION: Light chain variable region

<400> SEQUENCE: 56

```
Asp Ile Val Met Thr Gln Ser Pro Asp Ser Leu Ala Val Ser Leu Gly
1               5                   10                  15

Glu Arg Val Thr Met Ser Cys Lys Ser Ser Gln Ser Leu Leu Tyr Ser
            20                  25                  30

Ser Asn Gln Lys Asn Ser Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Tyr Tyr Gly Tyr Pro Leu Thr Phe Gly Gly Gly Thr Lys Leu Glu Ile
            100                 105                 110

Lys
```

<210> SEQ ID NO 57
<211> LENGTH: 114
<212> TYPE: PRT
<213> ORGANISM: Artificial Sequence
<220> FEATURE:
<223> OTHER INFORMATION: Heavy chain variable region

<400> SEQUENCE: 57

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Asn
            20                  25                  30

Thr Met His Trp Val Arg Gln Ala Pro Gly Gln Arg Leu Glu Trp Met
        35                  40                  45

Gly Phe Ile Asp Pro His Asn Thr Tyr Thr Arg Tyr Asn Gln Lys Phe
    50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Pro Met Asp Tyr Trp Gly Gln Gly Thr Leu Val Thr Val
            100                 105                 110

Ser Ser
```

<210> SEQ ID NO 58
<211> LENGTH: 114
<212> TYPE: PRT
<213> ORGANISM: Artificial Sequence
<220> FEATURE:
<223> OTHER INFORMATION: Heavy chain variable region

<400> SEQUENCE: 58

```
Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Arg Asn
            20                  25                  30

Thr Met His Trp Val Arg Gln Ala Pro Gly Gln Arg Leu Glu Trp Met
        35                  40                  45

Gly Phe Ile Asp Pro His Asn Thr Tyr Thr Arg Tyr Asn Gln Lys Phe
    50                  55                  60

Lys Asp Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Pro Met Asp Tyr Trp Gly Gln Gly Thr Leu Val Thr Val
            100                 105                 110

Ser Ser


<210> SEQ ID NO 59
<211> LENGTH: 114
<212> TYPE: PRT
<213> ORGANISM: Artificial Sequence
<220> FEATURE:
<223> OTHER INFORMATION: Heavy chain variable region

<400> SEQUENCE: 59

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Asn
            20                  25                  30

Thr Met His Trp Ile Arg Gln Ala Pro Gly Gln Arg Leu Glu Trp Met
        35                  40                  45

Gly Phe Ile Asp Pro His Asn Thr Tyr Thr Arg Tyr Asn Gln Lys Phe
    50                  55                  60

Lys Asp Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Pro Met Asp Tyr Trp Gly Gln Gly Thr Leu Val Thr Val
            100                 105                 110

Ser Ser


<210> SEQ ID NO 60
<211> LENGTH: 114
<212> TYPE: PRT
<213> ORGANISM: Artificial Sequence
<220> FEATURE:
<223> OTHER INFORMATION: Heavy chain variable region

<400> SEQUENCE: 60

Gln Val Gln Leu Val Gln Ser Gly Ala Glu Val Ala Lys Pro Gly Ala
1               5                   10                  15

Ser Val Lys Val Ser Cys Lys Ala Ser Gly Tyr Thr Phe Thr Arg Asn
            20                  25                  30

Thr Met His Trp Ile Arg Gln Ala Pro Gly Gln Arg Leu Glu Trp Ile
        35                  40                  45

Gly Phe Ile Asp Pro His Asn Thr Tyr Thr Arg Tyr Asn Gln Lys Phe
    50                  55                  60

Lys Asp Arg Ala Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
```

```
                85                  90                  95

Ala Arg Trp Pro Met Asp Tyr Trp Gly Gln Gly Thr Leu Val Thr Val
            100                 105                 110

Ser Ser


<210> SEQ ID NO 61
<211> LENGTH: 114
<212> TYPE: PRT
<213> ORGANISM: Artificial Sequence
<220> FEATURE:
<223> OTHER INFORMATION: Heavy chain variable region

<400> SEQUENCE: 61

Gln Val Gln Leu Val Gln Ser Gly Ala Glu Val Ala Lys Pro Gly Ala
1               5                   10                  15

Ser Val Lys Met Ser Cys Lys Ala Ser Gly Tyr Thr Phe Thr Arg Asn
            20                  25                  30

Thr Met His Trp Ile Lys Gln Ala Pro Gly Gln Arg Leu Glu Trp Ile
        35                  40                  45

Gly Phe Ile Asp Pro His Asn Thr Tyr Thr Arg Tyr Asn Gln Lys Phe
    50                  55                  60

Lys Asp Arg Ala Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Pro Met Asp Tyr Trp Gly Gln Gly Thr Leu Val Thr Val
            100                 105                 110

Ser Ser


<210> SEQ ID NO 62
<211> LENGTH: 115
<212> TYPE: PRT
<213> ORGANISM: Artificial Sequence
<220> FEATURE:
<223> OTHER INFORMATION: Light chain variable region

<400> SEQUENCE: 62

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Ser Trp Ser
            20                  25                  30

Glu Asn Gln Asn Asn Tyr Leu Ser Trp Tyr Gln Gln Lys Pro Gly Gln
        35                  40                  45

Pro Pro Lys Leu Leu Ile Tyr Gly Ala Ser Ile Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln His
                85                  90                  95

Asn His Gly Ser Phe Leu Pro Tyr Thr Phe Gly Gln Gly Thr Lys Leu
            100                 105                 110

Glu Ile Lys
        115


<210> SEQ ID NO 63
<211> LENGTH: 115
<212> TYPE: PRT
<213> ORGANISM: Artificial Sequence
```

<220> FEATURE:
<223> OTHER INFORMATION: Light chain variable region

<400> SEQUENCE: 63

```
Asp Ile Val Met Thr Gln Ser Pro Asp Ser Leu Ala Val Ser Leu Gly
1               5                   10                  15

Glu Arg Val Thr Ile Asn Cys Lys Ser Ser Gln Ser Leu Ser Trp Ser
            20                  25                  30

Glu Asn Gln Asn Asn Tyr Leu Ser Trp Tyr Gln Gln Lys Pro Gly Gln
        35                  40                  45

Pro Pro Lys Leu Leu Ile Tyr Gly Ala Ser Ile Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Gly Val Tyr Tyr Cys Gln His
                85                  90                  95

Asn His Gly Ser Phe Leu Pro Tyr Thr Phe Gly Gln Gly Thr Lys Leu
            100                 105                 110

Glu Ile Lys
        115
```

<210> SEQ ID NO 64
<211> LENGTH: 115
<212> TYPE: PRT
<213> ORGANISM: Artificial Sequence
<220> FEATURE:
<223> OTHER INFORMATION: Light chain variable region

<400> SEQUENCE: 64

```
Asp Ile Val Met Thr Gln Ser Pro Asp Ser Leu Ala Val Ser Leu Gly
1               5                   10                  15

Glu Arg Val Thr Met Arg Cys Lys Ser Ser Gln Ser Leu Ser Trp Ser
            20                  25                  30

Glu Asn Gln Asn Asn Tyr Leu Ser Trp Tyr Gln Gln Lys Pro Gly Gln
        35                  40                  45

Pro Pro Lys Leu Leu Ile Tyr Gly Ala Ser Ile Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Gly Val Tyr Tyr Cys Gln His
                85                  90                  95

Asn His Gly Ser Phe Leu Pro Tyr Thr Phe Gly Gln Gly Thr Lys Leu
            100                 105                 110

Glu Ile Lys
        115
```

<210> SEQ ID NO 65
<211> LENGTH: 378
<212> TYPE: PRT
<213> ORGANISM: Artificial Sequence
<220> FEATURE:
<223> OTHER INFORMATION: TIGIT-hIgG1-Fc fusion protein

<400> SEQUENCE: 65

```
Met Arg Trp Cys Leu Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30
```

```
Ile Ser Ala Glu Lys Gly Gly Ser Ile Ile Leu Gln Cys His Leu Ser
        35                  40                  45

Ser Thr Thr Ala Gln Val Thr Gln Val Asn Trp Glu Gln Gln Asp Gln
    50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95

Ser Leu Thr Val Asn Asp Thr Gly Glu Tyr Phe Cys Ile Tyr His Thr
            100                 105                 110

Tyr Pro Asp Gly Thr Tyr Thr Gly Arg Ile Phe Leu Glu Val Leu Glu
        115                 120                 125

Ser Ser Val Ala Glu His Gly Ala Arg Phe Gln Ile Pro Ile Glu Gly
    130                 135                 140

Arg Met Asp Pro Lys Ser Cys Asp Lys Thr His Thr Cys Pro Pro Cys
145                 150                 155                 160

Pro Ala Pro Glu Leu Leu Gly Gly Pro Ser Val Phe Leu Phe Pro Pro
                165                 170                 175

Lys Pro Lys Asp Thr Leu Met Ile Ser Arg Thr Pro Glu Val Thr Cys
            180                 185                 190

Val Val Val Asp Val Ser His Glu Asp Pro Glu Val Lys Phe Asn Trp
        195                 200                 205

Tyr Val Asp Gly Val Glu Val His Asn Ala Lys Thr Lys Pro Arg Glu
    210                 215                 220

Glu Gln Tyr Asn Ser Thr Tyr Arg Val Val Ser Val Leu Thr Val Leu
225                 230                 235                 240

His Gln Asp Trp Leu Asn Gly Lys Glu Tyr Lys Cys Lys Val Ser Asn
                245                 250                 255

Lys Ala Leu Pro Ala Pro Ile Glu Lys Thr Ile Ser Lys Ala Lys Gly
            260                 265                 270

Gln Pro Arg Glu Pro Gln Val Tyr Thr Leu Pro Pro Ser Arg Asp Glu
        275                 280                 285

Leu Thr Lys Asn Gln Val Ser Leu Thr Cys Leu Val Lys Gly Phe Tyr
    290                 295                 300

Pro Ser Asp Ile Ala Val Glu Trp Glu Ser Asn Gly Gln Pro Glu Asn
305                 310                 315                 320

Asn Tyr Lys Thr Thr Pro Pro Val Leu Asp Ser Asp Gly Ser Phe Phe
                325                 330                 335

Leu Tyr Ser Lys Leu Thr Val Asp Lys Ser Arg Trp Gln Gln Gly Asn
            340                 345                 350

Val Phe Ser Cys Ser Val Met His Glu Ala Leu His Asn His Tyr Thr
        355                 360                 365

Gln Lys Ser Leu Ser Leu Ser Pro Gly Lys
    370                 375


<210> SEQ ID NO 66
<211> LENGTH: 377
<212> TYPE: PRT
<213> ORGANISM: Artificial Sequence
<220> FEATURE:
<223> OTHER INFORMATION: TIGIT-mIgG1-Fc fusion protein

<400> SEQUENCE: 66

Met Arg Trp Cys Leu Leu Leu Ile Trp Ala Gln Gly Leu Arg Gln Ala
1               5                   10                  15
```

```
Pro Leu Ala Ser Gly Met Met Thr Gly Thr Ile Glu Thr Thr Gly Asn
            20                  25                  30

Ile Ser Ala Glu Lys Gly Gly Ser Ile Ile Leu Gln Cys His Leu Ser
        35                  40                  45

Ser Thr Thr Ala Gln Val Thr Gln Val Asn Trp Glu Gln Gln Asp Gln
    50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95

Ser Leu Thr Val Asn Asp Thr Gly Glu Tyr Phe Cys Ile Tyr His Thr
            100                 105                 110

Tyr Pro Asp Gly Thr Tyr Thr Gly Arg Ile Phe Leu Glu Val Leu Glu
        115                 120                 125

Ser Ser Val Ala Glu His Gly Ala Arg Phe Gln Ile Pro Phe Ser Pro
    130                 135                 140

Glu Pro Arg Gly Pro Thr Ile Lys Pro Cys Pro Pro Cys Lys Cys Pro
145                 150                 155                 160

Ala Pro Asn Leu Leu Gly Gly Pro Ser Val Phe Ile Phe Pro Pro Lys
                165                 170                 175

Ile Lys Asp Val Leu Met Ile Ser Leu Ser Pro Ile Val Thr Cys Val
            180                 185                 190

Val Val Asp Val Ser Glu Asp Asp Pro Asp Val Gln Ile Ser Trp Phe
        195                 200                 205

Val Asn Asn Val Glu Val His Thr Ala Gln Thr Gln Thr His Arg Glu
    210                 215                 220

Asp Tyr Asn Ser Thr Leu Arg Val Val Ser Ala Leu Pro Ile Gln His
225                 230                 235                 240

Gln Asp Trp Met Ser Gly Lys Glu Phe Lys Cys Lys Val Asn Asn Lys
                245                 250                 255

Asp Leu Pro Ala Pro Ile Glu Arg Thr Ile Ser Lys Pro Lys Gly Ser
            260                 265                 270

Val Arg Ala Pro Gln Val Tyr Val Leu Pro Pro Pro Glu Glu Glu Met
        275                 280                 285

Thr Lys Lys Gln Val Thr Leu Thr Cys Met Val Thr Asp Phe Met Pro
    290                 295                 300

Glu Asp Ile Tyr Val Glu Trp Thr Asn Asn Gly Lys Thr Glu Leu Asn
305                 310                 315                 320

Tyr Lys Asn Thr Glu Pro Val Leu Asp Ser Asp Gly Ser Tyr Phe Met
                325                 330                 335

Tyr Ser Lys Leu Arg Val Glu Lys Lys Asn Trp Val Glu Arg Asn Ser
            340                 345                 350

Tyr Ser Cys Ser Val Val His Glu Gly Leu His Asn His His Thr Thr
        355                 360                 365

Lys Ser Phe Ser Arg Thr Pro Gly Lys
    370                 375
```

<210> SEQ ID NO 67
<211> LENGTH: 150
<212> TYPE: PRT
<213> ORGANISM: Artificial Sequence
<220> FEATURE:
<223> OTHER INFORMATION: TIGIT-his fusion protein

<400> SEQUENCE: 67

```
Met Arg Trp Cys Leu Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Glu Lys Gly Gly Ser Ile Ile Leu Gln Cys His Leu Ser
        35                  40                  45

Ser Thr Thr Ala Gln Val Thr Gln Val Asn Trp Glu Gln Gln Asp Gln
    50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95

Ser Leu Thr Val Asn Asp Thr Gly Glu Tyr Phe Cys Ile Tyr His Thr
            100                 105                 110

Tyr Pro Asp Gly Thr Tyr Thr Gly Arg Ile Phe Leu Glu Val Leu Glu
        115                 120                 125

Ser Ser Val Ala Glu His Gly Ala Arg Phe Gln Ile Pro Ser Gly Ser
    130                 135                 140

His His His His His His
145                 150


<210> SEQ ID NO 68
<211> LENGTH: 580
<212> TYPE: PRT
<213> ORGANISM: Artificial Sequence
<220> FEATURE:
<223> OTHER INFORMATION: CD155-hIgG1-Fc fusion protein

<400> SEQUENCE: 68

Met Ala Arg Ala Met Ala Ala Ala Trp Pro Leu Leu Leu Val Ala Leu
1               5                   10                  15

Leu Val Leu Ser Trp Pro Pro Pro Gly Thr Gly Asp Val Val Val Gln
            20                  25                  30

Ala Pro Thr Gln Val Pro Gly Phe Leu Gly Asp Ser Val Thr Leu Pro
        35                  40                  45

Cys Tyr Leu Gln Val Pro Asn Met Glu Val Thr His Val Ser Gln Leu
    50                  55                  60

Thr Trp Ala Arg His Gly Glu Ser Gly Ser Met Ala Val Phe His Gln
65                  70                  75                  80

Thr Gln Gly Pro Ser Tyr Ser Glu Ser Lys Arg Leu Glu Phe Val Ala
                85                  90                  95

Ala Arg Leu Gly Ala Glu Leu Arg Asn Ala Ser Leu Arg Met Phe Gly
            100                 105                 110

Leu Arg Val Glu Asp Glu Gly Asn Tyr Thr Cys Leu Phe Val Thr Phe
        115                 120                 125

Pro Gln Gly Ser Arg Ser Val Asp Ile Trp Leu Arg Val Leu Ala Lys
    130                 135                 140

Pro Gln Asn Thr Ala Glu Val Gln Lys Val Gln Leu Thr Gly Glu Pro
145                 150                 155                 160

Val Pro Met Ala Arg Cys Val Ser Thr Gly Gly Arg Pro Pro Ala Gln
                165                 170                 175

Ile Thr Trp His Ser Asp Leu Gly Gly Met Pro Asn Thr Ser Gln Val
            180                 185                 190

Pro Gly Phe Leu Ser Gly Thr Val Thr Val Thr Ser Leu Trp Ile Leu
        195                 200                 205
```

```
Val Pro Ser Ser Gln Val Asp Gly Lys Asn Val Thr Cys Lys Val Glu
    210                 215                 220

His Glu Ser Phe Glu Lys Pro Gln Leu Leu Thr Val Asn Leu Thr Val
225                 230                 235                 240

Tyr Tyr Pro Pro Glu Val Ser Ile Ser Gly Tyr Asp Asn Asn Trp Tyr
                245                 250                 255

Leu Gly Gln Asn Glu Ala Thr Leu Thr Cys Asp Ala Arg Ser Asn Pro
            260                 265                 270

Glu Pro Thr Gly Tyr Asn Trp Ser Thr Thr Met Gly Pro Leu Pro Pro
        275                 280                 285

Phe Ala Val Ala Gln Gly Ala Gln Leu Leu Ile Arg Pro Val Asp Lys
    290                 295                 300

Pro Ile Asn Thr Thr Leu Ile Cys Asn Val Thr Asn Ala Leu Gly Ala
305                 310                 315                 320

Arg Gln Ala Glu Leu Thr Val Gln Val Lys Glu Gly Pro Pro Ser Glu
                325                 330                 335

His Ser Gly Met Ser Arg Asn Ile Glu Gly Arg Met Asp Pro Lys Ser
            340                 345                 350

Cys Asp Lys Thr His Thr Cys Pro Pro Cys Pro Ala Pro Glu Leu Leu
        355                 360                 365

Gly Gly Pro Ser Val Phe Leu Phe Pro Pro Lys Pro Lys Asp Thr Leu
    370                 375                 380

Met Ile Ser Arg Thr Pro Glu Val Thr Cys Val Val Val Asp Val Ser
385                 390                 395                 400

His Glu Asp Pro Glu Val Lys Phe Asn Trp Tyr Val Asp Gly Val Glu
                405                 410                 415

Val His Asn Ala Lys Thr Lys Pro Arg Glu Glu Gln Tyr Asn Ser Thr
            420                 425                 430

Tyr Arg Val Val Ser Val Leu Thr Val Leu His Gln Asp Trp Leu Asn
        435                 440                 445

Gly Lys Glu Tyr Lys Cys Lys Val Ser Asn Lys Ala Leu Pro Ala Pro
    450                 455                 460

Ile Glu Lys Thr Ile Ser Lys Ala Lys Gly Gln Pro Arg Glu Pro Gln
465                 470                 475                 480

Val Tyr Thr Leu Pro Pro Ser Arg Asp Glu Leu Thr Lys Asn Gln Val
                485                 490                 495

Ser Leu Thr Cys Leu Val Lys Gly Phe Tyr Pro Ser Asp Ile Ala Val
            500                 505                 510

Glu Trp Glu Ser Asn Gly Gln Pro Glu Asn Asn Tyr Lys Thr Thr Pro
        515                 520                 525

Pro Val Leu Asp Ser Asp Gly Ser Phe Phe Leu Tyr Ser Lys Leu Thr
    530                 535                 540

Val Asp Lys Ser Arg Trp Gln Gln Gly Asn Val Phe Ser Cys Ser Val
545                 550                 555                 560

Met His Glu Ala Leu His Asn His Tyr Thr Gln Lys Ser Leu Ser Leu
                565                 570                 575

Ser Pro Gly Lys
            580


<210> SEQ ID NO 69
<211> LENGTH: 579
<212> TYPE: PRT
<213> ORGANISM: Artificial Sequence
<220> FEATURE:
<223> OTHER INFORMATION: CD155-mIgG1-Fc fusion protein
```

<400> SEQUENCE: 69

```
Met Ala Arg Ala Met Ala Ala Ala Trp Pro Leu Leu Leu Val Ala Leu
1               5                   10                  15

Leu Val Leu Ser Trp Pro Pro Pro Gly Thr Gly Asp Val Val Val Gln
            20                  25                  30

Ala Pro Thr Gln Val Pro Gly Phe Leu Gly Asp Ser Val Thr Leu Pro
        35                  40                  45

Cys Tyr Leu Gln Val Pro Asn Met Glu Val Thr His Val Ser Gln Leu
    50                  55                  60

Thr Trp Ala Arg His Gly Glu Ser Gly Ser Met Ala Val Phe His Gln
65                  70                  75                  80

Thr Gln Gly Pro Ser Tyr Ser Glu Ser Lys Arg Leu Glu Phe Val Ala
                85                  90                  95

Ala Arg Leu Gly Ala Glu Leu Arg Asn Ala Ser Leu Arg Met Phe Gly
            100                 105                 110

Leu Arg Val Glu Asp Glu Gly Asn Tyr Thr Cys Leu Phe Val Thr Phe
        115                 120                 125

Pro Gln Gly Ser Arg Ser Val Asp Ile Trp Leu Arg Val Leu Ala Lys
    130                 135                 140

Pro Gln Asn Thr Ala Glu Val Gln Lys Val Gln Leu Thr Gly Glu Pro
145                 150                 155                 160

Val Pro Met Ala Arg Cys Val Ser Thr Gly Gly Arg Pro Pro Ala Gln
                165                 170                 175

Ile Thr Trp His Ser Asp Leu Gly Gly Met Pro Asn Thr Ser Gln Val
            180                 185                 190

Pro Gly Phe Leu Ser Gly Thr Val Thr Val Thr Ser Leu Trp Ile Leu
        195                 200                 205

Val Pro Ser Ser Gln Val Asp Gly Lys Asn Val Thr Cys Lys Val Glu
    210                 215                 220

His Glu Ser Phe Glu Lys Pro Gln Leu Leu Thr Val Asn Leu Thr Val
225                 230                 235                 240

Tyr Tyr Pro Pro Glu Val Ser Ile Ser Gly Tyr Asp Asn Asn Trp Tyr
                245                 250                 255

Leu Gly Gln Asn Glu Ala Thr Leu Thr Cys Asp Ala Arg Ser Asn Pro
            260                 265                 270

Glu Pro Thr Gly Tyr Asn Trp Ser Thr Thr Met Gly Pro Leu Pro Pro
        275                 280                 285

Phe Ala Val Ala Gln Gly Ala Gln Leu Leu Ile Arg Pro Val Asp Lys
    290                 295                 300

Pro Ile Asn Thr Thr Leu Ile Cys Asn Val Thr Asn Ala Leu Gly Ala
305                 310                 315                 320

Arg Gln Ala Glu Leu Thr Val Gln Val Lys Glu Gly Pro Pro Ser Glu
                325                 330                 335

His Ser Gly Met Ser Arg Asn Phe Ser Pro Glu Pro Arg Gly Pro Thr
            340                 345                 350

Ile Lys Pro Cys Pro Pro Cys Lys Cys Pro Ala Pro Asn Leu Leu Gly
        355                 360                 365

Gly Pro Ser Val Phe Ile Phe Pro Pro Lys Ile Lys Asp Val Leu Met
    370                 375                 380

Ile Ser Leu Ser Pro Ile Val Thr Cys Val Val Val Asp Val Ser Glu
385                 390                 395                 400

Asp Asp Pro Asp Val Gln Ile Ser Trp Phe Val Asn Asn Val Glu Val
```

```
                405                 410                 415

His Thr Ala Gln Thr Gln Thr His Arg Glu Asp Tyr Asn Ser Thr Leu
            420                 425                 430

Arg Val Val Ser Ala Leu Pro Ile Gln His Gln Asp Trp Met Ser Gly
        435                 440                 445

Lys Glu Phe Lys Cys Lys Val Asn Asn Lys Asp Leu Pro Ala Pro Ile
    450                 455                 460

Glu Arg Thr Ile Ser Lys Pro Lys Gly Ser Val Arg Ala Pro Gln Val
465                 470                 475                 480

Tyr Val Leu Pro Pro Pro Glu Glu Glu Met Thr Lys Lys Gln Val Thr
                485                 490                 495

Leu Thr Cys Met Val Thr Asp Phe Met Pro Glu Asp Ile Tyr Val Glu
            500                 505                 510

Trp Thr Asn Asn Gly Lys Thr Glu Leu Asn Tyr Lys Asn Thr Glu Pro
        515                 520                 525

Val Leu Asp Ser Asp Gly Ser Tyr Phe Met Tyr Ser Lys Leu Arg Val
    530                 535                 540

Glu Lys Lys Asn Trp Val Glu Arg Asn Ser Tyr Ser Cys Ser Val Val
545                 550                 555                 560

His Glu Gly Leu His Asn His His Thr Thr Lys Ser Phe Ser Arg Thr
                565                 570                 575

Pro Gly Lys


<210> SEQ ID NO 70
<211> LENGTH: 349
<212> TYPE: PRT
<213> ORGANISM: Artificial Sequence
<220> FEATURE:
<223> OTHER INFORMATION: CD155-his fusion protein

<400> SEQUENCE: 70

Met Ala Arg Ala Met Ala Ala Ala Trp Pro Leu Leu Leu Val Ala Leu
1               5                   10                  15

Leu Val Leu Ser Trp Pro Pro Pro Gly Thr Gly Asp Val Val Val Gln
            20                  25                  30

Ala Pro Thr Gln Val Pro Gly Phe Leu Gly Asp Ser Val Thr Leu Pro
        35                  40                  45

Cys Tyr Leu Gln Val Pro Asn Met Glu Val Thr His Val Ser Gln Leu
    50                  55                  60

Thr Trp Ala Arg His Gly Glu Ser Gly Ser Met Ala Val Phe His Gln
65                  70                  75                  80

Thr Gln Gly Pro Ser Tyr Ser Glu Ser Lys Arg Leu Glu Phe Val Ala
                85                  90                  95

Ala Arg Leu Gly Ala Glu Leu Arg Asn Ala Ser Leu Arg Met Phe Gly
            100                 105                 110

Leu Arg Val Glu Asp Glu Gly Asn Tyr Thr Cys Leu Phe Val Thr Phe
        115                 120                 125

Pro Gln Gly Ser Arg Ser Val Asp Ile Trp Leu Arg Val Leu Ala Lys
    130                 135                 140

Pro Gln Asn Thr Ala Glu Val Gln Lys Val Gln Leu Thr Gly Glu Pro
145                 150                 155                 160

Val Pro Met Ala Arg Cys Val Ser Thr Gly Gly Arg Pro Pro Ala Gln
                165                 170                 175

Ile Thr Trp His Ser Asp Leu Gly Gly Met Pro Asn Thr Ser Gln Val
            180                 185                 190
```

```
Pro Gly Phe Leu Ser Gly Thr Val Thr Val Thr Ser Leu Trp Ile Leu
        195                 200                 205

Val Pro Ser Ser Gln Val Asp Gly Lys Asn Val Thr Cys Lys Val Glu
    210                 215                 220

His Glu Ser Phe Glu Lys Pro Gln Leu Leu Thr Val Asn Leu Thr Val
225                 230                 235                 240

Tyr Tyr Pro Pro Glu Val Ser Ile Ser Gly Tyr Asp Asn Asn Trp Tyr
                245                 250                 255

Leu Gly Gln Asn Glu Ala Thr Leu Thr Cys Asp Ala Arg Ser Asn Pro
            260                 265                 270

Glu Pro Thr Gly Tyr Asn Trp Ser Thr Thr Met Gly Pro Leu Pro Pro
        275                 280                 285

Phe Ala Val Ala Gln Gly Ala Gln Leu Leu Ile Arg Pro Val Asp Lys
    290                 295                 300

Pro Ile Asn Thr Thr Leu Ile Cys Asn Val Thr Asn Ala Leu Gly Ala
305                 310                 315                 320

Arg Gln Ala Glu Leu Thr Val Gln Val Lys Glu Gly Pro Pro Ser Glu
                325                 330                 335

His Ser Gly Met Ser Arg Asn His His His His His His
            340                 345


<210> SEQ ID NO 71
<211> LENGTH: 130
<212> TYPE: PRT
<213> ORGANISM: Artificial Sequence
<220> FEATURE:
<223> OTHER INFORMATION: Heavy chain variable region of 22G2

<400> SEQUENCE: 71

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Ile Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Tyr Tyr Val Ser Gly Asn Tyr Tyr Asn Val Asp Tyr
            100                 105                 110

Tyr Phe Phe Gly Val Asp Val Trp Gly Gln Gly Thr Thr Val Thr Val
        115                 120                 125

Ser Ser
    130


<210> SEQ ID NO 72
<211> LENGTH: 109
<212> TYPE: PRT
<213> ORGANISM: Artificial Sequence
<220> FEATURE:
<223> OTHER INFORMATION: Light chain variable region of 22G2

<400> SEQUENCE: 72

Glu Ile Val Leu Thr Gln Ser Pro Ala Thr Leu Ser Leu Ser Pro Gly
```

```
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Leu Phe Thr Phe Gly Pro Gly Thr Lys Val Asp Ile Lys
            100                 105


<210> SEQ ID NO 73
<211> LENGTH: 244
<212> TYPE: PRT
<213> ORGANISM: Artificial Sequence
<220> FEATURE:
<223> OTHER INFORMATION: TIGIT protein

<400> SEQUENCE: 73

Met Arg Trp Cys Leu Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Glu Lys Gly Gly Ser Ile Ile Leu Gln Cys His Leu Ser
        35                  40                  45

Ser Thr Thr Ala Gln Val Thr Gln Val Asn Trp Glu Gln Gln Asp Gln
    50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95

Ser Leu Thr Val Asn Asp Thr Gly Glu Tyr Phe Cys Ile Tyr His Thr
            100                 105                 110

Tyr Pro Asp Gly Thr Tyr Thr Gly Arg Ile Phe Leu Glu Val Leu Glu
        115                 120                 125

Ser Ser Val Ala Glu His Gly Ala Arg Phe Gln Ile Pro Leu Leu Gly
    130                 135                 140

Ala Met Ala Ala Thr Leu Val Val Ile Cys Thr Ala Val Ile Val Val
145                 150                 155                 160

Val Ala Leu Thr Arg Lys Lys Lys Ala Leu Arg Ile His Ser Val Glu
                165                 170                 175

Gly Asp Leu Arg Arg Lys Ser Ala Gly Gln Glu Glu Trp Ser Pro Ser
            180                 185                 190

Ala Pro Ser Pro Pro Gly Ser Cys Val Gln Ala Glu Ala Ala Pro Ala
        195                 200                 205

Gly Leu Cys Gly Glu Gln Arg Gly Glu Asp Cys Ala Glu Leu His Asp
    210                 215                 220

Tyr Phe Asn Val Leu Ser Tyr Arg Ser Leu Gly Asn Cys Ser Phe Phe
225                 230                 235                 240

Thr Glu Thr Gly


<210> SEQ ID NO 74
```

```
<211> LENGTH: 417
<212> TYPE: PRT
<213> ORGANISM: Artificial Sequence
<220> FEATURE:
<223> OTHER INFORMATION: CD155 protein

<400> SEQUENCE: 74

Met Ala Arg Ala Met Ala Ala Ala Trp Pro Leu Leu Leu Val Ala Leu
1               5                   10                  15

Leu Val Leu Ser Trp Pro Pro Pro Gly Thr Gly Asp Val Val Val Gln
            20                  25                  30

Ala Pro Thr Gln Val Pro Gly Phe Leu Gly Asp Ser Val Thr Leu Pro
        35                  40                  45

Cys Tyr Leu Gln Val Pro Asn Met Glu Val Thr His Val Ser Gln Leu
    50                  55                  60

Thr Trp Ala Arg His Gly Glu Ser Gly Ser Met Ala Val Phe His Gln
65                  70                  75                  80

Thr Gln Gly Pro Ser Tyr Ser Glu Ser Lys Arg Leu Glu Phe Val Ala
                85                  90                  95

Ala Arg Leu Gly Ala Glu Leu Arg Asn Ala Ser Leu Arg Met Phe Gly
            100                 105                 110

Leu Arg Val Glu Asp Glu Gly Asn Tyr Thr Cys Leu Phe Val Thr Phe
        115                 120                 125

Pro Gln Gly Ser Arg Ser Val Asp Ile Trp Leu Arg Val Leu Ala Lys
    130                 135                 140

Pro Gln Asn Thr Ala Glu Val Gln Lys Val Gln Leu Thr Gly Glu Pro
145                 150                 155                 160

Val Pro Met Ala Arg Cys Val Ser Thr Gly Gly Arg Pro Pro Ala Gln
                165                 170                 175

Ile Thr Trp His Ser Asp Leu Gly Gly Met Pro Asn Thr Ser Gln Val
            180                 185                 190

Pro Gly Phe Leu Ser Gly Thr Val Thr Val Thr Ser Leu Trp Ile Leu
        195                 200                 205

Val Pro Ser Ser Gln Val Asp Gly Lys Asn Val Thr Cys Lys Val Glu
    210                 215                 220

His Glu Ser Phe Glu Lys Pro Gln Leu Leu Thr Val Asn Leu Thr Val
225                 230                 235                 240

Tyr Tyr Pro Pro Glu Val Ser Ile Ser Gly Tyr Asp Asn Asn Trp Tyr
                245                 250                 255

Leu Gly Gln Asn Glu Ala Thr Leu Thr Cys Asp Ala Arg Ser Asn Pro
            260                 265                 270

Glu Pro Thr Gly Tyr Asn Trp Ser Thr Thr Met Gly Pro Leu Pro Pro
        275                 280                 285

Phe Ala Val Ala Gln Gly Ala Gln Leu Leu Ile Arg Pro Val Asp Lys
    290                 295                 300

Pro Ile Asn Thr Thr Leu Ile Cys Asn Val Thr Asn Ala Leu Gly Ala
305                 310                 315                 320

Arg Gln Ala Glu Leu Thr Val Gln Val Lys Glu Gly Pro Pro Ser Glu
                325                 330                 335

His Ser Gly Met Ser Arg Asn Ala Ile Ile Phe Leu Val Leu Gly Ile
            340                 345                 350

Leu Val Phe Leu Ile Leu Leu Gly Ile Gly Ile Tyr Phe Tyr Trp Ser
        355                 360                 365

Lys Cys Ser Arg Glu Val Leu Trp His Cys His Leu Cys Pro Ser Ser
    370                 375                 380
```

```
Thr Glu His Ala Ser Ala Ser Ala Asn Gly His Val Ser Tyr Ser Ala
385                 390                 395                 400

Val Ser Arg Glu Asn Ser Ser Ser Gln Asp Pro Gln Thr Glu Gly Thr
                405                 410                 415

Arg


<210> SEQ ID NO 75
<211> LENGTH: 126
<212> TYPE: PRT
<213> ORGANISM: Artificial Sequence
<220> FEATURE:
<223> OTHER INFORMATION: Heavy chain variable region

<400> SEQUENCE: 75

Gln Val Thr Leu Lys Glu Ser Gly Pro Gly Ile Leu Gln Pro Ser Gln
1               5                   10                  15

Thr Leu Ser Leu Thr Cys Thr Phe Ser Gly Phe Ser Leu Arg Thr Tyr
            20                  25                  30

Gly Leu Gly Val Gly Trp Ile Arg Gln Leu Ser Gly Lys Gly Leu Glu
        35                  40                  45

Trp Leu Ala Asn Ile Trp Trp Asp Asp Asp Glu Tyr Tyr Asn Pro Ser
    50                  55                  60

Leu Lys Asn Arg Leu Thr Ile Ser Lys Asp Thr Ser Asn Asn Gln Ala
65                  70                  75                  80

Phe Leu Lys Ile Thr Asn Val Asp Thr Ala Asp Thr Ala Thr Tyr Tyr
                85                  90                  95

Cys Ala Arg Ile Ala Arg Pro His Tyr Tyr Trp Asp Gly Arg Tyr Ile
            100                 105                 110

Leu Asp Val Trp Gly Gln Gly Ala Ser Val Thr Val Ser Ser
        115                 120                 125


<210> SEQ ID NO 76
<211> LENGTH: 126
<212> TYPE: PRT
<213> ORGANISM: Artificial Sequence
<220> FEATURE:
<223> OTHER INFORMATION: Heavy chain variable region

<400> SEQUENCE: 76

Glu Val Gln Leu Val Glu Ser Glu Gly Gly Leu Val Gln Pro Gly Ala
1               5                   10                  15

Ser Val Lys Leu Ser Cys Val Gly Ser Gly Phe Ser Phe Ser Asp His
            20                  25                  30

Trp Met Ser Trp Val Arg Gln Thr Pro Gly Lys Thr Met Glu Trp Ile
        35                  40                  45

Gly Asn Ile Gln Tyr Asp Gly Ser Tyr Thr Asn Tyr Ala Pro Ser Leu
    50                  55                  60

Lys Asn Arg Phe Thr Ile Ser Arg Asp Asn Ala Lys Asn Thr Leu Tyr
65                  70                  75                  80

Leu Gln Met Thr Asn Leu Arg Ser Glu Asp Thr Ala Thr Tyr Tyr Cys
                85                  90                  95

Thr Arg Gly His Phe Arg Ile Thr Met Ala Ser Met Gly Ala Ser Ala
            100                 105                 110

Ser Val Tyr Trp Gly Gln Gly Val Met Val Thr Val Ser Ser
        115                 120                 125


<210> SEQ ID NO 77
```

<211> LENGTH: 112
<212> TYPE: PRT
<213> ORGANISM: Artificial Sequence
<220> FEATURE:
<223> OTHER INFORMATION: Light chain variable region

<400> SEQUENCE: 77

```
Asp Ile Met Met Thr Gln Ser Pro Leu Ser Val Ala Val Thr Pro Gly
1               5                   10                  15

Glu Ser Ala Ser Ile Ser Cys Arg Ser Ser Lys Ser Leu Leu His Ser
            20                  25                  30

Asn Gly Ile Thr Tyr Leu Ser Trp Tyr Leu Gln Arg Pro Glu Lys Ser
        35                  40                  45

Pro Gln Leu Leu Ile Phe Gln Ile Ser Asn Leu Ala Ser Gly Val Ser
    50                  55                  60

Asp Arg Phe Ser Gly Ser Gly Ser Gly Thr Asp Phe Thr Leu Ile Ile
65                  70                  75                  80

Ser Lys Val Glu Thr Glu Asp Val Gly Ile Tyr Tyr Cys Met Gln Phe
                85                  90                  95

Leu Glu Val Pro Tyr Thr Phe Gly Ala Gly Thr Lys Leu Glu Leu Lys
            100                 105                 110
```

<210> SEQ ID NO 78
<211> LENGTH: 107
<212> TYPE: PRT
<213> ORGANISM: Artificial Sequence
<220> FEATURE:
<223> OTHER INFORMATION: Light chain variable region

<400> SEQUENCE: 78

```
Asp Ile Gln Met Thr Gln Ser Pro Ser Ser Leu Pro Thr Ser Leu Gly
1               5                   10                  15

Asp Arg Val Thr Ile Thr Cys Arg Thr Ser Gln Asp Ile Gly Asn Ser
            20                  25                  30

Leu Arg Trp Phe Gln Gln Lys Pro Gly Lys Ser Pro Arg Leu Met Ile
        35                  40                  45

His Gly Ala Thr Asn Leu Ala Asn Gly Val Pro Ser Arg Phe Ser Gly
    50                  55                  60

Ser Arg Ala Gly Ser Asp Tyr Ser Leu Thr Ile Asn Ser Leu Glu Ser
65                  70                  75                  80

Glu Asp Met Ala Met Tyr Tyr Cys Leu Gln His Asn Glu Tyr Pro Leu
                85                  90                  95

Thr Phe Gly Ser Gly Thr Lys Leu Glu Ile Lys
            100                 105
```

<210> SEQ ID NO 79
<211> LENGTH: 126
<212> TYPE: PRT
<213> ORGANISM: Artificial Sequence
<220> FEATURE:
<223> OTHER INFORMATION: Heavy chain variable region

<400> SEQUENCE: 79

```
Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Thr Tyr
            20                  25                  30

Gly Leu Gly Val Gly Trp Ile Arg Gln Pro Pro Gly Lys Ala Leu Glu
        35                  40                  45
```

```
Trp Leu Ala Asn Ile Trp Trp Asp Asp Asp Glu Tyr Tyr Asn Pro Ser
    50                  55                  60

Leu Lys Asn Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Ile Ala Arg Pro His Tyr Tyr Trp Asp Gly Arg Tyr Ile
            100                 105                 110

Leu Asp Val Trp Gly Gln Gly Thr Thr Val Thr Val Ser Ser
        115                 120                 125


<210> SEQ ID NO 80
<211> LENGTH: 126
<212> TYPE: PRT
<213> ORGANISM: Artificial Sequence
<220> FEATURE:
<223> OTHER INFORMATION: Heavy chain variable region

<400> SEQUENCE: 80

Gln Val Thr Leu Lys Glu Ser Gly Pro Val Leu Val Lys Pro Thr Glu
1               5                   10                  15

Thr Leu Thr Leu Thr Cys Thr Phe Ser Gly Phe Ser Leu Ser Thr Tyr
            20                  25                  30

Gly Leu Gly Val Gly Trp Ile Arg Gln Pro Pro Gly Lys Ala Leu Glu
        35                  40                  45

Trp Leu Ala Asn Ile Trp Trp Asp Asp Asp Glu Tyr Tyr Asn Pro Ser
    50                  55                  60

Leu Lys Asn Arg Leu Thr Ile Ser Lys Asp Thr Ser Lys Ser Gln Ala
65                  70                  75                  80

Val Leu Thr Met Thr Asn Met Asp Pro Val Asp Thr Ala Thr Tyr Tyr
                85                  90                  95

Cys Ala Arg Ile Ala Arg Pro His Tyr Tyr Trp Asp Gly Arg Tyr Ile
            100                 105                 110

Leu Asp Val Trp Gly Gln Gly Thr Thr Val Thr Val Ser Ser
        115                 120                 125


<210> SEQ ID NO 81
<211> LENGTH: 126
<212> TYPE: PRT
<213> ORGANISM: Artificial Sequence
<220> FEATURE:
<223> OTHER INFORMATION: Heavy chain variable region

<400> SEQUENCE: 81

Gln Val Thr Leu Lys Glu Ser Gly Pro Val Leu Val Lys Pro Thr Glu
1               5                   10                  15

Thr Leu Thr Leu Thr Cys Thr Phe Ser Gly Phe Ser Leu Arg Thr Tyr
            20                  25                  30

Gly Leu Gly Val Gly Trp Ile Arg Gln Pro Pro Gly Lys Ala Leu Glu
        35                  40                  45

Trp Leu Ala Asn Ile Trp Trp Asp Asp Asp Glu Tyr Tyr Asn Pro Ser
    50                  55                  60

Leu Lys Asn Arg Leu Thr Ile Ser Lys Asp Thr Ser Lys Ser Gln Ala
65                  70                  75                  80

Val Leu Thr Met Thr Asn Met Asp Pro Val Asp Thr Ala Thr Tyr Tyr
                85                  90                  95

Cys Ala Arg Ile Ala Arg Pro His Tyr Tyr Trp Asp Gly Arg Tyr Ile
            100                 105                 110
```

```
Leu Asp Val Trp Gly Gln Gly Thr Thr Val Thr Val Ser Ser
        115                 120                 125


<210> SEQ ID NO 82
<211> LENGTH: 126
<212> TYPE: PRT
<213> ORGANISM: Artificial Sequence
<220> FEATURE:
<223> OTHER INFORMATION: Heavy chain variable region

<400> SEQUENCE: 82

Gln Val Thr Leu Lys Glu Ser Gly Pro Val Leu Val Lys Pro Thr Glu
1               5                   10                  15

Thr Leu Thr Leu Thr Cys Thr Phe Ser Gly Phe Ser Leu Ser Thr Tyr
            20                  25                  30

Gly Leu Gly Val Gly Trp Ile Arg Gln Pro Pro Gly Lys Ala Leu Glu
        35                  40                  45

Trp Leu Ala Asn Ile Trp Trp Asp Asp Asp Glu Tyr Tyr Asn Pro Ser
    50                  55                  60

Leu Lys Asn Arg Leu Thr Ile Ser Lys Asp Thr Ser Lys Ser Gln Ala
65                  70                  75                  80

Val Leu Thr Ile Thr Asn Val Asp Pro Val Asp Thr Ala Thr Tyr Tyr
                85                  90                  95

Cys Ala Arg Ile Ala Arg Pro His Tyr Tyr Trp Asp Gly Arg Tyr Ile
            100                 105                 110

Leu Asp Val Trp Gly Gln Gly Thr Thr Val Thr Val Ser Ser
        115                 120                 125


<210> SEQ ID NO 83
<211> LENGTH: 126
<212> TYPE: PRT
<213> ORGANISM: Artificial Sequence
<220> FEATURE:
<223> OTHER INFORMATION: Heavy chain variable region

<400> SEQUENCE: 83

Gln Val Thr Leu Lys Glu Ser Gly Pro Val Leu Val Lys Pro Thr Glu
1               5                   10                  15

Thr Leu Thr Leu Thr Cys Thr Phe Ser Gly Phe Ser Leu Arg Thr Tyr
            20                  25                  30

Gly Leu Gly Val Gly Trp Ile Arg Gln Pro Pro Gly Lys Ala Leu Glu
        35                  40                  45

Trp Leu Ala Asn Ile Trp Trp Asp Asp Asp Glu Tyr Tyr Asn Pro Ser
    50                  55                  60

Leu Lys Asn Arg Leu Thr Ile Ser Lys Asp Thr Ser Lys Ser Gln Ala
65                  70                  75                  80

Val Leu Thr Ile Thr Asn Val Asp Pro Val Asp Thr Ala Thr Tyr Tyr
                85                  90                  95

Cys Ala Arg Ile Ala Arg Pro His Tyr Tyr Trp Asp Gly Arg Tyr Ile
            100                 105                 110

Leu Asp Val Trp Gly Gln Gly Thr Thr Val Thr Val Ser Ser
        115                 120                 125


<210> SEQ ID NO 84
<211> LENGTH: 112
<212> TYPE: PRT
<213> ORGANISM: Artificial Sequence
<220> FEATURE:
<223> OTHER INFORMATION: Light chain variable region
```

```
<400> SEQUENCE: 84

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Ser Trp Tyr Leu Gln Lys Pro Gly Gln Ser
        35                  40                  45

Pro Gln Leu Leu Ile Tyr Gln Ile Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Phe
                85                  90                  95

Leu Glu Val Pro Tyr Thr Phe Gly Gln Gly Thr Lys Leu Glu Ile Lys
            100                 105                 110


<210> SEQ ID NO 85
<211> LENGTH: 112
<212> TYPE: PRT
<213> ORGANISM: Artificial Sequence
<220> FEATURE:
<223> OTHER INFORMATION: Light chain variable region

<400> SEQUENCE: 85

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Ser Trp Tyr Leu Gln Lys Pro Gly Gln Ser
        35                  40                  45

Pro Gln Leu Leu Ile Phe Gln Ile Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Phe
                85                  90                  95

Leu Glu Val Pro Tyr Thr Phe Gly Gln Gly Thr Lys Leu Glu Ile Lys
            100                 105                 110


<210> SEQ ID NO 86
<211> LENGTH: 112
<212> TYPE: PRT
<213> ORGANISM: Artificial Sequence
<220> FEATURE:
<223> OTHER INFORMATION: Light chain variable region

<400> SEQUENCE: 86

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Ser Trp Tyr Leu Gln Lys Pro Glu Lys Ser
        35                  40                  45

Pro Gln Leu Leu Ile Phe Gln Ile Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80
```

```
Ser Arg Val Glu Ala Glu Asp Val Gly Val Tyr Tyr Cys Met Gln Phe
                85                  90                  95

Leu Glu Val Pro Tyr Thr Phe Gly Gln Gly Thr Lys Leu Glu Ile Lys
            100                 105                 110


<210> SEQ ID NO 87
<211> LENGTH: 112
<212> TYPE: PRT
<213> ORGANISM: Artificial Sequence
<220> FEATURE:
<223> OTHER INFORMATION: Light chain variable region

<400> SEQUENCE: 87

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Ser Trp Tyr Leu Gln Lys Pro Glu Lys Ser
        35                  40                  45

Pro Gln Leu Leu Ile Phe Gln Ile Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Phe
                85                  90                  95

Leu Glu Val Pro Tyr Thr Phe Gly Gln Gly Thr Lys Leu Glu Ile Lys
            100                 105                 110


<210> SEQ ID NO 88
<211> LENGTH: 126
<212> TYPE: PRT
<213> ORGANISM: Artificial Sequence
<220> FEATURE:
<223> OTHER INFORMATION: Heavy chain variable region

<400> SEQUENCE: 88

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Trp Met Ser Trp Val Arg Gln Ala Pro Gly Lys Gly Leu Glu Trp Val
        35                  40                  45

Ala Asn Ile Gln Tyr Asp Gly Ser Tyr Thr Asn Tyr Ala Pro Ser Leu
    50                  55                  60

Lys Asn Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Phe Arg Ile Thr Met Ala Ser Met Gly Ala Ser Ala
            100                 105                 110

Ser Val Tyr Trp Gly Gln Gly Thr Met Val Thr Val Ser Ser
        115                 120                 125


<210> SEQ ID NO 89
<211> LENGTH: 126
<212> TYPE: PRT
<213> ORGANISM: Artificial Sequence
<220> FEATURE:
<223> OTHER INFORMATION: Heavy chain variable region
```

<400> SEQUENCE: 89

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Trp Met Ser Trp Val Arg Gln Ala Pro Gly Lys Gly Leu Glu Trp Ile
        35                  40                  45

Ala Asn Ile Gln Tyr Asp Gly Ser Tyr Thr Asn Tyr Ala Pro Ser Leu
    50                  55                  60

Lys Asn Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Phe Arg Ile Thr Met Ala Ser Met Gly Ala Ser Ala
            100                 105                 110

Ser Val Tyr Trp Gly Gln Gly Thr Met Val Thr Val Ser Ser
        115                 120                 125
```

<210> SEQ ID NO 90
<211> LENGTH: 126
<212> TYPE: PRT
<213> ORGANISM: Artificial Sequence
<220> FEATURE:
<223> OTHER INFORMATION: Heavy chain variable region

<400> SEQUENCE: 90

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Trp Met Ser Trp Val Arg Gln Ala Pro Gly Lys Gly Met Glu Trp Ile
        35                  40                  45

Ala Asn Ile Gln Tyr Asp Gly Ser Tyr Thr Asn Tyr Ala Pro Ser Leu
    50                  55                  60

Lys Asn Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Phe Arg Ile Thr Met Ala Ser Met Gly Ala Ser Ala
            100                 105                 110

Ser Val Tyr Trp Gly Gln Gly Thr Met Val Thr Val Ser Ser
        115                 120                 125
```

<210> SEQ ID NO 91
<211> LENGTH: 126
<212> TYPE: PRT
<213> ORGANISM: Artificial Sequence
<220> FEATURE:
<223> OTHER INFORMATION: Heavy chain variable region

<400> SEQUENCE: 91

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Trp Met Ser Trp Val Arg Gln Ala Pro Gly Lys Gly Met Glu Trp Ile
        35                  40                  45
```

```
Ala Asn Ile Gln Tyr Asp Gly Ser Tyr Thr Asn Tyr Ala Pro Ser Leu
    50                  55                  60

Lys Asn Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg Gly His Phe Arg Ile Thr Met Ala Ser Met Gly Ala Ser Ala
            100                 105                 110

Ser Val Tyr Trp Gly Gln Gly Thr Met Val Thr Val Ser Ser
        115                 120                 125


<210> SEQ ID NO 92
<211> LENGTH: 126
<212> TYPE: PRT
<213> ORGANISM: Artificial Sequence
<220> FEATURE:
<223> OTHER INFORMATION: Heavy chain variable region

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Trp Met Ser Trp Val Arg Gln Ala Pro Gly Lys Thr Met Glu Trp Ile
        35                  40                  45

Gly Asn Ile Gln Tyr Asp Gly Ser Tyr Thr Asn Tyr Ala Pro Ser Leu
    50                  55                  60

Lys Asn Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Thr Tyr Tyr Cys
                85                  90                  95

Thr Arg Gly His Phe Arg Ile Thr Met Ala Ser Met Gly Ala Ser Ala
            100                 105                 110

Ser Val Tyr Trp Gly Gln Gly Thr Met Val Thr Val Ser Ser
        115                 120                 125


<210> SEQ ID NO 93
<211> LENGTH: 107
<212> TYPE: PRT
<213> ORGANISM: Artificial Sequence
<220> FEATURE:
<223> OTHER INFORMATION: Light chain variable region

<400> SEQUENCE: 93

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Gly Asn Ser
            20                  25                  30

Leu Arg Trp Tyr Gln Gln Lys Pro Gly Lys Ala Pro Lys Leu Leu Ile
        35                  40                  45

Tyr Gly Ala Thr Asn Leu Ala Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asn Glu Tyr Pro Leu
                85                  90                  95

Thr Phe Gly Gln Gly Thr Lys Leu Glu Ile Lys
```

```
            100                 105


<210> SEQ ID NO 94
<211> LENGTH: 107
<212> TYPE: PRT
<213> ORGANISM: Artificial Sequence
<220> FEATURE:
<223> OTHER INFORMATION: Light chain variable region

<400> SEQUENCE: 94

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Gly Asn Ser
            20                  25                  30

Leu Arg Trp Tyr Gln Gln Lys Pro Gly Lys Ala Pro Lys Leu Leu Ile
        35                  40                  45

His Gly Ala Thr Asn Leu Ala Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asn Glu Tyr Pro Leu
                85                  90                  95

Thr Phe Gly Gln Gly Thr Lys Leu Glu Ile Lys
            100                 105


<210> SEQ ID NO 95
<211> LENGTH: 107
<212> TYPE: PRT
<213> ORGANISM: Artificial Sequence
<220> FEATURE:
<223> OTHER INFORMATION: Light chain variable region

<400> SEQUENCE: 95

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Gly Asn Ser
            20                  25                  30

Leu Arg Trp Tyr Gln Gln Lys Pro Gly Lys Ala Pro Lys Leu Leu Ile
        35                  40                  45

His Gly Ala Thr Asn Leu Ala Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asn Glu Tyr Pro Leu
                85                  90                  95

Thr Phe Gly Gln Gly Thr Lys Leu Glu Ile Lys
            100                 105


<210> SEQ ID NO 96
<211> LENGTH: 107
<212> TYPE: PRT
<213> ORGANISM: Artificial Sequence
<220> FEATURE:
<223> OTHER INFORMATION: Light chain variable region

<400> SEQUENCE: 96

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Gly Asn Ser
            20                  25                  30
```

```
Leu Arg Trp Phe Gln Gln Lys Pro Gly Lys Ala Pro Arg Leu Met Ile
        35                  40                  45

His Gly Ala Thr Asn Leu Ala Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asn Glu Tyr Pro Leu
                85                  90                  95

Thr Phe Gly Gln Gly Thr Lys Leu Glu Ile Lys
            100                 105


<210> SEQ ID NO 97
<211> LENGTH: 107
<212> TYPE: PRT
<213> ORGANISM: Artificial Sequence
<220> FEATURE:
<223> OTHER INFORMATION: Light chain variable region

<400> SEQUENCE: 97

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Gly Asn Ser
            20                  25                  30

Leu Arg Trp Phe Gln Gln Lys Pro Gly Lys Ala Pro Arg Leu Met Ile
        35                  40                  45

His Gly Ala Thr Asn Leu Ala Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Met Tyr Tyr Cys Leu Gln His Asn Glu Tyr Pro Leu
                85                  90                  95

Thr Phe Gly Gln Gly Thr Lys Leu Glu Ile Lys
            100                 105


<210> SEQ ID NO 98
<211> LENGTH: 126
<212> TYPE: PRT
<213> ORGANISM: Artificial Sequence
<220> FEATURE:
<223> OTHER INFORMATION: Heavy chain variable region of SHS006-T-Hu17-31

<400> SEQUENCE: 98

Gln Val Thr Leu Lys Glu Ser Gly Pro Val Leu Val Lys Pro Thr Glu
1               5                   10                  15

Thr Leu Thr Leu Thr Cys Thr Phe Ser Gly Phe Ser Leu Arg Thr Tyr
            20                  25                  30

Gly Leu Gly Val Gly Trp Ile Arg Gln Pro Pro Gly Lys Ala Leu Glu
        35                  40                  45

Trp Leu Ala Asn Ile Trp Trp Asp Asp Asp Glu Tyr Tyr Asn Pro Ser
    50                  55                  60

Leu Lys Asn Arg Leu Thr Ile Ser Lys Asp Thr Ser Lys Ser Gln Ala
65                  70                  75                  80

Val Leu Thr Met Thr Asn Met Asp Pro Val Asp Thr Ala Thr Tyr Tyr
                85                  90                  95

Cys Ala Arg Ile Ala Arg Pro His Tyr Tyr Trp Asp Gly Arg Tyr Ile
            100                 105                 110

Leu Asp Val Trp Gly Gln Gly Thr Thr Val Thr Val Ser Ser
```

115 120 125

<210> SEQ ID NO 99
<211> LENGTH: 126
<212> TYPE: PRT
<213> ORGANISM: Artificial Sequence
<220> FEATURE:
<223> OTHER INFORMATION: Heavy chain variable region of SHS006-T-Hu23-53

<400> SEQUENCE: 99

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Trp Met Ser Trp Val Arg Gln Ala Pro Gly Lys Thr Met Glu Trp Ile
        35                  40                  45

Gly Asn Ile Gln Tyr Asp Gly Ser Tyr Thr Asn Tyr Ala Pro Ser Leu
    50                  55                  60

Lys Asn Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Thr Tyr Tyr Cys
                85                  90                  95

Thr Arg Gly His Phe Arg Ile Thr Met Ala Ser Met Gly Ala Ser Ala
            100                 105                 110

Ser Val Tyr Trp Gly Gln Gly Thr Met Val Thr Val Ser Ser
        115                 120                 125
```

<210> SEQ ID NO 100
<211> LENGTH: 112
<212> TYPE: PRT
<213> ORGANISM: Artificial Sequence
<220> FEATURE:
<223> OTHER INFORMATION: Light chain variable region of SHS006-T-Hu17-31

<400> SEQUENCE: 100

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Ser Trp Tyr Leu Gln Lys Pro Gly Gln Ser
        35                  40                  45

Pro Gln Leu Leu Ile Tyr Gln Ile Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Phe
                85                  90                  95

Leu Glu Val Pro Tyr Thr Phe Gly Gln Gly Thr Lys Leu Glu Ile Lys
            100                 105                 110
```

<210> SEQ ID NO 101
<211> LENGTH: 107
<212> TYPE: PRT
<213> ORGANISM: Artificial Sequence
<220> FEATURE:
<223> OTHER INFORMATION: Light chain variable region of SHS006-T-Hu23-53

<400> SEQUENCE: 101

```
Asp Ile Gln Met Thr Gln Ser Pro Ser Ser Leu Ser Ala Ser Val Gly
1               5                   10                  15
```

```
Asp Arg Val Thr Ile Thr Cys Arg Thr Ser Gln Asp Ile Gly Asn Ser
            20                  25                  30

Leu Arg Trp Phe Gln Gln Lys Pro Gly Lys Ala Pro Lys Leu Leu Ile
        35                  40                  45

His Gly Ala Thr Asn Leu Ala Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asn Glu Tyr Pro Leu
                85                  90                  95

Thr Phe Gly Gln Gly Thr Lys Leu Glu Ile Lys
            100                 105


<210> SEQ ID NO 102
<211> LENGTH: 707
<212> TYPE: PRT
<213> ORGANISM: Artificial Sequence
<220> FEATURE:
<223> OTHER INFORMATION: ScFab-T2353-Knob-PHR protein

<400> SEQUENCE: 102

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Gly Asn Ser
            20                  25                  30

Leu Arg Trp Phe Gln Gln Lys Pro Gly Lys Ala Pro Lys Leu Leu Ile
        35                  40                  45

His Gly Ala Thr Asn Leu Ala Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asn Glu Tyr Pro Leu
                85                  90                  95

Thr Phe Gly Cys Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Gly Gly Gly Gly Ser
    210                 215                 220

Gly Gly Gly Gly Ser Gly Gly Gly Gly Ser Gly Gly Gly Gly Ser Gly
225                 230                 235                 240

Gly Gly Gly Ser Gly Gly Gly Gly Ser Gly Gly Gly Gly Ser Glu Val
                245                 250                 255

Gln Leu Val Glu Ser Gly Gly Gly Leu Val Gln Pro Gly Gly Ser Leu
            260                 265                 270
```

```
Arg Leu Ser Cys Ala Ala Ser Gly Phe Thr Phe Ser Asp His Trp Met
        275                 280                 285

Ser Trp Val Arg Gln Ala Pro Gly Lys Cys Met Glu Trp Ile Gly Asn
    290                 295                 300

Ile Gln Tyr Asp Gly Ser Tyr Thr Asn Tyr Ala Pro Ser Leu Lys Asn
305                 310                 315                 320

Arg Phe Thr Ile Ser Arg Asp Asn Ala Lys Asn Ser Leu Tyr Leu Gln
                325                 330                 335

Met Asn Ser Leu Arg Ala Glu Asp Thr Ala Thr Tyr Tyr Cys Thr Arg
            340                 345                 350

Gly His Phe Arg Ile Thr Met Ala Ser Met Gly Ala Ser Ala Ser Val
        355                 360                 365

Tyr Trp Gly Gln Gly Thr Met Val Thr Val Ser Ser Ala Ser Thr Lys
    370                 375                 380

Gly Pro Ser Val Phe Pro Leu Ala Pro Cys Ser Arg Ser Thr Ser Glu
385                 390                 395                 400

Ser Thr Ala Ala Leu Gly Cys Leu Val Lys Asp Tyr Phe Pro Glu Pro
                405                 410                 415

Val Thr Val Ser Trp Asn Ser Gly Ala Leu Thr Ser Gly Val His Thr
            420                 425                 430

Phe Pro Ala Val Leu Gln Ser Ser Gly Leu Tyr Ser Leu Ser Ser Val
        435                 440                 445

Val Thr Val Pro Ser Ser Ser Leu Gly Thr Lys Thr Tyr Thr Cys Asn
    450                 455                 460

Val Asp His Lys Pro Ser Asn Thr Lys Val Asp Lys Arg Val Glu Ser
465                 470                 475                 480

Lys Tyr Gly Pro Pro Cys Pro Pro Cys Pro Ala Pro Glu Phe Leu Gly
                485                 490                 495

Gly Pro Ser Val Phe Leu Phe Pro Pro Lys Pro Lys Asp Thr Leu Met
            500                 505                 510

Ile Ser Arg Thr Pro Glu Val Thr Cys Val Val Val Asp Val Ser Gln
        515                 520                 525

Glu Asp Pro Glu Val Gln Phe Asn Trp Tyr Val Asp Gly Val Glu Val
    530                 535                 540

His Asn Ala Lys Thr Lys Pro Arg Glu Glu Gln Phe Asn Ser Thr Tyr
545                 550                 555                 560

Arg Val Val Ser Val Leu Thr Val Leu His Gln Asp Trp Leu Asn Gly
                565                 570                 575

Lys Glu Tyr Lys Cys Lys Val Ser Asn Lys Gly Leu Pro Ser Ser Ile
            580                 585                 590

Glu Lys Thr Ile Ser Lys Ala Lys Gly Gln Pro Arg Glu Pro Gln Val
        595                 600                 605

Tyr Thr Leu Pro Pro Cys Gln Glu Glu Met Thr Lys Asn Gln Val Ser
    610                 615                 620

Leu Trp Cys Leu Val Lys Gly Phe Tyr Pro Ser Asp Ile Ala Val Glu
625                 630                 635                 640

Trp Glu Ser Asn Gly Gln Pro Glu Asn Asn Tyr Lys Thr Thr Pro Pro
                645                 650                 655

Val Leu Asp Ser Asp Gly Ser Phe Phe Leu Tyr Ser Arg Leu Thr Val
            660                 665                 670

Asp Lys Ser Arg Trp Gln Glu Gly Asn Val Phe Ser Cys Ser Val Met
        675                 680                 685
```

```
His Glu Ala Leu His Asn His Tyr Thr Gln Lys Ser Leu Ser Leu Ser
    690                 695                 700

Leu Gly Lys
705


<210> SEQ ID NO 103
<211> LENGTH: 705
<212> TYPE: PRT
<213> ORGANISM: Artificial Sequence
<220> FEATURE:
<223> OTHER INFORMATION: HuPL721-scfab-hole-PHR protein

<400> SEQUENCE: 103

Asp Ile Val Met Thr Gln Ser Pro Asp Ser Leu Ala Val Ser Leu Gly
1               5                   10                  15

Glu Arg Ala Thr Ile Ser Cys Lys Ser Ser Gln Ser Leu Leu Tyr Ser
            20                  25                  30

Ser Asn Gln Lys Asn Ser Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Gly Tyr Pro Leu Thr Phe Gly Cys Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys Gly Gly Gly Gly
    210                 215                 220

Ser Gly Gly Gly Gly Ser Gly Gly Gly Gly Ser Gly Gly Gly Gly Ser
225                 230                 235                 240

Gly Gly Gly Gly Ser Gly Gly Gly Gly Ser Gly Gly Gly Gly Ser Gly
                245                 250                 255

Gly Gly Gly Ser Gln Val Gln Leu Gln Glu Ser Gly Pro Gly Leu Val
            260                 265                 270

Lys Pro Ser Gln Thr Leu Ser Leu Thr Cys Thr Val Ser Gly Asp Ser
        275                 280                 285

Ile Thr Ser Gly Tyr Trp Asn Trp Ile Arg Gln His Pro Gly Lys Cys
    290                 295                 300

Leu Glu Tyr Ile Gly Tyr Ile Ser Tyr Thr Gly Ser Thr Tyr Tyr Asn
305                 310                 315                 320

Leu Ser Leu Lys Ser Arg Val Thr Ile Ser Arg Asp Thr Ser Lys Asn
                325                 330                 335
```

```
Gln Phe Ser Leu Lys Leu Ser Ser Val Thr Ala Ala Asp Thr Ala Val
            340                 345                 350

Tyr Tyr Cys Ala Arg Tyr Ile Leu Trp Leu Arg His Phe Asp Tyr Trp
        355                 360                 365

Gly Gln Gly Thr Leu Val Thr Val Ser Ser Ala Ser Thr Lys Gly Pro
    370                 375                 380

Ser Val Phe Pro Leu Ala Pro Cys Ser Arg Ser Thr Ser Glu Ser Thr
385                 390                 395                 400

Ala Ala Leu Gly Cys Leu Val Lys Asp Tyr Phe Pro Glu Pro Val Thr
                405                 410                 415

Val Ser Trp Asn Ser Gly Ala Leu Thr Ser Gly Val His Thr Phe Pro
            420                 425                 430

Ala Val Leu Gln Ser Ser Gly Leu Tyr Ser Leu Ser Ser Val Val Thr
        435                 440                 445

Val Pro Ser Ser Ser Leu Gly Thr Lys Thr Tyr Thr Cys Asn Val Asp
    450                 455                 460

His Lys Pro Ser Asn Thr Lys Val Asp Lys Arg Val Glu Ser Lys Tyr
465                 470                 475                 480

Gly Pro Pro Cys Pro Pro Cys Pro Ala Pro Glu Phe Leu Gly Gly Pro
                485                 490                 495

Ser Val Phe Leu Phe Pro Pro Lys Pro Lys Asp Thr Leu Met Ile Ser
            500                 505                 510

Arg Thr Pro Glu Val Thr Cys Val Val Val Asp Val Ser Gln Glu Asp
        515                 520                 525

Pro Glu Val Gln Phe Asn Trp Tyr Val Asp Gly Val Glu Val His Asn
    530                 535                 540

Ala Lys Thr Lys Pro Arg Glu Glu Gln Phe Asn Ser Thr Tyr Arg Val
545                 550                 555                 560

Val Ser Val Leu Thr Val Leu His Gln Asp Trp Leu Asn Gly Lys Glu
                565                 570                 575

Tyr Lys Cys Lys Val Ser Asn Lys Gly Leu Pro Ser Ser Ile Glu Lys
            580                 585                 590

Thr Ile Ser Lys Ala Lys Gly Gln Pro Arg Glu Pro Gln Val Cys Thr
        595                 600                 605

Leu Pro Pro Ser Gln Glu Glu Met Thr Lys Asn Gln Val Ser Leu Ser
    610                 615                 620

Cys Ala Val Lys Gly Phe Tyr Pro Ser Asp Ile Ala Val Glu Trp Glu
625                 630                 635                 640

Ser Asn Gly Gln Pro Glu Asn Asn Tyr Lys Thr Thr Pro Pro Val Leu
                645                 650                 655

Asp Ser Asp Gly Ser Phe Phe Leu Val Ser Arg Leu Thr Val Asp Lys
            660                 665                 670

Ser Arg Trp Gln Glu Gly Asn Val Phe Ser Cys Ser Val Met His Glu
        675                 680                 685

Ala Leu His Asn His Tyr Thr Gln Lys Ser Leu Ser Leu Ser Leu Gly
    690                 695                 700

Lys
705
```

<210> SEQ ID NO 104
<211> LENGTH: 708
<212> TYPE: PRT
<213> ORGANISM: Artificial Sequence
<220> FEATURE:
<223> OTHER INFORMATION: PL721-T2353-scFv-HC-PHR protein

<400> SEQUENCE: 104

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Asp Ser Ile Thr Ser Gly
            20                  25                  30

Tyr Trp Asn Trp Ile Arg Gln His Pro Gly Lys Gly Leu Glu Tyr Ile
        35                  40                  45

Gly Tyr Ile Ser Tyr Thr Gly Ser Thr Tyr Tyr Asn Leu Ser Leu Lys
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Tyr Ile Leu Trp Leu Arg His Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Glu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
```

```
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys Gly Gly Gly
        435                 440                 445

Gly Ser Gly Gly Gly Gly Ser Glu Val Gln Leu Val Glu Ser Gly Gly
    450                 455                 460

Gly Leu Val Gln Pro Gly Gly Ser Leu Arg Leu Ser Cys Ala Ala Ser
465                 470                 475                 480

Gly Phe Thr Phe Ser Asp His Trp Met Ser Trp Val Arg Gln Ala Pro
                485                 490                 495

Gly Lys Cys Met Glu Trp Ile Gly Asn Ile Gln Tyr Asp Gly Ser Tyr
            500                 505                 510

Thr Asn Tyr Ala Pro Ser Leu Lys Asn Arg Phe Thr Ile Ser Arg Asp
        515                 520                 525

Asn Ala Lys Asn Ser Leu Tyr Leu Gln Met Asn Ser Leu Arg Ala Glu
    530                 535                 540

Asp Thr Ala Thr Tyr Tyr Cys Thr Arg Gly His Phe Arg Ile Thr Met
545                 550                 555                 560

Ala Ser Met Gly Ala Ser Ala Ser Val Tyr Trp Gly Gln Gly Thr Met
                565                 570                 575

Val Thr Val Ser Ser Gly Gly Gly Gly Ser Gly Gly Gly Gly Ser Gly
            580                 585                 590

Gly Gly Gly Ser Gly Gly Gly Gly Ser Asp Ile Gln Met Thr Gln Ser
        595                 600                 605

Pro Ser Ser Leu Ser Ala Ser Val Gly Asp Arg Val Thr Ile Thr Cys
    610                 615                 620

Arg Thr Ser Gln Asp Ile Gly Asn Ser Leu Arg Trp Phe Gln Gln Lys
625                 630                 635                 640

Pro Gly Lys Ala Pro Lys Leu Leu Ile His Gly Ala Thr Asn Leu Ala
                645                 650                 655

Asn Gly Val Pro Ser Arg Phe Ser Gly Ser Gly Ser Gly Thr Asp Phe
            660                 665                 670

Thr Leu Thr Ile Ser Ser Leu Gln Pro Glu Asp Phe Ala Thr Tyr Tyr
        675                 680                 685

Cys Leu Gln His Asn Glu Tyr Pro Leu Thr Phe Gly Cys Gly Thr Lys
    690                 695                 700

Leu Glu Ile Lys
705


<210> SEQ ID NO 105
<211> LENGTH: 220
<212> TYPE: PRT
<213> ORGANISM: Artificial Sequence
<220> FEATURE:
<223> OTHER INFORMATION: HuPL721-VL1-PHR protein

<400> SEQUENCE: 105

Asp Ile Val Met Thr Gln Ser Pro Asp Ser Leu Ala Val Ser Leu Gly
1               5                   10                  15

Glu Arg Ala Thr Ile Ser Cys Lys Ser Ser Gln Ser Leu Leu Tyr Ser
            20                  25                  30

Ser Asn Gln Lys Asn Ser Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
```

```
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Gly Tyr Pro Leu Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 106
<211> LENGTH: 705
<212> TYPE: PRT
<213> ORGANISM: Artificial Sequence
<220> FEATURE:
<223> OTHER INFORMATION: HuPL743-scfab-hole-PHR protein

<400> SEQUENCE: 106

Asp Ile Val Met Thr Gln Ser Pro Asp Ser Leu Ala Val Ser Leu Gly
1               5                   10                  15

Glu Arg Val Thr Met Ser Cys Lys Ser Ser Gln Ser Leu Leu Tyr Ser
            20                  25                  30

Ser Asn Gln Lys Asn Ser Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Tyr Tyr Gly Tyr Pro Leu Thr Phe Gly Cys Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
```

```
        195                 200                 205

Ser Pro Val Thr Lys Ser Phe Asn Arg Gly Glu Cys Gly Gly Gly Gly
    210                 215                 220

Ser Gly Gly Gly Gly Ser Gly Gly Gly Gly Ser Gly Gly Gly Gly Ser
225                 230                 235                 240

Gly Gly Gly Gly Ser Gly Gly Gly Gly Ser Gly Gly Gly Gly Ser Gly
                245                 250                 255

Gly Gly Gly Ser Gln Val Gln Leu Gln Glu Ser Gly Pro Gly Leu Val
            260                 265                 270

Lys Pro Ser Gln Thr Leu Ser Leu Thr Cys Thr Val Ser Gly Asp Ser
        275                 280                 285

Ile Thr Ser Gly Tyr Trp Asn Trp Ile Arg Gln His Pro Gly Lys Cys
    290                 295                 300

Leu Glu Tyr Met Gly Tyr Ile Ser Tyr Thr Gly Ser Thr Tyr Tyr Asn
305                 310                 315                 320

Leu Ser Leu Lys Ser Arg Ile Thr Ile Ser Arg Asp Thr Ser Lys Asn
                325                 330                 335

Gln Tyr Ser Leu Lys Leu Ser Ser Val Thr Ala Ala Asp Thr Ala Val
            340                 345                 350

Tyr Tyr Cys Ala Arg Tyr Ile Leu Trp Leu Arg His Phe Asp Tyr Trp
        355                 360                 365

Gly Gln Gly Thr Leu Leu Thr Val Ser Ser Ala Ser Thr Lys Gly Pro
    370                 375                 380

Ser Val Phe Pro Leu Ala Pro Cys Ser Arg Ser Thr Ser Glu Ser Thr
385                 390                 395                 400

Ala Ala Leu Gly Cys Leu Val Lys Asp Tyr Phe Pro Glu Pro Val Thr
                405                 410                 415

Val Ser Trp Asn Ser Gly Ala Leu Thr Ser Gly Val His Thr Phe Pro
            420                 425                 430

Ala Val Leu Gln Ser Ser Gly Leu Tyr Ser Leu Ser Ser Val Val Thr
        435                 440                 445

Val Pro Ser Ser Ser Leu Gly Thr Lys Thr Tyr Thr Cys Asn Val Asp
    450                 455                 460

His Lys Pro Ser Asn Thr Lys Val Asp Lys Arg Val Glu Ser Lys Tyr
465                 470                 475                 480

Gly Pro Pro Cys Pro Pro Cys Pro Ala Pro Glu Phe Leu Gly Gly Pro
                485                 490                 495

Ser Val Phe Leu Phe Pro Pro Lys Pro Lys Asp Thr Leu Met Ile Ser
            500                 505                 510

Arg Thr Pro Glu Val Thr Cys Val Val Val Asp Val Ser Gln Glu Asp
        515                 520                 525

Pro Glu Val Gln Phe Asn Trp Tyr Val Asp Gly Val Glu Val His Asn
    530                 535                 540

Ala Lys Thr Lys Pro Arg Glu Glu Gln Phe Asn Ser Thr Tyr Arg Val
545                 550                 555                 560

Val Ser Val Leu Thr Val Leu His Gln Asp Trp Leu Asn Gly Lys Glu
                565                 570                 575

Tyr Lys Cys Lys Val Ser Asn Lys Gly Leu Pro Ser Ser Ile Glu Lys
            580                 585                 590

Thr Ile Ser Lys Ala Lys Gly Gln Pro Arg Glu Pro Gln Val Cys Thr
        595                 600                 605

Leu Pro Pro Ser Gln Glu Glu Met Thr Lys Asn Gln Val Ser Leu Ser
    610                 615                 620
```

```
Cys Ala Val Lys Gly Phe Tyr Pro Ser Asp Ile Ala Val Glu Trp Glu
625                 630                 635                 640

Ser Asn Gly Gln Pro Glu Asn Asn Tyr Lys Thr Thr Pro Pro Val Leu
                645                 650                 655

Asp Ser Asp Gly Ser Phe Phe Leu Val Ser Arg Leu Thr Val Asp Lys
            660                 665                 670

Ser Arg Trp Gln Glu Gly Asn Val Phe Ser Cys Ser Val Met His Glu
        675                 680                 685

Ala Leu His Asn His Tyr Thr Gln Lys Ser Leu Ser Leu Ser Leu Gly
    690                 695                 700

Lys
705


<210> SEQ ID NO 107
<211> LENGTH: 708
<212> TYPE: PRT
<213> ORGANISM: Artificial Sequence
<220> FEATURE:
<223> OTHER INFORMATION: PL743-T2353-scFv-HC-PHR protein

<400> SEQUENCE: 107

Gln Val Gln Leu Gln Glu Ser Gly Pro Gly Leu Val Lys Pro Ser Gln
1               5                   10                  15

Thr Leu Ser Leu Thr Cys Thr Val Ser Gly Asp Ser Ile Thr Ser Gly
            20                  25                  30

Tyr Trp Asn Trp Ile Arg Gln His Pro Gly Lys Gly Leu Glu Tyr Met
        35                  40                  45

Gly Tyr Ile Ser Tyr Thr Gly Ser Thr Tyr Tyr Asn Leu Ser Leu Lys
    50                  55                  60

Ser Arg Ile Thr Ile Ser Arg Asp Thr Ser Lys Asn Gln Tyr Ser Leu
65                  70                  75                  80

Lys Leu Ser Ser Val Thr Ala Ala Asp Thr Ala Val Tyr Tyr Cys Ala
                85                  90                  95

Arg Tyr Ile Leu Trp Leu Arg His Phe Asp Tyr Trp Gly Gln Gly Thr
            100                 105                 110

Leu Leu Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Glu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270
```

```
Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys Gly Gly Gly
        435                 440                 445

Gly Ser Gly Gly Gly Gly Ser Glu Val Gln Leu Val Glu Ser Gly Gly
    450                 455                 460

Gly Leu Val Gln Pro Gly Gly Ser Leu Arg Leu Ser Cys Ala Ala Ser
465                 470                 475                 480

Gly Phe Thr Phe Ser Asp His Trp Met Ser Trp Val Arg Gln Ala Pro
                485                 490                 495

Gly Lys Cys Met Glu Trp Ile Gly Asn Ile Gln Tyr Asp Gly Ser Tyr
            500                 505                 510

Thr Asn Tyr Ala Pro Ser Leu Lys Asn Arg Phe Thr Ile Ser Arg Asp
        515                 520                 525

Asn Ala Lys Asn Ser Leu Tyr Leu Gln Met Asn Ser Leu Arg Ala Glu
    530                 535                 540

Asp Thr Ala Thr Tyr Tyr Cys Thr Arg Gly His Phe Arg Ile Thr Met
545                 550                 555                 560

Ala Ser Met Gly Ala Ser Ala Ser Val Tyr Trp Gly Gln Gly Thr Met
                565                 570                 575

Val Thr Val Ser Ser Gly Gly Gly Gly Ser Gly Gly Gly Gly Ser Gly
            580                 585                 590

Gly Gly Gly Ser Gly Gly Gly Gly Ser Asp Ile Gln Met Thr Gln Ser
        595                 600                 605

Pro Ser Ser Leu Ser Ala Ser Val Gly Asp Arg Val Thr Ile Thr Cys
    610                 615                 620

Arg Thr Ser Gln Asp Ile Gly Asn Ser Leu Arg Trp Phe Gln Gln Lys
625                 630                 635                 640

Pro Gly Lys Ala Pro Lys Leu Leu Ile His Gly Ala Thr Asn Leu Ala
                645                 650                 655

Asn Gly Val Pro Ser Arg Phe Ser Gly Ser Gly Ser Gly Thr Asp Phe
            660                 665                 670

Thr Leu Thr Ile Ser Ser Leu Gln Pro Glu Asp Phe Ala Thr Tyr Tyr
        675                 680                 685
```

```
Cys Leu Gln His Asn Glu Tyr Pro Leu Thr Phe Gly Cys Gly Thr Lys
    690                 695                 700

Leu Glu Ile Lys
705


<210> SEQ ID NO 108
<211> LENGTH: 220
<212> TYPE: PRT
<213> ORGANISM: Artificial Sequence
<220> FEATURE:
<223> OTHER INFORMATION: HuPL743-VL3-PHR protein

<400> SEQUENCE: 108

Asp Ile Val Met Thr Gln Ser Pro Asp Ser Leu Ala Val Ser Leu Gly
1               5                   10                  15

Glu Arg Val Thr Met Ser Cys Lys Ser Ser Gln Ser Leu Leu Tyr Ser
            20                  25                  30

Ser Asn Gln Lys Asn Ser Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Tyr Tyr Gly Tyr Pro Leu Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 109
<211> LENGTH: 703
<212> TYPE: PRT
<213> ORGANISM: Artificial Sequence
<220> FEATURE:
<223> OTHER INFORMATION: HuPL1642-scfab-hole-PHR protein

<400> SEQUENCE: 109

Asp Ile Val Met Thr Gln Ser Pro Asp Ser Leu Ala Val Ser Leu Gly
1               5                   10                  15

Glu Arg Val Thr Met Arg Cys Lys Ser Ser Gln Ser Leu Ser Trp Ser
            20                  25                  30

Glu Asn Gln Asn Asn Tyr Leu Ser Trp Tyr Gln Gln Lys Pro Gly Gln
        35                  40                  45

Pro Pro Lys Leu Leu Ile Tyr Gly Ala Ser Ile Arg Glu Ser Gly Val
    50                  55                  60
```

-continued

Pro Asp Arg Phe Ser Gly Ser Gly Ser Gly Thr Asp Phe Thr Leu Thr
65 70 75 80

Ile Ser Ser Val Gln Ala Glu Asp Val Gly Val Tyr Tyr Cys Gln His
85 90 95

Asn His Gly Ser Phe Leu Pro Tyr Thr Phe Gly Cys Gly Thr Lys Leu
100 105 110

Glu Ile Lys Arg Thr Val Ala Ala Pro Ser Val Phe Ile Phe Pro Pro
115 120 125

Ser Asp Glu Gln Leu Lys Ser Gly Thr Ala Ser Val Val Cys Leu Leu
130 135 140

Asn Asn Phe Tyr Pro Arg Glu Ala Lys Val Gln Trp Lys Val Asp Asn
145 150 155 160

Ala Leu Gln Ser Gly Asn Ser Gln Glu Ser Val Thr Glu Gln Asp Ser
165 170 175

Lys Asp Ser Thr Tyr Ser Leu Ser Ser Thr Leu Thr Leu Ser Lys Ala
180 185 190

Asp Tyr Glu Lys His Lys Val Tyr Ala Cys Glu Val Thr His Gln Gly
195 200 205

Leu Ser Ser Pro Val Thr Lys Ser Phe Asn Arg Gly Glu Cys Gly Gly
210 215 220

Gly Gly Ser Gly Gly Gly Gly Ser Gly Gly Gly Gly Ser Gly Gly Gly
225 230 235 240

Gly Ser Gly Gly Gly Gly Ser Gly Gly Gly Gly Ser Gly Gly Gly Gly
245 250 255

Ser Gly Gly Gly Gly Ser Gln Val Gln Leu Val Gln Ser Gly Ala Glu
260 265 270

Val Ala Lys Pro Gly Ala Ser Val Lys Met Ser Cys Lys Ala Ser Gly
275 280 285

Tyr Thr Phe Thr Arg Asn Thr Met His Trp Ile Lys Gln Ala Pro Gly
290 295 300

Gln Cys Leu Glu Trp Ile Gly Phe Ile Asp Pro His Asn Thr Tyr Thr
305 310 315 320

Arg Tyr Asn Gln Lys Phe Lys Asp Arg Ala Thr Leu Thr Ala Asp Thr
325 330 335

Ser Ala Ser Thr Ala Tyr Met Glu Leu Ser Ser Leu Arg Ser Glu Asp
340 345 350

Thr Ala Val Tyr Tyr Cys Ala Arg Trp Pro Met Asp Tyr Trp Gly Gln
355 360 365

Gly Thr Leu Val Thr Val Ser Ser Ala Ser Thr Lys Gly Pro Ser Val
370 375 380

Phe Pro Leu Ala Pro Cys Ser Arg Ser Thr Ser Glu Ser Thr Ala Ala
385 390 395 400

Leu Gly Cys Leu Val Lys Asp Tyr Phe Pro Glu Pro Val Thr Val Ser
405 410 415

Trp Asn Ser Gly Ala Leu Thr Ser Gly Val His Thr Phe Pro Ala Val
420 425 430

Leu Gln Ser Ser Gly Leu Tyr Ser Leu Ser Ser Val Val Thr Val Pro
435 440 445

Ser Ser Ser Leu Gly Thr Lys Thr Tyr Thr Cys Asn Val Asp His Lys
450 455 460

Pro Ser Asn Thr Lys Val Asp Lys Arg Val Glu Ser Lys Tyr Gly Pro
465 470 475 480

```
Pro Cys Pro Pro Cys Pro Ala Pro Glu Phe Leu Gly Gly Pro Ser Val
                485                 490                 495

Phe Leu Phe Pro Pro Lys Pro Lys Asp Thr Leu Met Ile Ser Arg Thr
            500                 505                 510

Pro Glu Val Thr Cys Val Val Val Asp Val Ser Gln Glu Asp Pro Glu
        515                 520                 525

Val Gln Phe Asn Trp Tyr Val Asp Gly Val Glu Val His Asn Ala Lys
    530                 535                 540

Thr Lys Pro Arg Glu Glu Gln Phe Asn Ser Thr Tyr Arg Val Val Ser
545                 550                 555                 560

Val Leu Thr Val Leu His Gln Asp Trp Leu Asn Gly Lys Glu Tyr Lys
                565                 570                 575

Cys Lys Val Ser Asn Lys Gly Leu Pro Ser Ser Ile Glu Lys Thr Ile
            580                 585                 590

Ser Lys Ala Lys Gly Gln Pro Arg Glu Pro Gln Val Cys Thr Leu Pro
        595                 600                 605

Pro Ser Gln Glu Glu Met Thr Lys Asn Gln Val Ser Leu Ser Cys Ala
    610                 615                 620

Val Lys Gly Phe Tyr Pro Ser Asp Ile Ala Val Glu Trp Glu Ser Asn
625                 630                 635                 640

Gly Gln Pro Glu Asn Asn Tyr Lys Thr Thr Pro Pro Val Leu Asp Ser
                645                 650                 655

Asp Gly Ser Phe Phe Leu Val Ser Arg Leu Thr Val Asp Lys Ser Arg
            660                 665                 670

Trp Gln Glu Gly Asn Val Phe Ser Cys Ser Val Met His Glu Ala Leu
        675                 680                 685

His Asn His Tyr Thr Gln Lys Ser Leu Ser Leu Ser Leu Gly Lys
    690                 695                 700
```

<210> SEQ ID NO 110
<211> LENGTH: 704
<212> TYPE: PRT
<213> ORGANISM: Artificial Sequence
<220> FEATURE:
<223> OTHER INFORMATION: PL1642-T2353-scFv-HC-PHR protein

<400> SEQUENCE: 110

```
Gln Val Gln Leu Val Gln Ser Gly Ala Glu Val Ala Lys Pro Gly Ala
1               5                   10                  15

Ser Val Lys Met Ser Cys Lys Ala Ser Gly Tyr Thr Phe Thr Arg Asn
            20                  25                  30

Thr Met His Trp Ile Lys Gln Ala Pro Gly Gln Arg Leu Glu Trp Ile
        35                  40                  45

Gly Phe Ile Asp Pro His Asn Thr Tyr Thr Arg Tyr Asn Gln Lys Phe
    50                  55                  60

Lys Asp Arg Ala Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Pro Met Asp Tyr Trp Gly Gln Gly Thr Leu Val Thr Val
            100                 105                 110

Ser Ser Ala Ser Thr Lys Gly Pro Ser Val Phe Pro Leu Ala Pro Cys
        115                 120                 125

Ser Arg Ser Thr Ser Glu Ser Thr Ala Ala Leu Gly Cys Leu Val Lys
    130                 135                 140
```

```
Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Lys Thr Tyr Thr Cys Asn Val Asp His Lys Pro Ser Asn Thr Lys Val
        195                 200                 205

Asp Lys Arg Val Glu Ser Lys Tyr Gly Pro Pro Cys Pro Pro Cys Pro
    210                 215                 220

Ala Pro Glu Phe Glu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser Gln Glu Asp Pro Glu Val Gln Phe Asn Trp Tyr
            260                 265                 270

Val Asp Gly Val Glu Val His Asn Ala Lys Thr Lys Pro Arg Glu Glu
        275                 280                 285

Gln Phe Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Gly Leu Pro Ser Ser Ile Glu Lys Thr Ile Ser Lys Ala Lys Gly Gln
                325                 330                 335

Pro Arg Glu Pro Gln Val Tyr Thr Leu Pro Pro Ser Gln Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Arg Leu Thr Val Asp Lys Ser Arg Trp Gln Glu Gly Asn Val
                405                 410                 415

Phe Ser Cys Ser Val Met His Glu Ala Leu His Asn His Tyr Thr Gln
            420                 425                 430

Lys Ser Leu Ser Leu Ser Leu Gly Lys Gly Gly Gly Gly Ser Gly Gly
        435                 440                 445

Gly Gly Ser Glu Val Gln Leu Val Glu Ser Gly Gly Gly Leu Val Gln
    450                 455                 460

Pro Gly Gly Ser Leu Arg Leu Ser Cys Ala Ala Ser Gly Phe Thr Phe
465                 470                 475                 480

Ser Asp His Trp Met Ser Trp Val Arg Gln Ala Pro Gly Lys Cys Met
                485                 490                 495

Glu Trp Ile Gly Asn Ile Gln Tyr Asp Gly Ser Tyr Thr Asn Tyr Ala
            500                 505                 510

Pro Ser Leu Lys Asn Arg Phe Thr Ile Ser Arg Asp Asn Ala Lys Asn
        515                 520                 525

Ser Leu Tyr Leu Gln Met Asn Ser Leu Arg Ala Glu Asp Thr Ala Thr
    530                 535                 540

Tyr Tyr Cys Thr Arg Gly His Phe Arg Ile Thr Met Ala Ser Met Gly
545                 550                 555                 560

Ala Ser Ala Ser Val Tyr Trp Gly Gln Gly Thr Met Val Thr Val Ser
```

```
                565                 570                 575

Ser Gly Gly Gly Gly Ser Gly Gly Gly Gly Ser Gly Gly Gly Gly Ser
            580                 585                 590

Gly Gly Gly Gly Ser Asp Ile Gln Met Thr Gln Ser Pro Ser Ser Leu
        595                 600                 605

Ser Ala Ser Val Gly Asp Arg Val Thr Ile Thr Cys Arg Thr Ser Gln
    610                 615                 620

Asp Ile Gly Asn Ser Leu Arg Trp Phe Gln Gln Lys Pro Gly Lys Ala
625                 630                 635                 640

Pro Lys Leu Leu Ile His Gly Ala Thr Asn Leu Ala Asn Gly Val Pro
                645                 650                 655

Ser Arg Phe Ser Gly Ser Gly Ser Gly Thr Asp Phe Thr Leu Thr Ile
            660                 665                 670

Ser Ser Leu Gln Pro Glu Asp Phe Ala Thr Tyr Tyr Cys Leu Gln His
        675                 680                 685

Asn Glu Tyr Pro Leu Thr Phe Gly Cys Gly Thr Lys Leu Glu Ile Lys
    690                 695                 700


<210> SEQ ID NO 111
<211> LENGTH: 222
<212> TYPE: PRT
<213> ORGANISM: Artificial Sequence
<220> FEATURE:
<223> OTHER INFORMATION: HuPL1642-VL2-PHR protein

<400> SEQUENCE: 111

Asp Ile Val Met Thr Gln Ser Pro Asp Ser Leu Ala Val Ser Leu Gly
1               5                   10                  15

Glu Arg Val Thr Met Arg Cys Lys Ser Ser Gln Ser Leu Ser Trp Ser
            20                  25                  30

Glu Asn Gln Asn Asn Tyr Leu Ser Trp Tyr Gln Gln Lys Pro Gly Gln
        35                  40                  45

Pro Pro Lys Leu Leu Ile Tyr Gly Ala Ser Ile Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Gly Val Tyr Tyr Cys Gln His
                85                  90                  95

Asn His Gly Ser Phe Leu Pro Tyr Thr Phe Gly Gln Gly Thr Lys Leu
            100                 105                 110

Glu Ile Lys Arg Thr Val Ala Ala Pro Ser Val Phe Ile Phe Pro Pro
        115                 120                 125

Ser Asp Glu Gln Leu Lys Ser Gly Thr Ala Ser Val Val Cys Leu Leu
    130                 135                 140

Asn Asn Phe Tyr Pro Arg Glu Ala Lys Val Gln Trp Lys Val Asp Asn
145                 150                 155                 160

Ala Leu Gln Ser Gly Asn Ser Gln Glu Ser Val Thr Glu Gln Asp Ser
                165                 170                 175

Lys Asp Ser Thr Tyr Ser Leu Ser Ser Thr Leu Thr Leu Ser Lys Ala
            180                 185                 190

Asp Tyr Glu Lys His Lys Val Tyr Ala Cys Glu Val Thr His Gln Gly
        195                 200                 205

Leu Ser Ser Pro Val Thr Lys Ser Phe Asn Arg Gly Glu Cys
    210                 215                 220
```

```
<210> SEQ ID NO 112
<211> LENGTH: 5
<212> TYPE: PRT
<213> ORGANISM: Artificial Sequence
<220> FEATURE:
<223> OTHER INFORMATION: linker

<400> SEQUENCE: 112

Gly Gly Gly Gly Ser
1               5
```